United States Patent
Yang et al.

(10) Patent No.: US 9,493,802 B2
(45) Date of Patent: *Nov. 15, 2016

(54) USE OF GLYCOHYDROLASE 61 PROTEIN VARIANTS WITH IMPROVED THERMOSTABILITY FOR PROCESSING CELLULOSE

(75) Inventors: Jie Yang, Foster City, CA (US); Louis Clark, San Francisco, CA (US); Onorato Campopiano, Hayward, CA (US); Kripa Rao, San Mateo, CA (US); Lorand Szabo, Budapest (HU); Janos Torok, Budapest (HU); Dipnath Baidyaroy, Fremont, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/640,471

(22) PCT Filed: Aug. 22, 2011

(86) PCT No.: PCT/US2011/048700
§ 371 (c)(1),
(2), (4) Date: Jan. 29, 2014

(87) PCT Pub. No.: WO2012/024698
PCT Pub. Date: Feb. 23, 2012

(65) Prior Publication Data
US 2014/0186896 A1    Jul. 3, 2014

Related U.S. Application Data

(63) Continuation of application No. 13/215,193, filed on Aug. 22, 2011.

(60) Provisional application No. 61/375,788, filed on Aug. 20, 2010.

(51) Int. Cl.
| | |
|---|---|
| C12P 19/02 | (2006.01) |
| C12N 9/30 | (2006.01) |
| C12N 9/42 | (2006.01) |
| C12P 7/10 | (2006.01) |
| C12P 19/14 | (2006.01) |
| C12P 7/14 | (2006.01) |

(52) U.S. Cl.
CPC .............. *C12P 19/02* (2013.01); *C12N 9/242* (2013.01); *C12N 9/2434* (2013.01); *C12P 7/10* (2013.01); *C12P 7/14* (2013.01); *C12P 19/14* (2013.01); *Y02E 50/16* (2013.01); *Y02P 20/52* (2015.11)

(58) Field of Classification Search
CPC ........... C12P 19/14; C12P 7/10; C12P 19/02; C12P 9/2445; C12N 9/2437; C12N 9/2445; C12Y 302/01091; C12Y 302/01021
See application file for complete search history.

(56) References Cited

U.S. PATENT DOCUMENTS

| | | |
|---|---|---|
| 3,990,944 A | 11/1976 | Gauss et al. |
| 3,990,945 A | 11/1976 | Huff et al. |
| 4,356,196 A | 10/1982 | Hultquist |
| 4,461,648 A | 7/1984 | Foody |
| 4,556,430 A | 12/1985 | Converse et al. |
| 4,600,590 A | 7/1986 | Dale |
| 5,037,663 A | 8/1991 | Dale |
| 5,171,592 A | 12/1992 | Holtzapple et al. |
| 5,605,793 A | 2/1997 | Stemmer |
| 5,789,210 A | 8/1998 | Ho et al. |
| 5,811,238 A | 9/1998 | Stemmer et al. |
| 5,811,381 A | 9/1998 | Emalfarb et al. |
| 5,830,721 A | 11/1998 | Stemmer et al. |
| 5,834,252 A | 11/1998 | Stemmer et al. |
| 5,837,458 A | 11/1998 | Minshull et al. |
| 5,866,382 A | 2/1999 | Hallborn et al. |
| 5,928,905 A | 7/1999 | Stemmer et al. |
| 5,939,544 A | 8/1999 | Karstens et al. |
| 6,015,707 A | 1/2000 | Emalfarb et al. |
| 6,096,548 A | 8/2000 | Stemmer |
| 6,106,888 A | 8/2000 | Dale et al. |
| 6,117,679 A | 9/2000 | Stemmer |
| 6,132,970 A | 10/2000 | Stemmer |
| 6,165,793 A | 12/2000 | Stemmer |

(Continued)

FOREIGN PATENT DOCUMENTS

| | | |
|---|---|---|
| EP | 0137280 B1 | 3/1992 |
| EP | 0450430 B1 | 6/1997 |

(Continued)

OTHER PUBLICATIONS

Badhan et al., "Production of Mulitpule Xylanolytic and Celluloytic Enzymes by Thermophillic Fungus *Myceliopthorn* sp. IM 387099," *Bioresource Technology*, 98-504-510 (2007).

(Continued)

*Primary Examiner* — Paul Holland
(74) *Attorney, Agent, or Firm* — Kilpatrick Townsend & Stockton LLP

(57) ABSTRACT

The invention provides recombinant GH61 proteins obtained from *Myceliophtora thermophila*, and nucleic acids that encode such proteins. The invention also provides protein fractions isolated from *M. thermophila* supernatant that have GH61 protein activity. These preparations can be used to increase yield of products from reactions in which a cellulose-containing substrate undergoes saccharification by one or more cellulase enzymes, such as endoglucanase, β-glucosidase, or cellobiohydrolase. Combinations of GH61 protein and cellulases can be used to break down cellulosic biomass into fermentable sugars in the production of ethanol.

24 Claims, 2 Drawing Sheets

(56) References Cited

U.S. PATENT DOCUMENTS

| | | |
|---|---|---|
| 6,176,176 B1 | 1/2001 | Dale et al. |
| 6,180,406 B1 | 1/2001 | Stemmer |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,475,768 B1 | 11/2002 | Otero et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,573,086 B1 | 6/2003 | Emalfrab et al. |
| 6,573,098 B1 | 6/2003 | Stemmer |
| 6,576,467 B1 | 6/2003 | Stemmer |
| 6,579,678 B1 | 6/2003 | Patten et al. |
| 6,582,944 B1 | 6/2003 | Hallborn et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,773,900 B2 | 8/2004 | Short et al. |
| 6,939,689 B2 | 9/2005 | Short et al. |
| 6,946,296 B2 | 9/2005 | Patten et al. |
| 6,961,664 B2 | 11/2005 | Selifonov et al. |
| 6,995,017 B1 | 2/2006 | Stemmer |
| 7,024,312 B1 | 4/2006 | Selfinov et al. |
| 7,058,515 B1 | 6/2006 | Selfinov et al. |
| 7,105,297 B2 | 9/2006 | Minshull et al. |
| 7,148,054 B2 | 12/2006 | delCardayre et al. |
| 7,271,244 B2 | 9/2007 | Dotson et al. |
| 7,273,738 B2 | 9/2007 | Schnorr et al. |
| 7,288,375 B2 | 10/2007 | Stemmer et al. |
| 7,361,495 B2 | 4/2008 | Brown et al. |
| 7,399,627 B2 | 7/2008 | Emalfarb et al. |
| 7,421,347 B2 | 9/2008 | Selfinov et al. |
| 7,430,477 B2 | 9/2008 | Selfinov et al. |
| 7,465,791 B1 | 12/2008 | Hallberg et al. |
| 7,527,927 B1 | 5/2009 | Ho et al. |
| 7,534,564 B2 | 5/2009 | Patten et al. |
| 7,620,500 B2 | 11/2009 | Mundorff et al. |
| 7,620,502 B2 | 11/2009 | Selfinov et al. |
| 7,622,284 B2 | 11/2009 | Op Den Camp et al. |
| 7,629,170 B2 | 12/2009 | delCardayre et al. |
| 7,647,184 B2 | 1/2010 | Vega et al. |
| 7,702,464 B1 | 4/2010 | Emig et al. |
| 7,741,466 B2 | 6/2010 | Brown et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,754,457 B2 | 7/2010 | Foody et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,803,590 B2 | 9/2010 | Schnorr et al. |
| 7,853,410 B2 | 12/2010 | Selfinov et al. |
| 7,868,138 B2 | 1/2011 | Stemmer et al. |
| 7,873,499 B2 | 1/2011 | Selfinov et al. |
| 7,904,249 B2 | 3/2011 | Selfinov et al. |
| 7,957,912 B2 | 6/2011 | Selfinov et al. |
| 7,981,614 B2 | 7/2011 | Stemmer et al. |
| 8,088,608 B2 | 1/2012 | Yang et al. |
| 8,206,960 B1 | 6/2012 | Yang et al. |
| 8,236,551 B2 | 8/2012 | Dhawan et al. |
| 8,298,795 B2 * | 10/2012 | Yang et al. .............. 435/99 |
| 2005/0191736 A1 | 9/2005 | Brown et al. |
| 2006/0005279 A1 | 1/2006 | Dotson et al. |
| 2007/0031953 A1 | 2/2007 | Dunson, Jr. et al. |
| 2007/0238155 A1 | 10/2007 | Gusakov et al. |
| 2008/0057541 A1 | 3/2008 | Hill et al. |
| 2008/0104724 A1 | 5/2008 | Sticklen et al. |
| 2008/0194005 A1 | 8/2008 | Emalfarb et al. |
| 2008/0206815 A1 | 8/2008 | Brown et al. |
| 2008/0220990 A1 | 9/2008 | Fox |
| 2009/0061484 A1 | 3/2009 | Scott et al. |
| 2009/0099079 A1 | 4/2009 | Emalfarb et al. |
| 2009/0209009 A1 | 8/2009 | Tolan et al. |
| 2009/0312196 A1 | 12/2009 | Colbeck et al. |
| 2010/0124769 A1 | 5/2010 | Brown et al. |
| 2010/0143971 A1 | 6/2010 | Spodsberg et al. |
| 2010/0159494 A1 | 6/2010 | Sweeney |
| 2010/0197556 A1 | 8/2010 | Brown et al. |
| 2010/0267089 A1 | 10/2010 | Yang et al. |
| 2010/0299788 A1 | 11/2010 | Harris et al. |
| 2010/0299789 A1 | 11/2010 | Harris et al. |
| 2010/0304434 A1 | 12/2010 | Harris et al. |
| 2010/0306881 A1 | 12/2010 | Harris et al. |
| 2010/0317059 A1 | 12/2010 | Postlethwaite et al. |
| 2011/0034342 A1 | 2/2011 | Fox |
| 2011/0114744 A1 | 5/2011 | Ricciardi et al. |
| 2011/0124058 A1 | 5/2011 | Baidyaroy et al. |
| 2011/0129881 A1 | 6/2011 | Yang et al. |
| 2012/0208235 A1 | 8/2012 | Zhang et al. |
| 2012/0276594 A1 | 11/2012 | Voladri et al. |
| 2013/0323822 A1 | 12/2013 | Brevnova et al. |

FOREIGN PATENT DOCUMENTS

| | | |
|---|---|---|
| WO | 95/22625 A1 | 8/1995 |
| WO | 96/00787 A1 | 1/1996 |
| WO | 97/00078 A1 | 1/1997 |
| WO | 97/35966 A1 | 10/1997 |
| WO | 98/15633 A1 | 4/1998 |
| WO | 98/27230 A1 | 6/1998 |
| WO | 00/42651 A1 | 7/2000 |
| WO | 01/75767 A2 | 10/2001 |
| WO | 2005/047647 A2 | 8/2005 |
| WO | 2005/074647 A2 | 8/2005 |
| WO | 2007/109441 A2 | 9/2007 |
| WO | 2008/073914 A2 | 6/2008 |
| WO | 2008/130603 A2 | 10/2008 |
| WO | 2009/033071 A2 | 3/2009 |
| WO | 2009/045651 A2 | 4/2009 |
| WO | 2009/085859 A2 | 7/2009 |
| WO | 2009/085864 A2 | 7/2009 |

(56) References Cited

FOREIGN PATENT DOCUMENTS

| | | |
|---|---|---|
| WO | 2009/085868 A1 | 7/2009 |
| WO | 2009/085935 A2 | 7/2009 |
| WO | WO 2009108941 A2 * | 9/2009 |
| WO | 2009/152336 A1 | 12/2009 |
| WO | 2010/022511 A | 3/2010 |
| WO | 2010/107303 A2 | 9/2010 |
| WO | 2010/138754 A1 | 12/2010 |
| WO | 2010/148148 A2 | 12/2010 |
| WO | 2011/041594 A1 | 4/2011 |
| WO | 2011/059740 A1 | 5/2011 |
| WO | 2011/153516 A2 | 12/2011 |
| WO | 2012/024698 A1 | 2/2012 |
| WO | 2012/027374 A2 | 3/2012 |
| WO | 2012/044835 A1 | 4/2012 |
| WO | 2012/088159 A2 | 6/2012 |
| WO | 2012/125925 A2 | 9/2012 |

OTHER PUBLICATIONS

Roy et al., "Purification and Properties of an Extracellular Endoglucanase From Mycelliophthors Thermophilla D-14 (ATCC 48104," *Journal of General Microbiology*, 136:1967-1971 (1990).
International Search Report and Written Opinion of PCT/US2011/048700, mailed on Nov. 15, 2011, 18 pages.
Banerjee et al., "Synthetic multi-component enzyme mixtures fir deconstruction of linocellulosic biomass", Bioresource Technology, 2010, p. 9097-9105, vol. 101.
Berka et al., "Comparative genomic analysis of the thermophilic biomass-degrading fungi *Myceliophthora thermophilia* and *Thielavia terrestris*", Nature Biotechnology, Oct. 2011, p. 922-927, vol. 29, No. 10.
Berka et al., "Supplemental to: Comparative genomic analysis of the thermophilic biomass-degrading fungi *Myceliophthora thermophilia* and *Thielavia terrestris*", Nature Biotechnology, 1976, p. 1-46.
Davies et al., "Structures and mechanisms of glycosyl hydrolases", Structure, Sep. 15, 1995, p. 853-859, vol. 3, No. 9.
Hara et al., Cloning and sequence analysis of endoglucanase genes from an industrial fungus, *Aspergillus kawachii*, Biosci Biotechnol Biochem.;67(9):2010-3 (Sep. 2003).
Harris et al., "Stimulation of Lignocellulosic Biomass Hydrolase by Proteins of Glycoside Hydrolase Family 61: Structure and Function of a Large, Enigmatic Family," *Biochemistry*, 49:3305-3316 (2010).
Henrissat et al., "Conserved catalytic machinery and the prediction of a common fold for several families of glycosyl hydrolases", Proc. Natl. Acad. Sci. USA, Jul. 1995, p. 7090-7094, vol. 92.
Ladisch et al., "Process considerations in the enzymatic hydrolysis of biomass," *Enzyme Microb. Technol*, 5:82-102 (1983).
Langston et al, Oxidoreductive Cellulose Depolymerization by the Enzymes Cellobiose Dehydrogenase and Glycoside Hydrolase , Applied and Environmental Microbiology, Oct. 2011, p. 7007-7015.
Phillips et al., "Cellobiose dehydrogenase and a copper-dependent polysaccharide monooxygenase potentiate cellulose degradation by neurospora crassa", ACS Chem. Biol., 2011, p. 1399-1406, vol. 6, No. 12.
Quinlan et al., InsiGHts into the Oxidative Degradation of Cellulose by a Copper Metalloenzyme That Exploits Biomass Components, *Proc. Natl. Acad. Sci. USA*, 108(37):15079-15081 (Sep. 13, 2011).
Quinlan et al., Supporting Information 10.31073/PNAS 1105776108, 9 Pages Retrieved on Oct. 21, 2011 from URL <http://www.pnas.org/content/suppl/2011/08/26/1105776108.DCSupplemental/pnas.201105776SI.pdf.
Altschul, S.F., et al. "Gapped BLAST and PSI-BLAST: a new generation of protein database search programs," Nucleic Acids Res., 25(17):3389-3402 (1997).
Altschul, S.F., et al., "Basic Local Alignment Search Tool," J. Mol. Biol., 215: 403-410 [1990].
Badhan A.K., et al., "Production of multiple xylanolytic and cellulolytic enzymes by thermolphilic fungus *Myceliophthora* sp. IMI 387099," Biores. Technol., 98:504-10 [2007].

Blaiseau, P-L., et al., "Primary structure of a chitinase-encoding gene (chi1) from the filamentous fungus *Aphanocladium album*: similarity to bacterial chitanases," Gene, 120(2):243-248 (1992).
Boel, E., et al., "Two different types of intervening sequences in the glucoamylase gene from Aspergillus niger," EMBO J., 3(7):1581-1585 (1984).
Botstein, D., et al., "Strategies and Applications of In Vitro Mutagenesis," Science, 229(4719):1193-1201 [1985].
Carter, P., "Site-directed mutagenesis," Biochem. J., 237:1-7[1986].
Christians, F.C., et al., "Directed evolution of thymidine kinase for AZT phosphorylation using DNA family shuffling," Nat. Biotechnol., 17:259-264 [1999].
Crameri A., et al., "DNA shuffling of a family of genes from diverse species accelerates directed evolution," Nature, 391:288-291 [1998].
Crameri, A., et al. "Improved green fluorescent protein by molecular evolution using DNA shuffling," Nat. Biotechnol., 14:315-319 [1996].
Crameri, A., et al. "Molecular evolution of an arsenate detoxification pathway by DNA shuffling," Nat. Biotechnol., 15:436-438 [1997].
Dale, S.J., et al., "Oligonucleotide-Directed Random Mutagenesis Using the Phosphorothioate Method," Meth. Mol. Biol., 57:369-74 [1996].
Drissen, R.E.T., et al., "Modelling ethanol production from cellulose: separate hydrolysis and fermentation versus simultaneous saccharification and fermentation," Biocat. Biotransform., 27:27-35 [2009].
Foreman, P.K., et al., "Transcriptional Regulation of Biomass-degrading Enzymes in the Filamentous Fungus *Trichoderma reesei*," J. Bioi. Chern., 278(34):31988-31997 [2003].
Garg. A.K., "An addition to the genus *Chrysosporium corda*," Mycopathologia, 30(3-4):221-224 (1966).
Glenn, J.K., et al., "Mn(II() Oxidation Is the Principal Function of the Extracellular Mn-Peroxidase from Phanerochaete chrysosporium," Arch. Biochem. Biophys., 251(2):688—696 [1986].
Greener, A., et al., "An efficient random mutagenesis technique using an *E. coli* mutator strain," Methods Mol. Biol., 57:375-385 [1996].
Guo, Z., et al., "3'-End-Forming Signals of Yeast mRNA," Mol. Cell. Biol., 15(11):5983-5990 [1995].
Harayama, S., "Artificial evolution by DNA shuffling," Trends in Biotechnol., 16:76-82 [1998].
Harvey, P.J., et al., Veratryl alcohol as a mediator and the role of radical cations in lignin biodegradation by Phanerochaete chrysosporium, FEBS Lett., 195(1,2):242-246 [1986].
Henriksen, A.L.S., et al., "Study of the glucoamylase promoter in Aspergilllus niger using green fluorescent protein," Microbiol., 145:729-34 [1999].
Inui, M., et al., "Advanced Fermentation Technologies" in Biomass to Biofuels: Strategies for Global Industries, John Wiley & Sons, Ltd., Hoboken, NJ, pp. 311-330 (Chapter 15) [2010].
Jorgensen, H., "Effect of Nutrients on Fermentation of Pretreated Wheat Straw at very High Dry Matter Content by *Saccharomyces cerevisiae*," Appl. Biochem. Biotechnol., 153:44-57 [2009].
Kramer, B., et al., "Different base/base mismatches are corrected with different efficiencies by the methyl-directed DNA mismatch-repair system of *E. coli*," Cell, 38:879-887 [1984].
Li, M.Z., et al., "Harnessing homologous recombination in vitro to generate recombinant DNA via SLIC," Nature Methods, 4:251-56 (2007).
Limon, C., et al., "Primary structure and expression pattern of the 33-kDa chitinase gene from the nucoparasitic fungus *Trichocherma harzianum*," Curr. Genet., 28:478-83 [1995].
Ling, M.M., et al., "Approaches to DNA Mutagenesis: An Overview," Anal. Biochem., 254(2):157-78 [1997].
Lynd, L.H., et al., "Microbial Cellulose Utilization: Fundamentals and Biotechnology," Microbiology and Molecular Biology Review, 66(3):506-577 [2002].
McInerney, J.O., "GCUA: general codon usage analysis," Bioinformatics, 14(4):372-73, 1998.

(56) References Cited

OTHER PUBLICATIONS

Minshull, J., et al., "Protein evolution by molecular breeding," Curr. Op. Chem. Biol., 3:284-290 [1999].

Nunberg, J.H., et al., "Molecular Cloning and Characterization of the Glucoamylase Gene of Aspergillus awamori," Mol. Cell Biol., 4(11):2306-2315 (1984).

Park, J.B., et al., "The human glutaredoxin gene: determination of its organization, transcription start point, and promoter analysis," Gene, 197: 189-93 [1997].

Patten, P.A., et al., "Applications of DNA shuffling to pharmaceuticals and vaccines," Curr. Opin. Biotechnol., 8:724-733 [1997].

Romanos, M.A., et al., "Foreign gene expression in yeast: a review," Yeast 8:423-488 [1992].

Rosgaard, L., et al., "Efficiency of New Fungal Cellulase Systems in Boosting Enzymatic Degradation of Barley Straw Lignocellulose," Biotechnol. Prog., 22:493-8 [2006].

Saloheimo, M., et al, "Swollenin, a Trichoderma reesei protein with sequence similarity to the plant expansins, exhibits disruption activity on cellulosic materials," Eur. J. Biochem., 269:4202-4211 [2002].

Simonen, M., et al, "Protein Secretion in *Bacillus* Species," Microbiological Reviews, 57:109-137 (1993).

Smith M., "In Vitro Mutagenesis," Ann. Rev. Genet., 19:423-462 [1985].

Stemmer, W.P.C., "DNA shuffling by random fragmentation and reassembly: In vitro recombination for molecular evolution," Proc. Nat. Acad. Sci. USA, 91:10747-10751 [1994].

Stemmer, W.P.C., "Rapid evolution of a protein in vitro by DNA shuffling," Nature, 370:389-391 [1994].

SwissProt Accession No. P00724 dated Feb. 5, 2015.

Taussig, R, et al., "Nucleotide sequence of the yeast SUC2 gene for invertase," Nucl. Acids Res., 11(6):1943-54 [1983].

UniProt Accession No. Q2GWR1 dated Feb. 5, 2015.

Verduyn, C., et al., "Effect of benzoic acid on metabolic fluxes in yeasts: a continuous-culture study on the regulation of respiration and alcoholic fermentation," Yeast, 8:501—517 [1992].

Viikari, L., et al., "Thermostable enzymes in lignocellulose hydrolysis," Adv. Biochem. Eng. Biotechnol., 108:121-45 [2007].

Weil, J., et al., "Pretreatment of Yellow Poplar Sawdust by Pressure Cooking in Water," Appl. Biochem. Biotechnol., 68(1-2): 21-40 [1997].

Wells, J.A., et al., "Cassette mutagenesis: an efficient method for generation of multiple mutations at defined sites," Gene, 34:315-323 [1985].

Wright, A., et al., "Diverse Plasmid DNA Vectors by Directed Molecular Evolution of Cytomegalovirus Promoters," Hum. Gene Ther., 16:881-892 [2005].

Zhang, J.-H., et al., "Directed evolution of a fucosidase from a galactosidase by DNA shuffling and screening" Proc. Nat. Acad. Sci. U.S.A., 94:4504-4509 [1997].

Zhao, X.Q.,et al., "Impact of zinc supplementation on the improvement of ethanol tolerance and yield of self-flocculating yeast in continuous ethanol fermentation" J. Biotechnol., 139:55-60 [2009].

Zhu, T., et al., "Construction of two Gateway vectors for gene expression in fungi," Plasmid, 62:128-33 [2009].

\* cited by examiner

- ◆ 50% (CBH1a+CBH2b) + 50% CH61f
- ▲ 50% (CBH1a+CBH2b) + 25% each of (GH61f and GH61p)
- ✱ Broth from CF-402 Cells (control)
- ■ 50% (CBH1a+CBH2b) + 50% CH61p
- ✶ 50% (CBH1a+CBH2b) + 16.7% each of (GH61f, GH61p, GH61a)

US 9,493,802 B2

USE OF GLYCOHYDROLASE 61 PROTEIN VARIANTS WITH IMPROVED THERMOSTABILITY FOR PROCESSING CELLULOSE

CROSS-REFERENCE TO RELATED APPLICATIONS

This application is the U.S. National Stage entry of PCT/US2011/048700, filed Aug. 22, 2011, published as WO/2012/024698 on Feb. 23, 2012. This application is also a continuation of U.S. patent application Ser. No. 13/215,193, filed Aug. 22, 2011, now U.S. Pat. No. 8,298,795. This patent disclosure claims the priority benefit of U.S. Provisional Patent Application No. 61/375,788, filed Aug. 20, 2010. The three aforelisted applications are hereby incorporated herein by reference in their entirety for all purposes.

FIELD OF THE INVENTION

The invention relates generally to the field of glycolytic enzymes and their use. More specifically, it provides GH61 proteins from *Myceliophtora thermophila*, and the use of such proteins in production of fermentable sugars and ethanol from cellulosic biomass.

BACKGROUND

Cellulosic biomass is a significant renewable resource for the generation of fermentable sugars. These sugars can be used as substrates for fermentation and other metabolic processes to produce biofuels, chemical compounds and other commercially valuable end-products. While the fermentation of sugars such as glucose to ethanol is relatively straightforward, efficient conversion of cellulosic biomass to fermentable sugars is challenging. Ladisch et al., 1983, *Enzyme Microb. Technol.* 5:82.

The conversion of cellulosic biomass to fermentable sugars may begin with chemical, mechanical, enzymatic or other pretreatments to increase the susceptibility of cellulose to hydrolysis. Such pretreatment may be followed by the enzymatic conversion of cellulose to cellobiose, cello-oligosaccharides, glucose, and other sugars and sugar polymers, using enzymes that break down cellulose. These enzymes are collectively referred to as "cellulases" and include endoglucanases, β-glucosidases and cellobiohydrolases.

SUMMARY OF THE INVENTION

In one aspect, the invention provides recombinant Glycoside Hydrolase 61 Family (GH61) proteins obtained from *Myceliophtora thermophila*, and nucleic acids that encode such proteins. The invention also provides isolated and purified GH61 proteins from *M. thermophila* culture broth. These proteins can be used to increase yield of products from reactions in which a cellulose-containing substrate undergoes saccharification by one or a combination of cellulase enzymes, such as endoglucanases, β-glucosidases, and cellobiohydrolases. The addition or presence of recombinant or isolated GH61 protein may increase yield of product from cellulase enzymes by, for example, at least 20%, 30%, 50%, 70%, 2-fold, 3-fold or more.

One embodiment of the invention is a composition comprising an isolated or recombinant GH61 protein, and a method for preparing such a composition. The protein may be isolated from *M. thermophila*, or it may be obtained by recombinant production. Amino acid sequences of twenty-four full-length *M. thermophila* GH61 proteins are provided. The GH61 proteins of this invention include proteins that comprise an amino acid sequence that is at least about 60%, about 70%, about 80%, about 85%, about 90%, about 92%, about 93%, about 94%, about 95%, about 96%, about 97% about 98% or about 99% identical to any one of the listed proteins (SEQ ID NOS:1-30) or a biologically active fragment thereof. An exemplary GH61 protein is GH61a (SEQ ID NO:2). Other exemplary GH61 proteins include GH61o, GH61v, GH61x, GH61b, and GH61e (SEQ ID NOs:6, 13, 15, 16, 19, 30). Other exemplary GH61 proteins include GH61f, GH61v, GH61p, GH61g, and GH61i (SEQ ID NOs:7, 13, 20, 21, 23, 26).

In one aspect the composition prepared according to the method of this invention comprises an isolated or recombinant GH61 protein and one or more cellulase enzymes listed in this disclosure, including but not limited to cellulase enzymes selected from endoglucanases (EG), β-glucosidases (BGL), Type 1 cellobiohydrolases (CBH1), and Type 2 cellobiohydrolases (CBH2). The GH61 protein and cellulase enzymes may be obtained from the same or different host cell types.

Another embodiment of the invention is a method for producing a fermentable sugar from a cellulosic substrate. A slurry comprising the substrate is contacted with a composition comprising a GH61 protein so as to produce fermentable sugars such as glucose and xylose from the substrate. The composition may also contain one or more enzymes selected from cellulase proteins (endoglucanases, β-glucosidases, Type 1 cellobiohydrolases, and Type 2 cellobiohydrolases), esterases, xylanases, hemicellulases, lipases, proteases, amylases, and glucoamylases. The substrate may be derived from, for example, wheat, wheat straw, sorghum, corn, rice, barley, sugar cane bagasse, grasses, switchgrass, corn grain, corn cobs, corn fiber, or a combination thereof, exemplified by pretreated wheat straw.

The fermentable sugar can be recovered and used to produce an end product such as an alcohol (such as ethanol or butanol), a sugar alcohol (such as sorbitol), an organic acid (such as lactic acid, acrylic acid, acetic acid, succinic acid, glutamic acid, citric acid, or propionic acid), an amino acid (such as glycine, lysine, or asparatic acid, an organic acid, an alkane, an alkene, a diol, or glycerol.

Another embodiment of the invention is a method for increasing yield of fermentable sugars in a saccharification reaction by one or more cellulase enzymes, by conducting the reaction in the presence of a GH61 protein as referred to above.

In another aspect, the invention provides is a method of hydrolyzing a cellulose substrate. The substrate is contacted with a composition comprising one or more recombinant GH61 proteins, one or more β-glucosidases (BGL), and one or more cellobiohydrolases (CBH). In some embodiments, the enzyme composition is substantially free of endoglucanase (EG). The hydrolyzing may result in a glucose yield that is at least 20%, 30%, 50%, 70%, 2-fold, 3-fold or more than the yield of the same reaction conducted in the absence of said GH61 protein.

Another embodiment of the invention is a method of producing an end product from a cellulosic substrate. The substrate is contacted with a composition containing GH61 protein as already referred to under conditions whereby fermentable sugars are produced. The fermentable sugars are then contacted with a microorganism in a fermentation to produce an end product such as those listed above. This method is suitable for preparing an alcohol, particularly ethanol, wherein the microorganism is a yeast.

Other embodiments of the invention include: a) the recombinant GH61 proteins already referred to, optionally produced with a heterologous signal peptide; b) a nucleic acid sequence encoding the GH61 protein which may be operably linked to a heterologous promoter; c) a host cell producing such recombinant GH61 proteins, exemplified by *M. thermophila*, yeast, a *Chaetomium*, a *Thielavia*, an *Acremonium*, a *Myceliophthora*, an *Aspergillus*, or a *Trichoderma* host cell.

The invention further embodies the use of a recombinantly produced GH61 protein in the production of ethanol. The GH61 protein comprises an amino acid sequence that is at least 60%, about 70%, about 80%, about 85%, about 90%, about 92%, about 93%, about 94%, about 95%, about 96%, about 97% about 98% or about 99% identical to any one of the listed proteins or a fragment thereof having GH61 activity.

In a related aspect, the invention provides a nucleic acid encoding a GH61 protein. The invention also provides a cell containing a recombinant nucleic acid sequence encoding a protein sequence of this invention (SEQ ID NOs:1 to 30) operably-linked to a heterologous promoter. Host cells may be (for example) *M. thermophila* cells or yeast cells. In one embodiment, the recombinant nucleic acid sequence includes SEQ ID NO:31; or any one of SEQ ID NOs:32 to 59. The cell may also express at least one recombinant cellulase protein selected from an endoglucanase (EG), a β-glucosidase (BGL), a Type 1 cellobiohydrolase (CBH1), and/or a Type 2 cellobiohydrolase (CBH2). In one embodiment, the cell expresses the GH61 protein and at least one, at least two, or at least three recombinant cellulase proteins selected from an endoglucanase (EG), a 3-glucosidase (BGL1), a Type 1 cellobiohydrolase (CBH1), and/or a Type 2 cellobiohydrolase (CBH2), and/or variants of said cellulase proteins.

In an aspect, the invention provides a composition containing a GH61 protein (e.g., SEQ ID NO:2), an endoglucanase (EG), a β-glucosidase (BGL), a Type 1 cellobiohydrolase (CBH1), and a Type 2 cellobiohydrolase (CBH2), where the combined mass of the GH61 protein, EG, BGL, CBH1 and CBH2 is at least about 20%, 40%, 60%, 70%, 80%, 90%, 95%, or substantially all of the total cell-free protein in the composition. One, two, three, or all four of the CBH1, CBH2, EG and BGL enzymes that may be present in the composition can be variants derived from naturally occurring cellulase proteins. The composition may also be a cell culture broth containing cellulase proteins.

In one aspect, the invention provides a GH61 protein comprising any of SEQ ID NOs:3 to 30 or a secreted fragment thereof. Optionally, the protein comprises the secreted fragment and the corresponding signal peptide sequence, if present. In a related aspect the invention provides a GH61 protein variant with at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to a polypeptide or biologically fragment provided herein.

In one aspect, the invention provides a recombinant nucleic acid sequence encoding a protein described above, which may have the sequence of the naturally occurring gene or fragment thereof. In one embodiment, the protein-encoding sequence of the nucleic acid is operably linked to a heterologous signal sequence. Typically, the recombinant nucleic acid sequence is operably linked to a heterologous promoter. In one aspect, the invention provides a host cell containing a recombinant nucleic acid of the invention. The cell may express at least one, two, three or four recombinant cellulase proteins selected from endoglucanases (EG), β-glucosidases (BGL), Type 1 cellobiohydrolases (CBH1), and/or Type 2 cellobiohydrolases (CBH2).

In one aspect, the invention provides a composition containing at least one isolated protein comprising a sequence selected from the secreted portion of SEQ ID NOs:1 to 30, and or at least one biologically active fragment thereof. In one embodiment, the composition also contains at least one endoglucanase (EG), β-glucosidase (BGL), Type 1 cellobiohydrolase (CBH1), and/or Type 2 cellobiohydrolase (CBH2), where the combined mass of the GH61 protein, EG, BGL, CBH1 and/or CBH2 is at least about 70% of the total cell-free protein in the composition.

In an aspect, the invention provides methods for saccharification by (a) culturing a cell of the invention under conditions in which at least one GH61 protein is secreted into the culture broth, and (b) combining the broth and a cellulosic biomass under conditions in which saccharification occurs, where (a) may take place before or simultaneously with (b).

In one aspect, the invention provides a method of hydrolyzing a starch, comprising contacting the starch with a composition comprising one or more recombinant GH61 proteins and one or more amylase(s).

Other embodiments of the invention will be apparent from the description that follows.

DESCRIPTION OF THE DRAWINGS

FIG. 1 is taken from an experiment using recombinantly produced GH61a protein from *Myceliophtora thermophila*. The protein was tested for cellulase enhancing activity using cellulase enzymes from a culture broth of *M. thermophila*. FIG. 1(A) shows the percentage of improved yield from a saccharification reaction conducted in the presence of GH61a, compared with the same reaction in the absence of GH61a.

DETAILED DESCRIPTION

I. Introduction

Figure 1A:
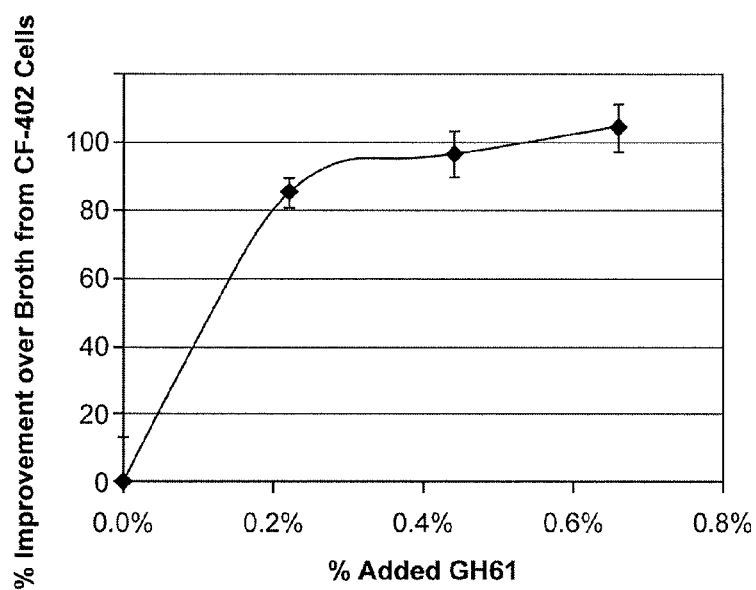

It was determined that the filamentous fungus *Myceliophthora thermophila* produces GH61 proteins. GH61 proteins increase yield of fermentable sugars when a cellulose-containing substrate undergoes saccharification by one or more cellulase enzymes. Fermentable sugars produced by saccharification may be used, among other uses, in fermentation reactions to produce end-products, such as, but not limited to ethanol.

GH61 proteins can be isolated from *M. thermophila* cells. GH61 proteins can also be produced recombinantly by expressing a nucleic acid that encodes any of the GH61 protein sequences provided in this disclosure, including wild-type sequences and variants and fragments of wild-type sequences.

Preparation and use of GH61 proteins and compositions of this invention are described in more detail in the sections that follow.

II. Definitions

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, a "GH61 protein" is a protein with GH61 (or "cellulase enhancing") activity. A "GH61 protein" or GH61 polypeptide may have a sequence of a naturally occurring (wild-type) protein or may comprise variations relative to a wild-type protein.

As used herein the GH61 protein sequences shown in Tables 1 and 2 (SEQ ID NOS:1-30) are considered wild-type sequences.

A protein has "GH61 activity" or "cellulase enhancing activity" or is "biologically active" if, when included in a saccharification reaction (e.g., carried out using an endoglucanase, a β-glucosidase and Type 1 and Type 2 cellobiohydrolases) results in a greater amount (i.e., greater yield) of one or more soluble sugars (e.g., glucose) than the saccharification reaction carried out under the same conditions in the absence of the GH61 protein. A "biologically active variant" is a variant or fragment that retains at least some (e.g., at least 10%) of the GH61 activity of the wild-type protein.

As used herein, a "variant" GH61 protein (or polynucleotide encoding a GH61 protein) is a GH61 protein comprising one or more modifications relative to wild-type GH61 (or the wild-type polynucleotide encoding GH61). Modifications include substitutions, insertions, deletions, and/or amino or carboxy truncations of one or more amino acid residues (or of one or more nucleotides or codons in the polynucleotide). A variant comprising a deletion relative to wild-type protein may be referred to as a "fragment."

As used herein, a "fragment" of a GH61 protein is (a) a polypeptide with a wild-type sequence but comprising a deletion relative to SEQ ID NOS:1-30 or (b) a GH61 variant comprising a deletion relative to a polypeptide of SEQ ID NOS:1-30.

An amino acid "substitution" in a protein sequence is replacement of a single amino acid within that sequence with another amino acid.

An amino acid substitution may be a "conservative" substitution, in which case the substituted amino acid that shares one or more chemical property with the amino acid it is replacing. Shared properties include the following: Basic amino acids: arginine (R), lysine (K), histidine (H); acidic amino acids: glutamic acid (E) and aspartic acid (D); uncharged polar amino acids: glutamine (Q) and asparagine (N); hydrophobic amino acids: leucine (L), isoleucine (I), valine (V); aromatic amino acids: phenylalanine (F), tryptophan (W), and tyrosine (Y); sulphur-containing amino acids: cysteine (C), methionine (M); small amino acids: glycine (G), alanine (A), serine (S), threonine (T), proline (P), cysteine (C), and methionine (M).

The term "pre-protein" has its standard meaning in the art and refers to a polypeptide including an amino-terminal signal peptide (or leader sequence) region attached. The signal peptide is cleaved from the pre-protein by a signal peptidase concomitant with secretion of the protein. The secreted portion of the protein may be referred to as the "mature" protein or "secreted" protein. Thus, an amino acid sequence of a pre-protein, the sequence will comprise a signal peptide portion and a secreted (mature) portion.

As used herein the term "signal peptide" has its usual meaning in the art and refers to a amino acid sequence linked to the amino terminus of a polypeptide, which directs the encoded polypeptide into a cell's secretory pathway.

"Saccharification" refers to an enzyme-catalyzed reaction that results in hydrolysis of a complex carbohydrate to fermentable sugar(s) (e.g., monosaccharides such as glucose or xylose). The enzymes may be cellulase enzyme(s) such as endoglucanases, β-glucosidases, Type 1 and/or Type 2 cellobiohydrolases, and combinations of such cellulase enzymes. The cellulase enzymes may be from a culture broth from a wild-type or cellulase-engineered organism that produces cellulase enzymes (e.g., a fungus such as *M. thermophila* or yeast).

"Hydrolyzing" cellulose or another polysaccharide (e.g., starch) occurs when glycosidic bonds between at least some of the adjacent monosaccharides are hydrolyzed, thereby separating previously bonded monomer pairs from each other.

"Increasing" yield of a product (such as a fermentable sugar) from a reaction occurs when a particular component present during the reaction (such as a GH61 protein) causes more product to be produced, compared with a reaction conducted under the same conditions with the same substrate and other substituents, but in the absence of the component of interest.

The terms "improved" or "improved properties," as used in the context of describing the properties of a GH61 variant, refers to a GH61 variant polypeptide that exhibits an improvement in a property or properties as compared to the wild-type GH61 (e.g., SEQ ID NO:2) or a specified reference polypeptide. Improved properties may include, but are not limited to increased protein expression, increased thermoactivity, increased thermostability, increased pH activity, increased stability (e.g., increased pH stability), increased product specificity, increased specific activity, increased substrate specificity, increased resistance to substrate or end-product inhibition, increased chemical stability, reduced inhibition by glucose, increased resistance to inhibitors (e.g., acetic acid, lectins, tannic acids, and phenolic compounds), and altered pH/temperature profile.

The term "cellulase" (or "cellulase enzyme") broadly refers to enzymes that catalyze the hydrolysis of cellulose β-1,4-glycosidic linkages to shorter cellulose chains, oligosaccharides, cellobiose and/or glucose, e.g., endoglucanases, β-glucosidases, and cellobiohydrolases.

As used herein, the term "polynucleotide" refers to a polymer of deoxyribonucleotides or ribonucleotides in either single- or double-stranded form, and complements thereof.

As used herein, a "gene" is a nucleic acid sequence that encodes a protein. The nucleic acid may or may not have any introns, may or may not be recombinant, and may or may not further comprise elements that affect transcription or translation. For purposes of this description, a cDNA sequence encoding a protein can sometimes be referred to as a "gene".

The term "recombinant nucleic acid" has its conventional meaning. A recombinant nucleic acid, or equivalently, "polynucleotide," is one that is inserted into a heterologous location such that it is not associated with nucleotide sequences that normally flank the nucleic acid as it is found in nature (for example, a nucleic acid inserted into a vector or a genome of a heterologous organism). Likewise, a nucleic acid sequence that does not appear in nature, for example a variant of a naturally occurring gene, is recombinant. A cell containing a recombinant nucleic acid, or protein expressed in vitro or in vivo from a recombinant nucleic acid are also "recombinant." Examples of recombinant nucleic acids include a protein-encoding DNA sequence that is (i) operably linked to a heterologous promoter and/or (ii) encodes a fusion polypeptide with a protein sequence and a heterologous signal peptide sequence.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS 50° C. (low stringency), at 55° C. (medium stringency), at 60° C. (medium-high stringency), at 65° C. (high stringency), or at 70° C. (very high stringency).

The term "expression vector" refers to a DNA molecule, linear or circular, that comprises a segment encoding a polypeptide of the invention, and which is operably linked to additional segments that provide for its transcription (e.g., a promoter, a transcription terminator sequence, enhancers) and optionally a selectable marker.

For purposes of this disclosure, a promoter is "heterologous" to a gene sequence if the promoter is not associated in nature with the gene. A signal peptide is "heterologous" to a protein sequence when the signal peptide sequence is not associated with the protein in nature.

In relation to regulatory sequences (e.g., promoters), the term "operably linked" refers to a configuration in which a regulatory sequence is located at a position relative to a polypeptide encoding sequence such that the regulatory sequence influences the expression of the polypeptide. In relation to a signal sequence, the term "operably linked" refers to a configuration in which the signal sequence encodes an amino-terminal signal peptide fused to the polypeptide, such that expression of the gene produces a pre-protein.

As used herein, the terms "peptide," "polypeptide," and "protein" are used interchangeably herein to refer to a polymer of amino acid residues.

As used herein, the term "amino acid" refers to naturally occurring and synthetic amino acids, as well as amino acid analogs.

The terms "biomass," "biomass substrate," "cellulosic biomass," "cellulosic feedstock," "lignocellulosic feedstock" and "cellulosic substrate," all refer to materials that contain cellulose. For simplicity the term "cellulosic substrate" is used herein to refer to cellulose-containing materials that can be acted on by cellulases (with GH61 proteins optionally present), typically after pretreatment, to produce fermentable sugars. Examples of cellulosic substrates include, but are not limited to, biomass such as wood, wood pulp, paper pulp, corn fiber, corn grain, corn cobs, crop residues such as corn husks, corn stover, grasses, wheat, wheat straw, barley, barley straw, hay, rice straw, switchgrass, waste paper, paper and pulp processing waste, woody or herbaceous plants, fruit or vegetable pulp, distillers grain, rice hulls, cotton, hemp, flax, sisal, sugar cane bagasse, sorghum, soy, components obtained from milling of grains, trees, branches, roots, leaves, wood chips, sawdust, shrubs and bushes, vegetables, fruits, and flowers and mixtures thereof. In some embodiments, the cellulosic material is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis. Cellulosic substrates and their processing are described in greater detail hereinbelow.

A cellulosic substrate is "derived from" a specific source (such as corn or wheat) by a process that comprises obtaining the source or a physical part of the source (such as a corn cob or wheat straw), and then optionally pretreating the source or part.

A cellulase protein sequence (i.e., a cellulose variant) is "derived from" a wild-type cellulase sequence when it is produced by introducing variations into a wild-type sequence using in vitro mutageneisis or molecular evolution methods. Typically the protein sequence will be at least 70% about 75%, about 80%, about 85%, about 90%, about 91%, about 92%, about 93%, about 94%, about 95% to the wild-type sequence.

A cellulosic substrate is said to be "pretreated" when it has been processed by some physical and/or chemical means to facilitate saccharification.

"Fermentable sugars" refers to simple sugars (monosaccharides, disaccharides and short oligosaccharides) such as but not limited to glucose, xylose, galactose, arabinose, mannose and sucrose. Fermentable sugar is any sugar that a microorganism can utilize or ferment.

The terms "transform" or "transformation," as used in reference to a cell, means a cell has a non-native nucleic acid sequence integrated into its genome or as an episome (e.g., plasmid) that is maintained through multiple generations.

The term "introduced," as used in the context of inserting a nucleic acid sequence into a cell, means conjugated, transfected, transduced or transformed (collectively "transformed") or otherwise incorporated into the genome of, or maintained as an episome in, the cell.

A "cellulase-engineered" cell is a cell comprising at least one, at least two, at least three, or at least four recombinant sequences encoding a cellulase or cellulase variant, and in which expression of the cellulase(s) or cellulase variant(s) has been modified relative to the wild-type form. Expression of a cellulase is "modified" when a non-naturally occurring cellulase variant is expressed or when a naturally occurring cellulase is over-expressed. One way to over-express a cellulase is to operably link a strong (optionally constitutive) promoter to the cellulase encoding sequence. Another way to over-express a cellulase is to increase the copy number of a heterologous, variant, or endogenous cellulase gene. The cellulase-engineered cell may be a fungal cell, such as a yeast cell or a filamentous fungal cell (e.g., *Acidothermus cellulolyticus, Thermobifida fusca, Humicola grisea, Myceliophthora thermophila, Chaetomium thermophilum, Acremonium* sp., *Thielavia* sp, *Trichoderma reesei, Aspergillus* sp.). In some embodiments the cellulase-engineered cell is a *M. thermophila* cell.

The term "culturing" refers to growing a population of microbial (e.g., fungal) cells under in a liquid or solid culture medium. Some cultured cells express and secrete proteins, such as for example, GH61 proteins or cellulase proteins. When cells are grown in a liquid medium proteins may be secreted into the medium, which is referred to by various terms, including cell culture medium, cell culture supernatant, and cell broth.

As used herein, the term "recovering" refers to the harvesting, isolating, collecting or separating a protein, sugar, cell or end product (e.g., alcohol) from a cell broth or, alternatively, solid culture medium.

As used herein, the term "isolated" refers to a nucleic acid, polypeptide, or other component that is partially or completely separated from components with which it is normally associated in nature (such as other proteins, nucleic acids, or cells).

A product that has been "purified" is a product that has been enriched from the source from which it is obtained by at least 10-fold, and optionally by at least 100-fold, or at least 1000-fold. For example, a protein that is obtained from a culture broth in which it represents 0.1% of the total protein may be purified so that it is 1%, 2.5%, 10%, 25%, 50%, 80%, 95% or 100% (wt/wt) of the protein in the preparation. A product that is "partly purified" has been enriched from the source from which it is produced by at least 2-fold, or least 5-fold, but still contains at least 50%, and sometimes at least 90% (wt/wt) unrelated components other than the solvent.

"Fractionating" a liquid product such as a culture broth means applying a separation process (such as salt precipitin, column chromatography, size exclusion, and filtration) or a combination of such processes so as to obtain a solution in which a desired protein (such as a GH61 protein, a cellulase enzyme, or a combination thereof) is a greater percentage of total protein in the solution than in the initial liquid product.

A "slurry" is an aqueous solution in which are dispersed one or more solid components, such as a cellulosic substrate.

As used herein a "composition" comprising one or more proteins may be, for example, a cell free composition comprising the protein(s), a cell lysate, a cell broth comprising the protein(s), e.g., in secreted form; a cell comprising the protein(s), such as a recombinant cell expressing the protein(s); a mixture of two or more cell populations that express different proteins (e.g., one cell expressing a recombinant GH61 protein and a second cell expressing cellulase protein).

The term "cell-free composition" refers to a protein-containing composition in which cells and cellular debris have been removed, such as a purified cellulase mixture or a cell-incubation broth containing secreted protein, from which cells and insoluble material have been removed.

The terms "percent identity," "% identity", "percent identical", and "% identical" are used interchangeably to refer to a comparison of two optimally aligned sequences over a comparison window. The comparison window may include additions or deletions in either sequence to optimize alignment. The percentage of identity is the number of positions that are identical between the sequences, divided by the total number of positions in the comparison window (including positions where one of the sequences has a gap). For example, a protein with an amino acid sequence that matches at 310 positions a sequence of GH61a (which has 323 amino acids in the secreted form), would have 310/323=95.9% identity to the reference. Similarly, a protein variant that has 300 residues (i.e., less than full-length) and matches the reference sequence at 280 positions would have 280/300=93.3% identity. While optimal alignment and scoring can be accomplished manually, the process can be facilitated by using a computer-implemented alignment algorithm. Examples are the BLAST and BLAST 2.0 algorithms, described in Altschul et al., 1990, *J. Mol. Biol.* 215: 403-410 and Altschul et al., 1977, *Nucleic Acids Res.* 3389-3402. Alternatively, the degree of identity between two amino acid sequences can be determined using the Needleman-Wunsch algorithm (Needleman and Wunsch, 1970, *J. Mol. Biol.* 48: 443-53), which has been implemented in the Needle program of the EMBOSS package (EMBOSS: The European Molecular Biology Open Software Suite, Rice et al., 2000, *Trends in Genetics* 16: 276-77), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity"

(obtained using the -nobrief option) is used as the percent identity and is calculated as follows: (Identical Residues× 100)÷(Length of Alignment−Total Number of Gaps in Alignment).

III. Identification of GH61 Genes

Twenty four GH61 proteins endogenous to *Myceliophthora thermophila* were identified as described in Example 1. See TABLE 1 and TABLE 2 below. As shown in the Examples 2 and 3, a particular *M. thermophila* GH61 protein with the designation GH61a (SEQ ID NO:2) was shown to enhance saccharification reactions in the presence of cellulases. Similarly, other GH61 proteins of this invention (SEQ ID NOs:3 to 30) may be used to enhance cellulase activity.

TABLE 1 provides the sequence of a GH61 pre-protein (SEQ ID NO:1), showing the predicted native signal peptide underlined, and the predicted secreted (mature) form (SEQ ID NO:2). Sequence ID NO:2 is 323 amino acids in length. It is contemplated that certain GH61a protein variants of the invention will comprise residues 11-323 of SEQ ID NO:2 (including, but not limited to, amino-terminal truncated fragments), or will have at least: about 70%, about 75%, about 80%, about 85%, about 90%, about 91%, about 92%, about 93%, about 94%, about 95%, about 96%, about 97%, about 98%, or about 99% sequence identity to residues 11-323 of SEQ ID NO:2. In some embodiments the GH61s protein variant will have at least 90% identity to residues 11-323 of SEQ ID NO:2 and will be at least 315 residues long.

TABLE 2 provides 28 GH61 pre-protein sequences, with the predicted native signal peptide underlined. GH61t and GH61n are not predicted to have signal peptides. Except where otherwise specified or clear from context, reference to one or more sequences listed in TABLE 2 is intended to encompass either or both of the pre-protein form and secreted form (i.e., a protein comprising the entire sequence, and a protein not including the underlined sequence). It is also contemplated that that certain GH61 proteins of the invention will comprise residues 11 to the C-terminus of the sequences shown in Table 2 (including, but not limited to, amino-terminal truncated fragments), or will have at least: about 70%, about 75%, about 80%, about 85%, about 90%, about 91%, about 92%, about 93%, about 94%, about 95%, about 96%, about 97%, about 98%, or about 99% sequence identity to residues 11 to C-terminus of these sequences. In Table 2 the following designations may be used: B=SEQ ID NO. of full length protein (including signal peptide); C=Signal Peptide (Underlined); D=Mature Protein (Not Underlined); E=Portion of D commencing at residue 11 of the secreted portion (i.e., between the last gap and the C-terminus, an amino terminal truncated portion).

Signal peptide boundaries in TABLE 1 and TABLE 2 are predicted based on analysis of the primary sequence. It is possible that the actual cleavage site differs by from the predicted site by up to several residues (e.g., 1-10, e.g., up to 1, 2, 3, 4, 5, 6, 7, 8, 9 or 10). The presence of a heterologous signal peptide can also affect the cleavage site. A signal peptide cleavage site can be determined by expressing the full-length sequence, and identifying the amino terminal residues of the secreted GH61 protein. Addition or deletion of several residues at the amino terminus of the mature protein is expected to may have little or no effect on the activity of the secreted protein.

TABLE 1

Glycoside Hydrolase 61 protein GH61a

| SEQ. ID NO: | Designation | |
|---|---|---|
| 1 | GH61a | Pre-Protein:<br>MSKASALLAGLTGAALVAA HGHVSHIVVN GVYYRNYDPTTDWYQPNPPTVIGWTAADQDN GFVEPNSFGTPDIICHKSATPGGGHATVAAGDKINIVWTPEWPESHIGPVIDYLAACNGDCE TVDKSSLRWFKIDGAGYDKAAGRWAADALRANGNSWLVQIPSDLKAGNYVLRHEIIALHGAQ SPNGAQAYPQCINLRVTGGGSNLPSGVAGTSLYKATDPGILFNPYVSSPDYTVPGPALIAGA ASSIAQSTSVATATGTATVPGGGGANPTATTTAATSAAPSTTLRIIIISAAQTTAPPSGDVQ TKYGQCGGNGWTGPTVCAPGSSCSVLNEWYSQCL |
| 2 | GH61a | Mature Protein:<br>HGHVSHIVVN GVYYRNYDPTTDWYQPNPPTVIGWTAADQDNGFVEPNSFGTPDIICHKSAT PGGGHATVAAGDKINIVWTPEWPESHIGPVIDYLAACNGDCETVDKSSLRWFKIDGAGYDKA AGRWAADALRANGNSWLVQIPSDLKAGNYVLRHEIIALHGAQSPNGAQAYPQCINLRVTGGG SNLPSGVAGTSLYKATDPGILFNPYVSSPDYTVPGPALIAGAASSIAQSTSVATATGTATVP GGGGANPTATTTAATSAAPSTTLRTITTSAAQTTAPPSGDVQTKYGQCGGNGWTGPTVCAPG SSCSVLNEWYSQCL |

TABLE 2

Glycoside Hydrolase 61 Proteins

| B | Designation | Sequence (Putative Signal Peptide Sequence is Underlined) |
|---|---|---|
| 3 | GH61l | MFSLKFFILAGGLAVLTEA HIRLVSPAPF TNPDQGPSPLLEAGSDYPCHNGNGGGYQGT PTQMAKGSKQQLAFQGSAVHGGGSCQVSITYDENPTAQSSFKVIHSIQGGCPARAETIPDC SAQNINACNIKPDNAQMDTPDKYEFTIPEDLPSGKATLAWTWINTIGNREFYMACAPVEIT GDGGSESALAALPDMVIANIPSIGGTCATEEGKYVEYPNPGKSVETIPGWTDLVPLQGECG AASGVSGSGGNASSATPAAGAAPTPAVRGRRPTWNA |

TABLE 2 -continued

Glycoside Hydrolase 61 Proteins

| B | Desig-nation | Sequence (Putative Signal Peptide Sequence is Underlined) |
|---|---|---|
| 4 | GH61m | MKLATLLAALTLGVA DQLSVGSRKFG VYEHIRKNTNYNSPVTDLSDTNLRCNVGGGSGT STTVLDVKAGDSFTFFSDVAVYHQGPISLCVDRTSAESMDGREPDMRCRTGSQAGYLAVTD YDGSGDCFKIYDWGPTFNGGQASWPTRNSYEYSILKCIRDGEYLLRIQSLAIHNPGALPQF YISCAQVNVTGGGTVTPRSRRPILIYFNFHSYIVPGPAVFKC |
| 5 | GH61n | MTKNAQSKQG VENPTSGDIRCYTSQTAANVVTVPAGSTIHYISTQQINHPGPTQYYLAKV PPGSSAKTFDGSGAVWFKISTTMPTVDSNKQMFWPGQNTYETSNTTIPANTPDGEYLLRVK QIALHMASQPNKVQFYLACTQIKITGGRNGTPSPLVALPGAYKSTDPGILVDIYSMKPESY QPPGPPVWRG |
| 6 | GH61o | MKPFSLVALATAVSG HAIFQRVSVN GQDQGQLKGVRAPSSNSPIQNVNDANMACNANIV YHDNTIIKVPAGARVGAWWQHVIGGPQGANDPDNPIAASHKGPIQVYLAKVDNAATASPSG LKWFKVAERGLNNGVWAYLMRVELLALHSASSPGGAQFYMGCAQIEVTGSGTNSGSDFVSF PGAYSANDPGILLSIYDSSGKPNNGGRSYPIPGPRPISCSGSGGGGNNGGDGGDDNNGGGN NNGGGGSVPLYGQCGGIGYTGPTTCAQGTCKVSNEYYSQCLP |
| 7 | GH61p | MKLTSSLAVLAAAGAQA HYTFPRAGTG GSLSGEWEVVRMTENHYSHGPVTDVTSPEMTC YQSGVQGAPQTVQVKAGSQFTFSVDPSIGHPGPLQFYMAKVPSGQTAATFDGTGAVWFKIY QDGPNGLGTDSITWPSAGKTEVSVTIPSCIEDGEYLLRVEHTPLPTAPAAQNRARSSPSPA AYKATDPGILFQLYWPIPTEYINPGPAPVSC |
| 8 | GH61q | MPPPRLSTLLPLLALIAPTALG HSHLGYIIIN GEVYQGFDPRPEQANSPLRVGWSTGAI DDGFVAPANYSSPDIICHIEGASPPAHAPVRAGDRVHVQWNGWPLGHVGPVLSYLAPCGGL EGSESGCAGVDKRQLRWTKVDDSLPAMEL |
| 9 | GH61r | MRSTLAGALAAIAAQKVAG HATFQQLWHG SSCVRLPASNSPVTNVGSRDFVCNAGTRPV SGKCPVKAGGTVTIEMHQQPGDRSCNNEAIGGAHWGPVQVYLTKVQDAATADGSTGWFKIF SDSWSKKPGGNLGDDDNWGTRDLNACCGKMD |
| 10 | GH61s | MLLLTLATLVTLLARHVSA HARLFRVSVD GKDQGDGLNKYIRSPATNDPVRDLSSAAIV CNTQGSKAAPDFVRAAAGDKLTFLWAHDNPODPVDYVLDPSHKGAILTYVAAYPSGDPTGP IWSKLAEEGFTGGQWATIKMIDNGGKVDVTLPEALAPGKYLIRQELLALHRADFACDDPAH PNRGAESYPNCVQVEVSGSGDKKPDQNFDFNKGYTCDNKGLHFKIYIGQDSQYVAPGPRPW NGS |
| 11 | GH61t | MFTSLCITDH WRTLSSHSGPVMNYLAHCTNDDCKSFKGDSGNVWVKIEQLAYNPSANPPW ASDLLREHGAKWKVTIPPSLVPGEYLLRHEILGLHVAGTVMGAQFYPGCTQIRVTEGGSTQ LPSGIALPGAYGPQDEGILVDLWRVNQGQVNYTAPGGPVWSEAWDTEFGGSNTTECATMLD DLLDYMAANDEWIGWTA |
| 12 | GH61u | MKLSAAIAVLAAALAEG HYTFPSIANT ADWQYVRITTNFQSNGPVTDVNSDQIRCYERN PGTGAPGIYNVTAGTTINYNAKSSISHPGPMAFYIAKVPAGQSAATWDGKGAVWSKIHQEM PHFGTSLTWDSNGRTSMPVTIPRCLQDGEYLLRAEHIALHSAGSPGGAQFYISCAQLSVTG GSGTNNPRNKVSFPGAYKATDPGILINIYYPVPTSYTPAGPPVDTC |
| 13 | GH61v | MYRTLGSIALLAGGAAAHG AVTSYNIAGK DYPGYSGFAPTGQDVIQWQWPDYNPVLSAS DPKLRCNGGTGAALYAEAAPGDTITATWAQWTHSQGPILVWMYKCPGDFSSCDGSGAGWFK IDEAGFHGDGTTVFLDTETPSGWDIAKLVGGNKSWSSKIPDGLAPGNYLVRHELIALHQAN NPQFYPECAQIKVTGSGTAEPAASYKAAIPGYCQQSDPNISFNINDHSLPQEYKIPGPPVF KGTASAKARAFQA |
| 14 | GH61w | MLTTTFALLTAALGVSA HYTLPRVGTG SDWQHVRRADNWQNNGFVGDVNSEQIRCFQAT PAGAQDVYTQAGSTVTYHANPSIYHPGPMQFYLARVPDGQDVKSWTGEGAVWFKVYEEQP QFGAQLTWPSNGKSSFEVPIPSCIRAGNYLLRAEHIALHVAQSQGGAQFYISCAQLQVTGG GSTEPSQKVSFPGAYKSTDPGILININYPVPTSYQNPGPAVFRC |
| 15 | GH61x | MKVLAPLILAGAASA HTIFSSLEVG GVNQGIGQGVRVPSYNGPIEDVTSNSIACNGPPN PTTPTNKVITVRAGETVTAVWRYMLSTTGSAPNDIMDSSHKGPTMAYLKKVDNATTDSGVG GGWFKIQEDGLTNGVWGTERVINGQGRHNIKIPECIAPGQYLLRAEMLALHGASNYPGAQF YMECAQLNIVGGTGSKTPSTVSFPGAYKGTDPGVKINIYWPPVTSYQIPGPGVFTC |
| 16 | GH61b | MKLSLFSVLATALTVEGHA IFQKVSVNGA DQGSLTGLRAPNNNNPVQNVNSQDMICGQS GSTSNTIIEVKAGDRIGAWYQHVIGGAQFPNDPDNPIAKSHKGPVMAYLAKVDNAATASKT GLKWFKIWEDTFNPSTKTWGVDNLINNNGWVYFNLPQCIADGNYLLRVEVLALHSAYSQGQ AQFYQSCAQINVSGGGSFTPASTVSFPGAYSASDPGILINIYGATGQPDNNGQPYTAPGPA PISC |
| 17 | GH61c | MALQLLASLALLSVPALAHGGLA NYTVGDTWYR GYDPNLPPETQLNQTWMIQRQWATID PVFTVSEPYLACNNPGAPPPSYIPIRAGDKITAVYWYWLHAIGPMSVWLARCGDTPAADCR DVDVNRVGWFKIWEGGLLEGPNLAEGLWYQKDFQRWDGSPSLWPVTIPKGLKSGTYIIRHE ILSLHVALKPQFYPECAHLNITGGGDLLPPEETLVRFPGVYKEDDPSIFIDVYSEENANRT DYTVPGGPIWEG |

TABLE 2 -continued

Glycoside Hydrolase 61 Proteins

| B | Designation | Sequence (Putative Signal Peptide Sequence is Underlined) |
|---|---|---|
| 18 | GH61d | MKALSLLAAAGAVSA HTIFVQLEAD GTRYPVSYGIRDPTYDGPITDVTSNDVACNGGPN PTTPSSDVITVTAGTTVKAIWRHTLQSGPDDVMDASHKGPTLAYIKKVGDATKDSGVGGGW FKIQEDGYNNGQWGTSTVISNGGEHYIDIPACIPEGQYLLRAEMIALHAAGSPGGAQLYME CAQINIVGGSGSVPSSTVSFPGAYSPNDPGLLINIYSMSPSSSYTIPGPPVFKC |
| 19 | GH61e | MKSSTPALFAAGLLAQHAAA HSIFQQASSG STDFDTLCTRMPPNNSPVTSVTSGDMTCK VGGTKGVSGFCEVNAGDEFTVEMHAQPGDRSCANEAIGGNHFGPVLIYMSKVDDASTADGS GDWFKVDEFGYDASTKTWGTDKLNENCGKRTFNIPSHIPAGDYLVRAEAIALHTANQPGGA QFYMSCYQVRISGGEGGQLPAGVKIPGAYSANDPGILVDIWGNDFNDPPGHSARHAIIIIS SSSNNSGAKMTKKIQEPTITSVTDLPTDEAKWIALQKISYVDQTGTARTYEPASRKTRSPR V |
| 20 | GH61f | MKSFTLTTLAALAGNAAA HATFQALWVD GVDYGAQCARLPASNSPVTDVTSNAIRCNAN PSPARGKCPVKAGSTVTVEMHQQPGDRSCSSEAIGGAHYGPVMVYMSKVSDAASADGSSGW FKVFEDGWAKNPSGGSGDDDYWGTKDLNSCCGKMNVKIPADLPSGDYLLRAEALALHTAGS AGGAQFYMTCYQLTVTGSGSASPPTVSFPGAYKATDPGILVNIHAPLSGYTVPGPAVYSGG STKKAGSACTGCESTCAVGSGPTATVSQSPGSTATSAPGGGGGCTVQKYQQCGGQGYTGCT NCASGSTCSAVSPPYYSQCV |
| 21 | GH61g | MKGLLGAAALSLAVSDVSA HYIFQQLTTG GVKHAVYQYIRKNTNYNSPVTDLTSNDLRC NVGATGAGTDTVTVRAGDSFTFTTDTPVYHQGPTSIYMSKAPGSASDYDGSGGWFKIKDWA DYTATIPECIPPGDYLLRIQQLGIHNPWPAGIPQFYISCAQITVTGGGSANPGPTVSIPGA FKETDPGYTVNIYNNFHNYTVPGPAVFTCNGSGGNNGGGSNPVTTTTTTTRPSTSTAQSQ PSSSPTSPSSCTVAKWGQCGGQGYSGCTVCAAGSTCQKTNDYYSQCL |
| 22 | GH61h | MSSFTSKGLLSALMGAATVA AHGHVTNIVI NGVSYQNFDPFTHPYMQNPPTVVGWTASN TDNGFVGPESFSSPDIICHKSATNAGGHAVVAAGDKVFIQWDTWPESHHGPVIDYLADCGD AGCEKVDKTTLKFFKISESGLLDGTNAPGKWASDTLIANNNSWLVQIPPNIAPGNYVLRHE IIALHSAGQQNGAQNYPQCFNLQVTGSGTQKPSGVLGTELYKATDAGILANIYTSPVTYQI PGPAIISGASAVQQTTSAITASASAITGSATAAPTAATTTAAAATTTTTAGSGATATPST GGSPSSAQPAPTTAAATSSPARPTRCAGLKKRRRHARDVKVAL |
| 23 | GH61i | MKTLAALVVSAALVAAHG YVDHATIGGK DYQFYQPYQDPYMGDNKPDRVSRSIPGNGPV EDVNSIDLQCHAGAEPAKLHAPAAAGSTVTLYWTLWPDSHVGPVITYMARCPDTGCQDWSP GTKPVWFKIKEGGREGTSNTPLMTAPSAYTYTIPSCLKSGYYLVRHEIIALHSAWQYPGAQ FYPGCHQLQVTGGGSTVPSTNLVSFPGAYKGSDPGITYDAYKAQPYTIPGPAVFTC |
| 24 | GH61j | MRYFLQLAAAAAFAVNSAAG HYIFQQFATG GSKYPPWKYIRRNTNPDWLQNGPVTDLSS TDLRCNVGGQVSNGTETITLNAGDEFSFILDTPVYHAGPTSLYMSKAPGAVADYDGGGAWF KIYDWGPSGTSWTLSGTYTQRIPKCIPDGEYLLRIQQIGLHNPGAAPQFYISCAQVKVVDG GSTNPTPTAQIPGAFHSNDPGLTVNIYNDPLTNYVVPGPRVSHW |
| 25 | GH61k | MHPSLLFTLGLASVLVPLSSA HTTFTTLFVN DVNQGDGTCIRMAKKGNVATHPLAGGLD SEDMACGRDGQEPVAFTCPAPAGAKLTLEFRMWADASQSGSIDPSHLGVMAIYLKKVSDMK SDAAAGPGWFKIWDQGYDLAAKKWATEKLIDNNGLLSVNLPTGLPTGYYLARQEIITLQNV TNDRPEPQFYVGCAQLYVEGTSDSPIPSDKTVSIPGHISDPADPGLTFNVYTGDASTYKPP GPEVYFPTTTTTSSSSSGSSDNKGARRQQTPDDKQADGLVPADCLVKNANWCAAALPPYT DEAGCWAAAEDCNKQLDACYTSAPPSGSKGCKVWEEQVCTVVSQKCEAGDFKGPPQLGKEL GEGIDEPIPGGKLPPAVNAGENGNHGGGGGDDGDDDNEAGAGAASTPTFAAPGAAKTPQP NSERARRREAHWRRLESAE |
| 26 | GH61p2 | MKLTSSLAVLAAAGAQA HYTFPRAGTG GSLSGEWEVVRMTENHYSHGPVTDVTSPEMTC YQSGVQGAPQTVQVKAGSQFTFSVDPSIGHPGPLQFYMAKVPSGQTAATFDGTGAVWFKIY QDGPNGLGTDSITWPSAGKTEVSVTIPSCIEDGEYLLRVEHIALHSASSVGGAQFYIACAQ LSVTGGSGTLNTGSLVSLPGAYKATDPGILFQLYWPIPTEYINPGPAPVSC |
| 27 | GH61q2 | MPPPRLSTLLLPLLALIAPTALG HSHLGYIIING EVYQGFDPRPEQANSPLRVGWSTGAI DDGFVAPANYSSPDIICHIEGASPPAHAPVRAGDRVHVQWKRLAARTRGAGAVVPGALRRA GGVRERVDDSLPAMELVGAAGGAGGEDDGSGSDGSGSGGSGRVGVPGQRWATDVLIAANNS WQVEIPRGLRDGPYVLRHEIVALHYAAEPGGAQNYPLCVNLWVEGGDGSMELDHFDATQFY RPDDPGILLNVTAGLRSYAVPGPTLAAGATPVPYAQQNISSARADGTPVIVTRSTETVPFT AAPTPAETAEAKGGRYDDQTRTKDLNERFFYSSRPEQKRLTATSRRELVDHRTRYLSVAVC ADFGAHKAAETNHEALRGGNKHHGGVSE |
| 28 | GH61r2 | MRSTLAGALAAIAAQKVAG HATFQQLWHG SSCVRLPASNSPVTNVGSRDFVCNAGTRPV SGKCPVKAGGTVTIEMHQQPGDRSCNNEAIGGAHWGPVQVYLTKVQDAATADGSTGWFKIF SDSWSKKPGGNSGDDDNWGTRDLNACCGKMDVAIPADIASGDYLLRAEALALHTAGQAGGA QFYMSCYQMTVEGGSGTANPPTVKFPGAYSANDPGILVNIHAPLSSYTAPGPAVYAGGTIR EAGSACTGCAQTCKVGSSPSAVAPGSGAGNGGGFQPR |
| 29 | GH61t2 | MNYLAHCTND DCKSFKGDSGNVWVKIEQLAYNPSANPPWASDLLREHGAKWKVTIPPSLV PGEYLLRHEILGLHVAGTVMGAQFYPGCTQIRVTEGGSTQLPSGIALPGAYGPQDEGILVD LWRVNQGQVNYTAPGGPVWSEAWDTEFGGSNTTECATMLDDLLDYMAANDDPCCTDQNQFG SLEPGSKAAGGSPSLYDTVLVPVLQKKVPTKLQWSGPASVNGDELTERP |

TABLE 2 -continued

Glycoside Hydrolase 61 Proteins

| B | Desig-nation | Sequence (Putative Signal Peptide Sequence is Underlined) |
|---|---|---|
| 30 | GH61e2 | MKSSTPALFAAGLLAQHAAA HSIFQQASSG STDFDTLCTRMPPNNSPVTSVTSGDMTCN VGGTKGVSGFCEVNAGDEFTVEMHAQPGDRSCANEAIGGNHFGPVLIYMSKVDDASTADGS GDWFKVDEFGYDASTKTWGTDKLNENCGKRTFNIPSHIPAGDYLVRAEAIALHTANQPGGA QFYMSCYQVRISGGEGGQLPAGVKIPGAYSANDPGILVDIWGNDFNEYVIPGPPVIDSSVF |

IV. Recombinant Nucleic Acids and Proteins

In one aspect, the invention provides recombinant nucleic acids that comprise protein sequences set forth in TABLE 1 or TABLE 2 and variants (e.g., biologically active variants) thereof. The invention also provides expression vectors containing the recombinant nucleic acids, cells that comprise a recombinant nucleic acid or vector, recombinant proteins produced by such cells, and methods of using the cells and proteins.

In one aspect, the invention provides a recombinant nucleic acid sequence encoding a pre-protein comprising SEQ ID NO:1-30, the mature (secreted) protein encoded in SEQ ID NO: 1-30, or an amino-terminal truncated fragment of SEQ ID NO:1-30.

In one aspect the invention provides a recombinant, isolated or purified GH61 protein having a sequence comprising SEQ ID NO:1-30, the mature (secreted) protein encoded in SEQ ID NO: 1-30, or an amino-terminal truncated fragment of SEQ ID NO:1-30.

In one aspect the invention provides a recombinant nucleic acid sequence encoding a GH61 protein with at least about 70%, at least about 75%, about 80%, about 85%, about 90%, about 91%, about 92%, about 93%, about 94%, about 95%, about 96%, about 97%, about 98%, or about 99% sequence identity to a sequence comprising SEQ ID NO:1-30, the mature (secreted) protein encoded in SEQ ID NO: 1-30, or an amino-terminal truncated fragment of SEQ ID NO:1-30. In a related aspect, the invention provides a recombinant, isolated or purified GH61 protein having a sequence as set forth above. In some cases, a conservative amino acid substitution may be preferred over other types of substitutions.

GH61 proteins may be endogenous proteins isolated from fungal (e.g., M. thermophila) cells or may be recombinantly produced.

As discussed in detail below, GH61 proteins my comprise a endogenous or heterologous signal peptide. As discussed in detail below, a nucleic acid encoding a GH61 protein may be operably linked to a promoter, such as a heterologous promoter.

In one embodiment the invention provides a recombinant nucleic acid sequence comprising a sequence selected from SEQ ID NOS:31-59.

The nucleic acid sequence used to express a GH61 protein may be a native sequence obtained from M. thermophila that encodes the respective protein, or portion thereof that encodes the mature protein. Exemplary GH61 encoding sequences from M. thermophila are shown in SEQ ID NOs:31 to 59. Alternatively, numerous nucleic acid sequences that encode a specified protein may be designed by reference to the genetic code. In some embodiments, a sequence can be codon-optimized for a host cell other than M. thermophila is used (e.g., yeast cells). See GCG Codon-Preference, Genetics Computer Group Wisconsin Package; Codon W, John Peden, University of Nottingham; McInerney, J. O, 1998, Bioinformatics 14:372-73, in which case the nucleic acid sequence is other than the naturally occurring sequence.

In some embodiments, GH61 proteins of the invention are biologically active, i.e., have GH61 activity. GH61 activity can be measured using art-known methods, including methods described hereinbelow. Polypeptides lacking GH61 activity also find a variety of uses, including use for generation of antibodies for purification of GH61 proteins. Except where clear from context, reference herein to a GH61 protein (including variants) refers to proteins with GH61 activity.

In preferred embodiments, GH61 proteins that are variants of SEQ ID NOS:1-30 have at least 10% of the activity of the same molar amount of the wild-type protein from which they are derived. They may have at least 20%, at least 30%, at least 40%, at least 50%, at least 60%, at least 70%, at least 80%, at least 90%, at least 95%, or at least 99% of the activity of the wild-type protein.

GH61 proteins of that are variants of SEQ ID NOS:1-30 may be shorter than the wild-type protein by about 2%, about 3%, about 4%, about 5%, about 6%, about 7%, about 8%, about 9%, about 10%, about 15%, about 20%, about 25%, about 30%, about 35%, about 40%, about 45%, or about 50%, or about 60%, or about 70%, or about 80% compared with the reference (wild-type) sequence and/or part of a fusion protein in which a GH61 protein portion is joined to one or more other sequences. These variants may have at least about 70%, at least about 75%, about 80%, about 85%, about 90%, about 91%, about 92%, about 93%, about 94%, about 95%, about 96%, about 97%, about 98%, or about 99% sequence identity to a sequence comprising SEQ ID NO:1-30, the mature (secreted) protein encoded in SEQ ID NO: 1-30, or an amino-terminal truncated fragment of SEQ ID NO:1-30. The GH61 proteins may have an internal deletion, or a deletion at the amino- or carboxy-terminus relative to a wild-type sequence.

GH61 proteins may comprise an amino-terminal and/or carboxy-terminal deletion and/or internal deletion, but where the remaining amino acid sequence is at least about 60%, 70%, 75%, 80%, 85%, 90%, 92%, 93%, 94%, 95%, 96%, 97%, 98%, 99%, or 100% identical to the corresponding positions in the sequence to which it is being compared (e.g., a full-length GH61 variant of the invention). In some embodiments a Chitin Binding domain, or GH61 domain, is removed. In some embodiments the protein retains substantially all of the activity of the full-length polypeptide.

In some embodiments a mature GH61 protein has at least 70%, 80%, 90%, or 95% sequence identity to a wild-type sequence, and is substantially full length (at least 90% of the length of the wild-type sequence).

The invention also provides a recombinant GH61 nucleic acid sequences and protein expressed therefrom, wherein the protein has the sequence of GH61f, GH61a, GH61v, GH61p, GH61g, and GH61i (SEQ ID NOs:2, 7, 13, 20, 21, 23, 26), or a secreted fragment thereof; as well as variants at least about 70%, at least about 75%, about 80%, about 85%, about 90%, at least about 91%, at least about 92%, at least about 93%, at least about 94%, at least about 95%, at least about 96%, at least about 97%, at least about 98%, or at least about 99% identical to any one GH61f, GH61v, GH61p, GH61g, and GH61i (SEQ ID NOs:7, 13, 20, 21, 23, 26); or to any one of GH61a, GH61o, GH61v, GH61x, GH61b, and GH61e (SEQ ID NOs:2, 6, 13, 15, 16, 19, 30), fragments and variants thereof, and nucleic acids encoding such proteins, The invention also includes expression vectors comprising any one of the aforementioned nucleic acid sequences, cells comprising such expression vectors, and isolated GH61 proteins produced by the cells. Preferably, the variant GH61 protein has cellulase-enhancing activity. The protein encoding sequences may include a heterologous signal peptide and/or may be operably linked to a heterologous promoter.

Without intending to be bound by a particular mechanism of action, in the presence of GH61, hydrolysis of sugar polymers (e.g., cellulose substrates) by the enzymes produces more product over a particular time period, proceeds more rapidly, or goes further to completion when the GH61 protein is present, compared with a similar reaction under the same conditions in which the GH61 protein is absent.

GH61 proteins of this invention having cellulase-enhancing activity can be identified using standard methods for mapping function within a polypeptide, as known in the art. For example, a truncated variant may be expressed and then tested in a GH61 activity assay. Additional truncations can be introduced until activity is lost, at which point the minimum functional unit of the protein would be identified. Fragments containing any portion of the protein down to the identified size would typically be functional, as would be fusion constructs containing at least the functional core of the protein.

To generate biologically active variants that incorporate one or more amino acid changes in a GH61 encoding sequence (any of SEQ ID NOs:1 to 30), substitutions may be introduced into the protein sequence and the expressed protein tested for retention of activity.

A random or semirandom mutation strategy may be used to generate a large collection of active variants. The standard texts PROTOCOLS IN MOLECULAR BIOLOGY (Ausubel et al. eds.) and MOLECULAR CLONING: A LABORATORY MANUAL (Sambrook et al. eds.) describe techniques employing chemical mutagenesis, cassette mutagenesis, degenerate oligonucleotides, mutually priming oligonucleotides, linker-scanning mutagenesis, alanine-scanning mutagenesis, and error-prone PCR. Other efficient methods include the *E. coli* mutator strains of Stratagene (Greener et al., Methods Mol. Biol. 57:375, 1996) and the DNA shuffling technique of Maxygen (Patten et al., Curr. Opin. Biotechnol. 8:724, 1997; Harayama, Trends Biotechnol. 16:76, 1998; U.S. Pat. Nos. 5,605,793 and 6,132,970). To increase variation, a technology can be used that generates more abrupt changes, such as the DNA shuffling technique.

Commercially available kits may be used to obtain variants, including the GeneTailor™ Site-Directed Mutagenesis System sold by InVitrogen™ Life Technologies; the BD Diversify™ PCR Random Mutagenesis Kit™, sold by BD Biosciences/Clontech; the Template Generation System™, sold by MJ Research Inc., the XL1-Red™ mutator strain of *E. coli*, sold by Stratagene; and the GeneMorph® Random Mutagenesis Kit, also sold by Stratagene. By employing any of these systems in conjunction with a suitable GH61 activity assay, variants can be generated and tested in a high throughput manner.

Alternatively or in addition, the user may employ a strategy of directed evolution. See, for example, U.S. Pat. No. 7,981,614: Methods For Generating Polynucleotides Having Desired Characteristics; US 2011/0034342 A1: Method Of Generating An Optimized, Diverse Population Of Variants; U.S. Pat. No. 7,795,030: Methods And Compositions For Cellular And Metabolic Engineering; U.S. Pat. No. 7,647,184: High Throughput Directed Evolution By Rational Mutagenesis; U.S. Pat. No. 6,939,689: Exonuclease-Mediated Nucleic Acid Reassembly In Directed Evolution; and U.S. Pat. No. 6,773,900: End Selection In Directed Evolution. Mutagenesis may be performed in accordance with any of the techniques known in the art, including random and site-specific mutagenesis. Directed evolution can be performed with any of the techniques known in the art to screen for production of variants including shuffling.

Mutagenesis and directed evolution methods are well known in the art. See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811,238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., *Anal. Biochem.*, 254(2):157-78 [1997]; Dale et al., *Meth. Mol. Biol.*, 57:369-74 [1996]; Smith, *Ann. Rev. Genet.*, 19:423-462 [1985]; Botstein et al., *Science*, 229:1193-1201 [1985]; Carter, *Biochem. J.*, 237:1-7 [1986]; Kramer et al., *Cell*, 38:879-887 [1984]; Wells et al., *Gene*, 34:315-323 [1985]; Minshull et al., *Curr. Op. Chem. Biol.*, 3:284-290 [1999]; Christians et al., *Nat. Biotechnol.*, 17:259-264 [1999]; Crameri et al., *Nature*, 391:288-291 [1998]; Crameri et al., *Nat. Biotechnol.*, 15:436-438 [1997]; Zhang et al., *Proc. Nat. Acad. Sci. U.S.A.*, 94:4504-4509 [1997]; Crameri et al., *Nat. Biotechnol.*, 14:315-319 [1996]; Stemmer, *Nature*, 370:389-391 [1994]; Stemmer, *Proc. Nat. Acad. Sci. USA*, 91:10747-10751 [1994]; WO 95/22625; WO 97/0078; WO 97/35966; WO 98/27230; WO 00/42651; WO 01/75767; and WO 2009/152336, each of which is incorporated herein by reference.

In some embodiments, a GH61 protein of the invention has an amino acid sequence that is encoded by a nucleic acid that hybridizes under stringent conditions (i.e., medium-high, high, or very high stringency) to the complement of SEQ ID NO:31-59 and comprises GH61 activity.

V: GH61 Activity Assays

The cellulase enhancing activity of GH61 proteins of the invention can be determined using any suitable GH61 activity assay. For example, a purified or recombinant GH61 protein of this invention is obtained, and then assayed for GH61 activity by combining it with cellulase enzymes in a saccharification reaction, and determining if there is an increase in glucose yield, as compared to the same saccharification reaction conducted without the GH61.

In one approach, GH61 activity can be assayed by combining a cellulosic substrate with cellulase enzymes (e.g., 5-10 mg total weight of cellulase enzymes per gram of substrate) in the presence and absence of GH61 protein. In some embodiments the cellulase enzymes are a defined set of recombinant cellulase enzymes from *M. thermophila*.

In another approach, broth from a culture of wild-type *M. thermophila* is used (with and without supplementation by the GH61 protein). GH61 activity is evidenced by enhanced glucose yield in the presence of exogenous GH61 (i.e., beyond any enhancement resulting from endogenous GH61 in the broth).

It is also possible to use a broth supplemented with one or more purified enzymes.

Suitable enzymes include isolated recombinant enzymes cloned from *M. thermophila*, such as endoglucanase (EG), β-glucosidase (BGL), Type 1 cellobiohydrolase (CBH1), and/or Type 2 cellobiohydrolase (CBH2) in any combination suitable for the chosen substrate to yield a measurable product. Exemplary cellulase enzymes that may be used to assay for GH61 activity may have amino acid sequences selected from any of SEQ ID NOs:61 to 68.

In one exemplary assay for measuring GH61 activity from *M. thermophila* derived GH61 proteins and variant proteins, the cellulase enzymes used are *M. thermophila* BGL1 (SEQ ID NO:66; Badhan et al., *Bioresour Technol.* 2007 February; 98(3):504-10); *M. thermophila* CBH1 (SEQ ID NO:67; Park J I et al., Badhan et al., *Bioresour Technol.* 2007 February; 98(3):504-10); and *M. thermophila* CBH2 (SEQ ID NO:68). In some embodiments, endoglucanse is also used: *M. thermophila* EG2 (SEQ ID NO:65; Rosgaard L. et al., *Prog.* 2006; 22(2):493-8; Badhan et al., supra).

Alternatively, commercially available preparations comprising a mixture of cellulase enzymes may be used, such as Laminex™ and Spezyme™ from Genencor International, Rohament™ from Rohm GmbH, and Celluzyme™ Cereflo™ and Ultraflo™ from Novozymes Inc.

Assays with cellulose enzymes are typically done at 50° C., but may also be carried out at 35, 45, 55, 60, or 65° C. The GH61 protein and enzymes are combined with the substrate and incubated so as to produce fermentable sugars. The sugars are then recovered and quantitated for yield of glucose. One suitable substrate is wheat straw (e.g., pretreated wheat straw). Other cellulosic substrates listed in this disclosure may be used as an alternative, including corn stover pretreated with sulfuric acid (see U.S. Pat. No. 7,868,227), and other substrates described in Section XIII below.

An assay method is provided by Harris et al., 2010, *Biochemistry* 49:3305-3316, incorporated herein by reference, may also be used. In this method, corn stover is pretreated with sulfuric acid, washed, incubated with cellulase enzymes and GH61 for several days, and then the yield of sugars was quantitated by refraction.

Another assay method is provided in U.S. Pat. No. 7,868,227, incorporated herein by reference. In this method, the cellulosic substrate is PCS (corn stover pretreated with heat and dilute sulfuric acid; WO 2005/074647); a cellulose enzyme mixture is Cellulcast®, a blend of cellulase enzymes from the fungus *Trichoderma reesei*, available from Sigma-Aldrich. Hydrolysis of PCS is conducted in a total reaction volume of 1.0 mL and a PCS concentration of 50 mg/mL in 1 mM manganese sulfate, 50 mM sodium acetate buffer pH 5.0. The test protein is combined with the base cellulase mixture at relative concentrations between 0 and 100% total protein. The protein composition is incubated with the PCS at 65° C. for 7 days. Combined yield of glucose and cellobiose may be measured by refractive index detection.

GH61 activity is calculated as an increase in glucose production from the substrate by the cellulase(s) in the presence of GH61 protein, in comparison with the same reaction mixture in the absence of GH61 protein. Typically, the increase is dose-dependent within at least a 3-fold range of concentrations. GH61 activity can be expressed as a degree of "synergy" as discussed in Example 8.

The addition or presence of recombinant or isolated GH61 protein may increase yield of product from cellulase enzymes by, for example, at least 1%, at least 5%, at least 10%, at least 20%, 30%, 50%, 70%, 2-fold, 3-fold or more.

VI. Expression of GH61 Proteins

Cell culture, recombinant genetics, protein engineering and fermentation technologies that may be employed in the expression, production and use of the GH61 proteins, compositions, and other products of this invention are known in the art. For convenience, certain aspects are described briefly below. Although described primarily in the context of expression of GH61 proteins, it will be appreciated that the same methods, cells, etc. may be used to express cellulase proteins and other proteins so as, but not limited to, those described elsewhere herein.

In some embodiments, the construct further comprises regulatory sequences, including, for example, a promoter, operably linked to the protein encoding sequence. Large numbers of suitable vectors and promoters are known to those of skill in the art.

Signal Peptides

In some embodiments, a GH61 protein may include a signal peptide, so that when expressed in a host cell, the mature form (e.g., SEQ ID NO:2) is secreted into a cell culture broth. The GH61 protein (or variant) may include its corresponding native signal peptide as shown in TABLES 1 and 2.

Alternatively, a recombinant nucleic acid sequence encoding a protein comprising SEQ ID NO:2, or the secreted portion of any one of SEQ ID NOs:3 to 30, an amino terminal truncated portion of any one of SEQ ID NOs:2 to 30, or a variant thereof may have a heterologous signal peptide fused to the N-terminus.

Various signal peptides may be used, depending on the host cell and other factors. Useful signal peptides for filamentous fungal host cells include the signal peptides obtained from *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola lanuginosa* lipase, and *T. reesei* cellobiohydrolase II (TrCBH2).

Useful signal peptides for bacterial host cells are the signal peptides obtained from the genes for *Bacillus* NCIB 11837 maltogenic amylase, *Bacillus stearothermophilus* α-amylase, *Bacillus licheniformis* subtilisin, *Bacillus licheniformis* β-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57:109-137.

Useful signal peptides for yeast host cells also include those from the genes for *Saccharomyces cerevisiae* alpha-factor, *Saccharomyces cerevisiae* SUC2 invertase (see Taussig and Carlson, 1983, *Nucleic Acids Res* 11:1943-54; SwissProt Accession No. P00724), and others. Romanos et al., 1992, *Yeast* 8:423-488. Variants of these signal peptides and other signal peptides are suitable.

Also provided by the invention are recombinant proteins comprising a signal peptide shown Table 1 or Table 2 fused to amino terminus of a heterologous protein (i.e., a protein with which it is not associated in nature, which may be a protein other than a GH61 protein). Thus, signal peptides shown in Tables 1 and 2 may be used to cause secretion of a recombinantly expressed heterologous protein expressed in a host cell. In some embodiments the host cell is *Myceliophthora thermophila*.

Promoters

In order to obtain high levels of expression in a particular host it is often useful to express the GH61 variant of the present invention under the control of a heterologous promoter. A promoter sequence may be operably linked to the 5' region of the GH61 coding sequence using routine methods.

Examples of useful promoters for expression of GH61s include promoters from fungi. In some embodiments, a promoter sequence that drives expression of a gene other than a GH61 gene in a fungal strain may be used. As a non-limiting example, a fungal promoter from a gene encoding an endoglucanase may be used. In some embodiments, a promoter sequence that drives the expression of a GH61 gene in a fungal strain other than the fungal strain from which the GH61 variant was derived may be used. As a non-limiting example, if the GH61 variant is derived from C1, a promoter from a *T. reesei* GH61 gene may be used or a promoter as described in WO 2010107303, such as but not limited to the sequences identified as SEQ ID NO:25, SEQ ID NO:26, SEQ ID NO:27, SEQ ID NO:28, or SEQ ID NO:29 in WO 2010107303.

Examples of other suitable promoters useful for directing the transcription of the nucleotide constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, eg1, eg12, pepA, hfb1, hfb2, xyn1, amy, and glaA (Nunberg et al., 1984, *Mol. Cell. Biol.*, 4:2306-2315, Boel et al., 1984, *EMBO J.* 3:1581-85 and EPA 137280, all of which are incorporated herein by reference), and mutant, truncated, and hybrid promoters thereof. In a yeast host, useful promoters can be from the genes for *Saccharomyces cerevisiae* enolase (eno-1), *Saccharomyces cerevisiae* galactokinase (gall), *Saccharomyces cerevisiae* alcohol dehydrogenase/glyceraldehyde-3-phosphate dehydrogenase (ADH2/GAP), and *S. cerevisiae* 3-phosphoglycerate kinase. Other useful promoters for yeast host cells are described by Romanos et al., 1992, *Yeast* 8:423-488, incorporated herein by reference. Promoters associated with chitinase production in fungi may be used. See, e.g., Blaiseau and Lafay, 1992, *Gene* 120243-248 (filamentous fungus *Aphanocladium album*); Limon et al., 1995, *Curr. Genet,* 28:478-83 (*Trichoderma harzianum*), both of which are incorporated herein by reference.

Promoters known to control expression of genes in prokaryotic or eukaryotic cells or their viruses and which can be used in some embodiments of the invention include SV40 promoter, *E. coli* lac or trp promoter, phage lambda $P_L$ promoter, tac promoter, T7 promoter, and the like. In bacterial host cells, suitable promoters include the promoters obtained from the *E. coli* lac operon, *Streptomyces coelicolor* agarase gene (dagA), *Bacillus subtilis* levansucranse gene (sacB), *Bacillus licheniformis* α-amylase gene (amyl), *Bacillus stearothermophilus* maltogenic amylase gene (amyM), *Bacillus amyloliquefaciens* α-amylase gene (amyQ), *Bacillus subtilis* xylA and xylB genes and prokaryotic β-lactamase gene.

Any other promoter sequence that drives expression in a suitable host cell may be used. Suitable promoter sequences can be identified using well known methods. In one approach, a putative promoter sequence is linked 5' to a sequence encoding a reporter protein, the construct is transfected into the host cell (e.g., C1) and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (Henriksen et al, 1999, *Microbiology* 145:729-34, incorporated herein by reference) or a lacZ reporter gene (Punt et al, 1997, *Gene,* 197:189-93, incorporated herein by reference). Functional promoters may be derived from naturally occurring promoter sequences by directed evolution methods. See, e.g. Wright et al., 2005, *Human Gene Therapy,* 16:881-892, incorporated herein by reference.

Additional promoters include those from *M. thermophila*, provided in U.S. patent application Ser. No. 13/214,406 filed Aug. 22, 2010, as well as WO 2010/107303 and are hereby incorporated by reference in their entireties.

Vectors

The present invention makes use of recombinant constructs comprising a sequence encoding a GH61 as described above. Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. Polynucleotides of the present invention can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

The invention provides expression vectors for causing a GH61 protein to be produced from a suitable host cell, which may be a fungus (e.g., *M. thermophila* or yeast). Such a vector may be selected from but are not limited to derivatives of viral vectors; bacterial plasmids; phage DNA; baculovirus; yeast plasmids; vectors derived from combinations of plasmids and phage DNA, and recombinant shuttle vectors. The vector may be introduced into a host cell with a GH61-encoding polynucleotide so that it is operably linked to a promoter that is active in the host cell. The vector is selected to express the encoded protein, and may replicate as an episome in the intended host cell, or integrate into the host cell's genome.

In a particular aspect the present invention provides an expression vector comprising a GH61 polynucleotide operably linked to a heterologous promoter. Expression vectors of the present invention may be used to transform an appropriate host cell to permit the host to express the GH61 protein. Methods for recombinant expression of proteins in fungi and other organisms are well known in the art, and a number expression vectors are available or can be constructed using routine methods. See, e.g., Tkacz and Lange, 2004, ADVANCES IN FUNGAL BIOTECHNOLOGY FOR INDUSTRY, AGRICULTURE, AND MEDICINE, KLUWER ACADEMIC/PLENUM UBLISHERS. New York; Zhu et al., 2009, Construction of two Gateway vectors for gene expression in fungi Plasmid 6:128-33; Kavanagh, K. 2005, FUNGI: BIOLOGY AND APPLICATIONS Wiley, all of which are incorporated herein by reference.

Host Cells

The GH61 proteins of the invention can be expressed in a host cell comprising a recombinant nucleic acid encoding the GH61 protein. The host cell may also express other proteins of interest, particularly one or more cellulase enzymes that work in concert with the GH61 protein in the process of saccharification. In one embodiment the host cell is a cellulase-engineered cell. Thus, the cellulase enzymes may be endogenously expressed by the host cell, or they may be expressed from other nucleic acids.

In another approach, two or more populations of host cells, each expressing a different protein or set of proteins (e.g., a GH61 protein and a cellulase) may be cultured together. The two host cells may be the same or different cell species. Cells expressing GH61 protein and cells expressing cellulase enzymes can be combined and cultured together to produce compositions of this invention containing both GH61 proteins and cellulase enzymes. Alternatively, the culture broth from each cell population can be collected separately, optionally fractionated to enrich for the respective activities, and then mixed together to produce the desired combination.

Suitable fungal host cells include, but are not limited to Ascomycota, Basidiomycota, Deuteromycota, Zygomycota, Fungi imperfecti. In some embodiments, preferred fungal host cells are yeast cells, and filamentous fungal cells, including all filamentous forms of the subdivision Eumycotina and Oomycota. Hawksworth et al., In Ainsworth and Bisby's DICTIONARY OF THE FUNGI, 8$^{th}$ edition, 1995, CAB International, University Press, Cambridge, UK. Filamentous fungi are characterized by a vegetative mycelium with a cell wall composed of chitin, cellulose and other complex polysaccharides, and are morphologically distinct from yeast. *Trichoderma* may also be a source of one or more cellulases for use in combination with GH61 proteins.

The host cell may be a species of *Achlya, Acremonium, Aspergillus, Aureobasidium, Azospirillum, Bjerkandera, Cellulomonas, Cephalosporium, Ceriporiopsis, Chrysosporium, Clostridium, Coccidioides, Cochliobolus, Coprinus, Coriolus, Corynascus, Cryphonectria, Cryptococcus, Dictyostelium, Diplodia, Elizabethkingia, Endothia, Erwinia, Escherichia, Fusarium, Gibberella, Gliocladium, Gluconacetobacter, Humicola, Hypocrea, Kuraishia, Mucor, Myceliophthora, Neurospora, Nicotiana, Paenibacillus, Penicillium, Periconia, Phaeosphaeria, Phlebia, Piromyces, Podospora, Prevotella, Pyricularia, Rhizobium, Rhizomucor, Rhizopus, Ruminococcus, Saccharomycopsis, Salmonella, Schizophyllum, Scytalidium, Septoria, Sporotrichum, Streptomyces, Talaromyces, Thermoanaerobacter, Thermoascus, Thermotoga, Thielavia, Tolypocladium, Trametes, Trichoderma, Tropaeolum, Uromyces, Verticillium, Volvariella, Wickerhamomyces*, or corresponding teleomorphs, or anamorphs, and synonyms or taxonomic equivalents thereof.

An exemplary host cell is yeast. Examples are *Candida, Hansenula, Saccharomyces, Schizosaccharomyces, Pichia, Kluyveromyces*, or *Yarrowia*. The yeast cell may be *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

An exemplary cell may be *Myceliophthora thermophila*, sometimes referred to as "C1". As used herein, the term "C1" refers to *Myceliophthora thermophila*, including a fungal strain described by Garg (See, Garg, *Mycopathol.*, 30: 3-4 [1966]). As used herein, "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, all of which are incorporated herein by reference, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006, CBS (Centraalbureau voor Schimmelcultures) 122188, CBS 251.72, CBS 143.77, CBS 272.77, CBS122190, CBS122189, and VKM F-3500D. Exemplary C1 derivatives include modified organisms in which one or more endogenous genes or sequences have been deleted or modified and/or one or more heterologous genes or sequences have been introduced. Derivatives include, but are not limited to UV18#100f ΔalpI, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δpyr5 Δalp1 Δpep4 Δalp2, as described in WO 2008073914 and WO 2010107303, each of which is incorporated herein by reference.

In some embodiments the host cell may be of the *Trichoderma* species, such as *T. longibrachiatum, T. viride, Hypocrea jecorina* or *T. reesei, T. koningii*, and *T. harzianum*. Alternatively, the host cell is of the *Aspergillus* species, such as *A. awamori, A. funigatus, A. japonicus, A. nidulans, A. niger, A. aculeatus, A. foetidus, A. oryzae, A. sojae*, and *A. kawachi*. Alternatively, the host cell is of the *Fusarium* species, such as *F. bactridioides, F. cerealis, F. crookwellense, F. culmorum, F. graminearum, F. graminum. F. oxysporum, F. roseum*, and *F. venenatum*.

The host cell may also be of the *Neurospora* species, such as *N. crassa*. Alternatively, the host cell is of the *Humicola* species, such as *H. insolens, H. grisea*, and *H. lanuginosa*. Alternatively, the host cell is of the *Mucor* species, such as *M. miehei* and *M. circinelloides*. The host cell may be of the *Rhizopus* species, such as *R. oryzae* and *R. niveus*. Alternatively, the host cell is of the *Penicillum* species, such as *P. purpurogenum*, *P. chrysogenum*, and *P. verruculosum*.

Alternatively, the host cell is of the *Thielavia* species, such as *T. terrestris*. Alternatively, the host cell is of the *Tolypocladium* species, such as *T. inflatum* and *T. geodes*. Alternatively, the host cell is of the *Trametes* species, such as *T. villosa* and *T. versicolor*. Alternatively, the host cell is of the *Chrysosporium* species, such as *C. lucknowense*, *C. keratinophilum*, *C. tropicum*, *C. merdarium*, *C. inops*, *C. pannicola*, and *C. zonatum*. In a particular embodiment the host is *C. lucknowense*. Alternatively, the host cell is an algae such as *Chlamydomonas* (such as *C. reinhardtii*) and *Phormidium* (*P*. sp. ATCC29409).

Alternatively, the host cell is a prokaryotic cell. Suitable prokaryotic cells include Gram-positive, Gram-negative and Gram-variable bacterial cells. Examples of bacterial host cells include *Bacillus* (such as *B. subtilis*, *B. licheniformis*, *B. megaterium*, *B. stearothermophilus* and *B. amyloliquefaciens*), *Streptomyces* (e.g., *S. ambofaciens*, *S. achromogenes*, *S. avermitilis*, *S. coelicolor*, *S. aureofaciens*, *S. aureus*, *S. fungicidicus*, *S. griseus*, and *S. lividans*), and *Streptococcus* (such as *S. equisimiles*, *S. pyogenes*, and *S. uberis*) species.

Non-limiting examples of the cell types in this section include *Aspergillus aculeatus*, *Azospirillum irakense* KBC1, *Bacillus* sp. GL1, *Cellulomonas biazotea*, *Clostridium thermocellum*, *Thermoanaerobacter brockii*, *Coccidioides posadassi*, *Dictyostelium discoideum*, *Elizabethkingia meningoseptica*, *Erwinia chrysanthemi*, *Escherichia coli*, *Gluconacetobacter xylinus*, *Hypocrea jecorina*, *Kuraishia capsulata*, *Nicotiana tabacum*, *Paenibacillus* sp. C7, *Penicillium brasilianum*, *Periconia* sp. BCC 2871, *Phaeosphaeria avenaria*, *Prevotella albensis*, *Rhizobium leguminosarum*, *Rhizomucor miehei*, *Ruminococcus albus*, *Saccharomycopsis fibuligera*, *Salmonella typhimurium*, *Septoria lycopersici*, *Streptomyces coelicolor*, *Talaromyces emersonii*, *Thermotoga maritima*, *Tropaeolum majus*, *Uromyces viciae-fabae*, and *Wickerhamomyces anomalus*.

Strains that may be used in the practice of the invention (both prokaryotic and eukaryotic strains) may be obtained from any suitable source, including but not limited to the American Type Culture Collection (ATCC), or other biological depositories such as Deutsche Sammlung von Mikroorganismen and Zellkulturen GmbH (DSM), Centraalbureau Voor Schimmelcultures (CBS), and the Agricultural Research Service Patent Culture Collection, Northern Regional Research Center (NRRL).

Host cells may be genetically modified to have characteristics that improve genetic manipulation, protein secretion, protein stability or other properties desirable for expression or secretion of protein. For example, knock-out of Alp1 function results in a cell that is protease deficient. Knock-out of pyr5 function results in a cell with a pyrimidine deficient phenotype. Host cells may be modified to delete endogenous cellulase protein-encoding sequences or otherwise eliminate expression of one or more endogenous cellulases. Expression of one or more unwanted endogenous cellulases may be inhibited to increase the proportion of cellulases of interest, for example, by chemical or UV mutagenesis and subsequent selection. Homologous recombination can be used to induce targeted gene modifications by specifically targeting a gene in vivo to suppress expression of the encoded protein.

Transformation and Cell Culture

Polynucleotides of the invention, encoding GH61 proteins, cellulase proteins or other proteins, may be introduced into host cells for expression. The polynucleotide may be introduced into the cell as a self-replicating episome (e.g., expression vector) or may be stably integrated into the host cell DNA. Introduction of a vector or a DNA construct into a host cell can be effected by any suitable method, including but not limited to calcium phosphate transfection, DEAE-Dextran mediated transfection, electroporation, or other common techniques (See Davis et al., 1986, BASIC METHODS IN MOLECULAR BIOLOGY; Sambrook et al (2001) Molecular Cloning: A Laboratory Manual, 3rd ed., Cold Spring Harbor Laboratory Press, New York; "Guide to Yeast Genetics and Molecular Biology," C. Guthrie and G. Fink, Eds., Methods in Enzymology 350 (Academic Press, San Diego, 2002). In some embodiments, the polynucleotide that is introduced into the host cell remains in the genome or on a plasmid or other stably maintained vector in the cell and is capable of being inherited by the progeny thereof. Stable transformation is typically accomplished by transforming the host cell with an expression vector comprising the polynucleotide of interest along with a selectable marker gene (e.g., a gene that confers resistance to an antibiotic). Only those host cells which have integrated the polynucleotide sequences of the expression vector into their genome will survive selection with the marker (e.g., antibiotic). These stably transformed host cells can then be propagated according to known methods in the art.

Engineered host cells can be cultured in conventional nutrient media modified as appropriate for activating promoters, selecting transformants, or amplifying the GH61 polynucleotide. General references on cell culture techniques and nutrient media include GENE MANIPULATIONS IN FUNGI, Bennett, J. W. et al., Ed., Academic Press, 1985; MORE GENE MANIPULATIONS IN FUNGI, Bennett, J. W. et al., Ed., Academic Press, 1991; and THE HANDBOOK OF MICROBIOLOGICAL MEDIA, CRC Press, Boca Raton, Fla., 1993. Culture conditions for C1 host cells are described in US 2008/0194005, US 2003/0187243, WO 2008/073914 and WO 01/79507. Culture conditions, such as temperature, pH and the like, are those previously used with the host cell selected for expression, and will be apparent to those skilled in the art. As noted, many references are available describing the culture and production of many cells, including cells of bacterial, plant, animal (especially mammalian) and archebacterial origin. Atlas and Parks (eds.) The Handbook of Microbiological Media (1993) CRC Press, Boca Raton, Fla., which is incorporated herein by reference. Additional information for cell culture is found in available commercial literature such as the Life Science Research Cell Culture Catalogue (1998) from Sigma-Aldrich, Inc (St Louis, Mo.) ("Sigma-LSRCCC") and, for example, The Plant Culture Catalogue and supplement (1997) also from Sigma-Aldrich, Inc (St Louis, Mo.) ("Sigma-PCCS"), all of which are incorporated herein by reference.

Protein Enrichment and Purification

An expressed polypeptide can be recovered from cells or broth. Optionally a protein can be enriched for (e.g., purified or partially purified) using methods well known in the art. For example, the polypeptide may be isolated from the nutrient medium by conventional procedures including, but not limited to, centrifugation, filtration, extraction, spray-drying, evaporation, chromatography (e.g., ion exchange, solid phase binding, affinity, hydrophobic interaction, chromatofocusing, and size exclusion chromatography) and/or filtration, or precipitation. Protein refolding steps can be used, as desired, in completing the configuration of the mature protein. Finally, high performance liquid chromatography (HPLC) can be employed in the final purification steps. See, for example, Parry et al., 2001, *Biochem. J.*

353:117, and Hong et al., 2007, *Appl. Microbiol. Biotechnol.* 73:1331, both incorporated herein by reference. Other purification methods well known in the art include those set forth in Sandana (1997) *Bioseparation of Proteins*, Academic Press, Inc.; Bollag et al. (1996) *Protein Methods*, $2^{nd}$ Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* $3^{rd}$ *Edition*, Springer Verlag, NY; Janson and Ryden (1998) *Protein Purification: Principles, High Resolution Methods and Applications, Second Edition*, Wiley-VCH, NY; and Walker (1998) *Protein Protocols on CD-ROM*, Humana Press, NJ, PROTEIN PURIFICATION: PRINCIPLES, HIGH RESOLUTION METHODS, AND APPLICATIONS, J. C. Janson (Ed.), Wiley 2011; HIGH THROUGHPUT PROTEIN EXPRESSION AND PURIFICATION: METHODS AND PROTOCOLS, S. A. Doyle (Ed.), Humana Press 2009; all of which are incorporated herein by reference.

General Techniques

Polynucleotides encoding GH61 proteins and other proteins can be prepared, for example, by chemical synthesis using the classical phosphoramidite method described by Beaucage, et al., 1981, *Tetrahedron Letters*, 22:1859-69, or the method described by Matthes, et al., 1984, *EMBO J.* 3:801-05. Oligonucleotides of up to about 40 bases are individually synthesized, then joined (e.g., by enzymatic or chemical ligation methods, or polymerase-mediated methods) to form essentially any desired continuous sequence.

General texts that describe molecular biological techniques including the use of vectors, promoters, in vitro amplification methods including the polymerase chain reaction (PCR) and the ligase chain reaction (LCR) are Berger and Kimmel, GUIDE TO MOLECULAR CLONING TECHNIQUES, METHODS IN ENZYMOLOGY volume 152 Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989 and CURRENT PROTOCOLS IN MOLECULAR BIOLOGY, F. M. Ausubel et al., eds., Current Protocols (as supplemented through 2009).

VII. Purification of Endogenous GH61 Proteins from Culture Broth

As an alternative to recombinant expression of GH61 proteins of this invention, secreted GH61 proteins can be fractionated from the culture broth of *Myceliophthora thermophila* that produce and secrete one or more endogenous proteins with GH61 activity. Likewise, non-secreted endogenous GH61 can be recovered by lysis of *M. thermophila* cells.

GH61 proteins of this invention can be obtained from cells that express GH61 proteins using standard protein separation techniques, such as described hereinabove, and following GH61 activity during fractionation with a suitable GH61 activity assay.

As illustrated in the Examples, when isolating protein from *M. thermophila* culture broth, an effective combination is chromatography on a phenyl group presenting resin, followed by anion exchange chromatography. As a result of the separation techniques, specific activity of the GH61 protein (the activity observed in an activity assay per unit total protein) may be increased by about 10-, about 25-, about 100-, about 250-, about 1000-fold, or more.

Once GH61 activity has been fractionated from a suitable source, the fractions can be recombined with each other and/or with recombinant GH61 proteins in any combination (see Examples). Such fractions or combinations can then be used to promote activity of one or more cellulases, as described herein. Purified or recombinant GH61 proteins of this invention, and combinations thereof, may cause an increase in the rate cellulase activity for conversion of cellulosic biomass or other substrate to fermentable sugars by at least about 1%, 5%, 10%, 15%, 20%, at least about 25%, at least about 30%, at least about 35%, at least about 40%, at least about 45%, at least about 50%, at least about 55%, at least about 60%, at least about 65%, at least about 75%, at least about 80%, at least about 2-fold, at least about 4-fold, or more.

By using such protein separation techniques in combination with a GH61 activity assay, it has been determined that protein fractions having complete or partial sequence data corresponding to GH61f, GH61a, GH61v, GH61p, GH61g, and GH61i (SEQ ID NOs:2, 7, 13, 20, 21, 23, 26) have the ability to enhance cellulase activity in accordance with their classification as a GH61 protein (See Examples).

VIII. Cellulases

The GH61 proteins of this invention are useful for increasing the yield of fermentable sugars in a saccharification reaction with one or more cellulase enzymes. The GH61 protein and cellulase enzymes can be produced in the same cell or in different cells. In either case, the cellulase enzymes can be expressed from a recombinant encoding region or from a constitutive gene. The cellulase enzymes can be provided in the form of a culture broth or supernatant, or purified to any extent desired.

Cellulases for use in the present invention may be derived from any organism that produces cellulases, and may be expressed in, for illustration and not limitation, any host cell described herein. In some embodiments cellulases are derived from and/or expressed in a filamentous fungus (e.g., *Myceliophthora, Aspergillus Azospirillum*, and *Trichoderma* species) or yeast cell. For illustration, cellulases derived from any of the following cells may be used: For example, many fungi (including but not limited to *Thielavia, Humicola, Chaetomium, Neurospora, Chaetomidium, Bortyosphaeria, Trichophaea, Aspergillus, Schizophyllum, Agaricus, Sporotrichium, Corynascus, Myceliophthora, Acremonium, Thermoascus, Alternaria, Botryotinia, Phanerochaete, Claviceps, Cochliobolus, Cryphonectria, Emericella, Fusarium, Gibberella, Hypocrea Irpex, Magnaporthe, Nectria, Neosartorya, Penicillium, Phanerochaete, Pleurotus, Podospora, Polyporus, Sclerotinia, Sordaria, Talaromyces, Trichoderma*, and *Volvariella* species. For example, *Acremonium thermophilum; Agaricus bisporus; Alternaria alternate; Aspergillus aculeatus; Aspergillus clavatus; Aspergillus flavus; Aspergillus fumigatus; Aspergillus nidulans; Aspergillus niger; Aspergillus oryzae; Aspergillus terreus; Botryotinia fuckeliana; Chaetomium thermophilum; Phanerochaete Chtysosporium; Claviceps purpurea; Cochliobolus carbonum; Cryphonectria parasitica; Emericella nidulans; Fusarium oxysporum; Fusarium poae; Fusarium venenatum; Gibberella avenacea; Gibberella pulicaris; Gibberella zeae; Humicola grisea; Hypocrea koningii; Hypocrea lixii; Hypocrea virens; Irpex lacteus; Magnaporthe grisea; Nectria haematococca; Neosartotya fischeri; Neurospora crassa; Penicillium chrysogenum; Penicillium decumbens; Penicillium funiculosum; Penicillium janthinellum; Penicillium marneffei; Penicil-*

*lium occitanis; Penicillium oxalicum; Phanerochaete chrysosporium; Pleurotus* sp. *'Florida'; Podospora anserine; Polyporus arcularius; Sclerotinia sclerotiorum; Sordaria macrospora; Talaromyces emersonii; Talaromyces stipitatus; Thermoascus aurantiacus; Trichoderma* sp.; *Trichoderma viride; Trichoderma reseipdb; Volvariella volvacea.* In one embodiment the cell is *M. thermophila.*

Endoglucanase (EG)

The invention provides a cell expressing a GH61 protein in combination with a recombinant endoglucanase. The terms "endoglucanase" or "EG" refer to a group of cellulase enzymes classified as E.C. 3.2.1.4. These enzymes catalyze the hydrolysis of internal β-1,4 glycosidic bonds of cellulose.

For example, the cell may contain a recombinant polynucleotide sequence encoding the EG protein. In some embodiments the EG polynucleotide sequence is operably linked to a heterologous promoter and/or the EG polypeptide sequence comprises a signal sequence. The EG protein may be expressed as a pre-protein, which is secreted from the cell with concomitant loss of the signal peptide.

The EG may comprise an endogenous *M. thermophila* endoglucanase such as *M. thermophila* EG2a (see WO 2007/109441) or a variant thereof. The EG may be from *S. avermitilis*, having a sequence set forth in GenBank accession NP_821730, or a variant such as described in US 2010/0267089 A1. The EG may be a *Thermoascus aurantiacus* EG, or an endogenous EG from a bacteria, a yeast, or a filamentous fungus other than *M. thermophila*. Indeed, it is contemplated that any suitable EG will find use in combination with the GH61 proteins provided herein. It is not intended that the present invention be limited to any specific EG.

β-Glucosidase (BGL)

The invention provides a cell expressing a GH61 protein in combination with a recombinant β-glucosidase. The terms "β-glucosidase", "cellobiase" or "BGL" refer to a group of cellulase enzymes classified as E.C. 3.2.1.21. These enzymes hydrolyze cellobiose to glucose.

For example, the cell may contain a recombinant polynucleotide sequence encoding the BGL protein, where the polynucleotide sequence is operably linked to a heterologous promoter and/or signal sequence. The BGL protein may be expressed as a pre-protein, which is secreted from the cell with concomitant loss of the signal peptide.

In one embodiment, the BGL may be a *M. thermophila* BGL1 or variant thereof. The BGL1 may comprise the sequence set forth in SEQ ID NO:60 or SEQ ID NO:66, or is a variant thereof, or a variant described in US 2011/0129881 A1. Alternatively, the BGL is from *Thermoascus aurantiacus* (TaBGL), having a sequence set forth as SEQ ID NO:61, or is a variant thereof, or a variant such as those described in US 2011/0124058 A1.

Alternatively, the BGL is from *Azospirillum irakense* (CelA), having a sequence set forth as SEQ ID NO:62, or is a variant thereof, or a variant described in US 2011/0114744 A1. Alternatively, the BGL is described in TABLE 14 of PCT application No. PCT/US2010/038902. Alternatively, the BGL is an endogenous BGL from a bacteria, a yeast, or a filamentous fungus other than *M. thermophila*. Also contemplated is use of variants of such naturally occurring BGLs. Indeed, it is contemplated that any suitable BGL will find use in combination with the GH61 proteins provided herein. It is not intended that the present invention be limited to any specific BGL.

Type 1 and Type 2 Cellobiohydrolase

The invention provides a cell expressing a GH61 protein in combination with a recombinant Type 1 cellobiohydrolase. The terms "cellobiohydrolase", "exoglucanase", "exocellobiohydrolase" or "CBH" refer to a group of cellulase enzymes classified as E.C. 3.2.1.91. Type 1 cellobiohydrolases (CBH1) hydrolyze cellobiose processively from the reducing end of cellulose chains. Type 2 cellobiohydrolases (CBH2) hydrolyze cellobiose processively from the nonreducing end of cellulose chains.

For example, the cell may contain a recombinant polynucleotide sequence encoding the CBH protein, where the polynucleotide sequence is operably linked to a heterologous promoter and/or signal peptide sequence. The CBH protein may be expressed as a pre-protein, which is secreted from the cell with concomitant loss of the signal peptide.

The cell may be a *M. thermophila* cell, and may be an endogenous cellobiohydrolase, such as CBH1a, having a sequence set forth in SEQ ID NO:63 or 67 or is a variant thereof. Alternatively, the CBH1 is an endogenous CBH1 from a bacteria, a yeast, or a filamentous fungus other than *M. thermophila*, or a variant of such naturally occurring CBH1s. Indeed, it is contemplated that any suitable CBHs will find use in combination with the GH61 proteins provided herein. It is not intended that the present invention be limited to any specific CBHs.

IX. Cell Free Compositions in which GH61 Protein is Combined with Cellulase Enzymes In one aspect, the invention provides a composition comprising at least one GH61 protein described herein (e.g., comprising a sequence of SEQ ID NO:1-30, comprising a secreted portion of the GH61 protein, comprising a amino-terminal truncated portion of the GH61 protein, and biologically active variants thereof), in combination with at least one, at least two, at least three or more cellulases selected from EGs, BGLs, CBH1s, and/or CBH2s, where the combined mass of the GH61, EG, BGL, CBH1 and/or CBH2 is at least about 50%, at least about 60%, or at least about 70% of the total cell-free protein in the composition. The GH61 protein (whether in broth or in partially purified form) can be combined with cellulases from *M. thermophila* or from other cellulase-producing organisms (including, for example, organisms listed below).

In some compositions of the invention, the GH61 protein comprises SEQ ID NO:2; and (a) the CBH1 is a *M. thermophila* CBH1a variant with at least about 80%, at least about 85%, sometimes at least about 90%, and sometimes at least about 95% sequence identity to SEQ ID NO:63 or 67; and/or (b) the CBH2 is a *M. thermophila* CBH2b variant with at least about 80%, at least about 85%, sometimes at least about 90%, and sometimes at least about 95% sequence identity to SEQ ID NO:64 or 68; and/or (c) the BGL is a *M. thermophila* BGL1 variant with at least about 80%, at least about 85%, sometimes at least about 90%, and sometimes at least about 95% sequence identity to SEQ ID NO:60 or 66.

The composition may also be a cell culture medium (i.e., culture broth) that contains secreted recombinant GH61 and cellulase proteins. Such media may be produced by culturing recombinant cells described hereinabove under conditions in which a combination of enzymes (e.g., GH61, EG, CBH and/or BGL proteins) are expressed and secreted. The cell culture medium can be essentially free of cells, for example, by removing them by centrifugation or filtration. A composition for degrading cellulose can be produced by culturing recombinant cells described above under conditions in which the enzymes (e.g., GH61, EG, CBH and/or BGL proteins) are expressed and secreted, optionally removing the cells from the medium, and optionally enriching the medium to increase the concentration of proteins.

X. Use of GH61 Proteins in Saccharification Reactions

Saccharification reactions may be carried out by exposing a cellulosic substrate (e.g., pretreated biomass) to a GH61 protein and cellulases, which work in concert to hydrolyze cellulose and produce fermentable sugars.

Typically, the cellulases include at least one endoglucanase (EG), at least one β-glucosidase (BGL), at least one Type 1 cellobiohydrolase (CBH1), and/or at least one Type 2 cellobiohydrolase (CBH2).

The cells and compositions of the invention (including culture broth or cell lysates) may be used in the production of fermentable sugars from cellulosic biomass. The biomass substrate may be converted to a fermentable sugar by (a) optionally pretreating a cellulosic substrate to increase its susceptibility to hydrolysis; (b) contacting the optionally pretreated cellulosic substrate of step (a) with a composition, culture medium or cell lysate containing GH61 protein and cellulases under conditions suitable for the production of cellobiose and fermentable sugars (e.g., glucose).

In one embodiment, to carry out a saccharification reaction, each of the GH61 proteins and cellulase enzymes referred to above may be partially or substantially purified, and the purified proteins are combined with the cellulosic substrate. In another embodiment the various individual proteins are recombinantly expressed in different cells, and the media containing the secreted proteins are added to the biomass.

The compositions may be reacted with the substrate at a temperature in the range of about 25° C. to about 110° C., about 30° C. to about 90° C., about 30° C. to about 80° C., about 40° C. to about 80° C., about 35° C. to about 75° C., about 55° C. to 100° C. or to about 90° C. The process may be carried out at a pH in a range from about pH 3.0 to about 8.5, about pH 3.5 to about 8.5, about pH 4.0 to about 7.5, about pH 4.0 to about 7.0 and about pH 4.0 to about 6.5. The reaction times for converting a particular biomass substrate to a fermentable sugar may vary but the optimal reaction time can be readily determined. Exemplary reaction times may be in the range of from about 1 to about 240 hours, from about 5 to about 180 hours and from about 10 to about 150 hours. For example, the incubation time may be at least 1 hr, at least 5 h, at least 10 h, at least 15 h, at least 25 h, at least 50 h, at least 100 h, or at least 180 h.

In some embodiments, GH61 polypeptides of the present invention is used in combination with other optional ingredients such as at least one buffer or surfactant. In some embodiments, at least one buffer is used with the GH61 polypeptide of the present invention (optionally combined with other enzymes) to maintain a desired pH within the solution in which the GH61 is employed. Suitable buffers are well known in the art. In some embodiments, at least one surfactant is used in with the GH61 of the present invention. Divalent metal cations (e.g., $Cu^{++}$, $Mn^{++}$, $Co^{++}$, $Mg^{++}$, and $Ca^{++}$ at concentrations of 0.001 to 50 mM, 5 μM to 1 mM, 10-50 μM or 10-20 μM) may be included in the reaction.

Exemplary combinations of GH61 protein and cellulases include: GH61 protein with one or more endoglucanase (EG); GH61 protein with one or more β-glucosidase (BGL); GH61 protein with one or more Type 1 cellobiohydrolase (CBH1); or GH61 protein with one or more Type 2 cellobiohydrolase (CBH2). Other combinations are GH61 protein with EG and BGL; GH61 protein with EG and CBH1; GH61 protein with EG and CBH2; GH61 protein with BGL and CBH1; GH61 protein with BGL and CBH2, or GH61 protein with CBH1 and CBH2. Other combinations are GH61 protein with EG, BGL, and CBH1; GH61 protein with EG, BGL, and CBH2; GH61 protein with EG, CBH1, CBH2; GH61 protein with BGL, CBH1, and CBH2; and GH61 protein with all of EG, BGL, CBH1, and CBH2. Other enzymes listed in this disclosure may be included in any one or more of these combinations.

In some embodiments, the enzyme mixture comprises an isolated GH61 as provided herein and at least one or more of an isolated cellobiohydrolase type 1a such as a CBH1a, an isolated CBH2b, an isolated endoglucanase (EG) such as a type 2 endoglucanase (EG2) or a type 1 endoglucanase (EG1), and/or an isolated 3-glucosidase (BGL). In some embodiments, at least 5%, at least 10%, at last 15%, at least 20%, at least 25%, at least 30%, at least 35%, at least 40%, at least 45%, or at least 50% of the enzyme mixture is GH61. In some embodiments, the enzyme mixture further comprises a cellobiohydrolase type 1a (e.g., CBH1a), and GH61, wherein the enzymes together comprise at least 25%, at least 30%, at least 35%, at least 40%, at least 45%, at least 50%, at least 55%, at least 60%, at least 65%, at least 70%, at least 75%, or at least 80% of the enzyme mixture. In some embodiments, the enzyme mixture further comprises a β-glucosidase (BGL), GH61, CBH2b, wherein the three enzymes together comprise at least 30%, at least 35%, at least 40%, at least 45%, at least 50%, at least 55%, at least 60%, at least 65%, at least 70%, at least 75%, at least 80%, or at least 85% of the enzyme mixture. In some embodiments, the enzyme mixture further comprises an endoglucanase (EG), GH61, CBH2b, CBH1a, BGL, wherein the five enzymes together comprise at least 35%, at least 40%, at least 45%, at least 50%, at least 55%, at least 60%, at least 65%, at least 70%, at least 75%, at least 80%, at least 85%, or at least 90% of the enzyme mixture. In some embodiments, the enzyme mixture comprises GH61, CBH2b, CBH1, BGL, and at least one EG, in any suitable proportion for the desired reaction.

In some embodiments, the enzyme mixture composition comprises isolated cellulases in the following proportions by weight (wherein the total weight of the cellulases is 100%): about 20%-10% of BGL, about 30%-25% of CBH1a, about 10%-30% of GH61, about 20%-10% of EG1b, and about 20%-25% of CBH2b. In some embodiments, the enzyme mixture composition comprises isolated cellulases in the following proportions by weight: about 20%-10% of GH61, about 25%-15% of BGL, about 20%-30% of CBH1a, about 10%-15% of EG, and about 25%-30% of CBH2b. In some embodiments, the enzyme mixture composition comprises isolated cellulases in the following proportions by weight: about 30%-20% of GH61, about 15%-10% of BGL, about 25%-10% of CBH1a, about 25%-10% of CBH2b, about 15%-10% of EG. In some embodiments, the enzyme mixture composition comprises isolated cellulases in the following proportions by weight: about 40-30% of GH61, about 15%-10% of BGL, about 20%-10% of CBH1a, about 20%-10% of CBH2b, and about 15%-10% of EG.

In some embodiments, the enzyme mixture composition comprises isolated cellulases in the following proportions by weight: about 50-40% of GH61, about 15%-10% of BGL, about 20%-10% of CBH1a, about 15%-10% of CBH2b, and about 10%-5% of EG. In some embodiments, the enzyme mixture composition comprises isolated cellulases in the following proportions by weight: about 10%-15% of GH61, about 20%-25% of BGL, about 30%-20% of CBH1a, about 15%-5% of EG, and about 25%-35% of CBH2b. In some embodiments, the enzyme mixture composition comprises isolated cellulases in the following proportions by weight: about 15%-5% of GH61, about 15%-10% of BGL, about 45%-30% of CBH1a, about 25%-5% of EG1b, and about 40%-10% of CBH2b. In some embodiments, the enzyme mixture composition comprises isolated cellulases in the following proportions by weight: about 10% of GH61, about 15% of BGL, about 40% of CBH1a, about 25% of EG, and about 10% of CBH2b.

In some embodiments, the enzyme component comprises more than one CBH2b, CBH1a, EG, BGL, and/or GH61 enzyme (e.g., 2, 3 or 4 different enzymes), in any suitable combination. In some embodiments, an enzyme mixture composition of the invention further comprises at least one additional protein and/or enzyme. In some embodiments, enzyme mixture compositions of the present invention further comprise at least one additional enzyme other than the GH61, BGL, CBH1a, GH61, and/or CBH. In some embodiments, the enzyme mixture compositions of the invention further comprise at least one additional cellulase, other than the GH61, BGL, CBH1a, GH61, and/or CBH variant recited herein. In some embodiments, the GH61 polypeptide of the invention is also present in mixtures with non-cellulase enzymes that degrade cellulose, hemicellulose, pectin, and/or lignocellulose, and/or other enzymes described hereinbelow.

Exemplary *M. thermophila* Embodiments

For illustration and not limitation, the following exemplary embodiments are provided:

One embodiment of the invention is a host cell which is a *M. thermophila* cell that expresses a recombinant protein comprising SEQ ID NO:1-30, comprising a secreted portion of the GH61 protein, comprising a amino-terminal truncated portion of the GH61 protein, and biologically active variants thereof. In some cases the cell expresses a GH61 selected from SEQ. ID NOs:3 to 12 or the corresponding secreted protein, or a GH61 selected from SEQ ID NOs:13 to 25 or the corresponding secreted protein.

The invention provides a cell that comprises a recombinant nucleic acid sequence encoding a GH61 protein In some aspects, the invention provides a cell that comprises a recombinant nucleic acid sequence encoding a protein with at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:2, or at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to the secreted portion of any one of SEQ ID NOs:1 to 30, comprising a secreted portion of the GH61 protein (e.g., SEQ ID NO:2), comprising a amino-terminal truncated portion of the GH61 protein, and biologically active variants thereof. The recombinant nucleic acid sequence may encode a protein with at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to a GH61 protein listed in TABLE 1 or TABLE 2.

The nucleic acid may comprise the nucleotide sequence shown in any of SEQ. ID NOs:31 to 59, or a fragment thereof, or a nucleic acid that hybridizes to SEQ ID NOS:31-59 (or the exactly complementary sequence) under stringent conditions (i.e., medium-high, high, or very high stringency) conditions, and which encodes a polypeptide with GH61 activity. Alternatively, the nucleic acid may encode a polynucleotide that is at least about 70%, at least about 80%, at least about 90%, or at least about 95%, or at least 99% identical to any of such sequences or fragments, wherein the nucleic acid encodes and can be expressed to provide a polypeptide with GH61 activity. Optionally, such nucleic acid sequences may be codon optimized for expression in a particular species, such as a yeast, as described elsewhere in this disclosure.

In one embodiment of the invention, a host cell expresses at least one recombinant GH61 comprising any one of SEQ ID NOs:1 to 30, and/or at least one recombinant GH61 protein having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NOS:1 to 25; and also expresses:
 a) a recombinant EG protein with at least about 70%, at least about 75%, at least about 80%, at least about 85%, sometimes at least about 90%, and sometimes at least about 95% sequence identity to *M. thermophila* EG2a (SEQ ID NO: 65); and/or
 b) a recombinant CBH1a protein with at least about 70%, at least about 75%, at least about 80%, at least about 85%, sometimes at least about 90%, and sometimes at least about 95% sequence identity to SEQ ID NO:63 or 67; and/or
 c) a recombinant CBH2b protein with at least about 70%, at least about 75%, at least about 80%, at least about 85%, sometimes at least about 90%, and sometimes at least about 95% sequence identity to SEQ ID NO:64 or 68; and/or
 d) a recombinant BGL protein with at least about 70%, at least about 75%, at least about 80%, at least about 85%, sometimes at least about 90%, and sometimes at least about 95% sequence identity to SEQ ID NO:60, 61, 62, or 66.

In certain embodiments of the invention, the cell expresses at least one, at least two, at least three (e.g., b-d) or all four of (a), (b), (c), and (d).

XI. Saccharification in the Absence of Exogenous EG

In one aspect, the invention provides a method of hydrolyzing a cellulosic substrate comprising combining a GH61 protein with β-glucosidase (BGL) and cellobiohydrolase (CBH) enzymes, in a composition substantially fee of endoglucanase (EG). It will be appreciated that EG-like activity contributed by a GH61 protein is not considered an endogluconase. As illustrated in the example below, a saccharification reaction may be carried out in the presence of GH61 protein, a β-glucosidase, and one or more cellobiohydrolase enzymes, without recombinant EG, or without added EG, or substantially free of EG. Either Type I or Type II cellobiohydrolase or both may be present. In the absence of EG, GH61 can increase the yield of a saccharification reaction by BGL and a single CBH by over 1.5- or 1.7-fold.

A reaction is said to be "substantially free" of endoglucanse, if (a) there is no detectable endoglucanse activity in the reaction, or (b) the amount of that EG enzyme present is less than 2%, often less than 1%, often less than 0.5%, often less than 0.2%, and often less than 0.1% (wt/wt) of the amount of BGL present, or (c) the amount of that EG enzyme present is less than 2%, often less than 1%, often less than 0.5%, often less than 0.2%, and often less than 0.1% (wt/wt) of the amount of CBH present, or (d) the amount of that EG enzyme present is less than 2%, often less than 1%, often less than 0.5%, often less than 0.2%, and often less than 0.1% (wt/wt) of the amount of GH61 present, or (e) or (d) the amount of that EG enzyme present is less than 2%, often less than 1%, often less than 0.5%, often less than 0.2%, and often less than 0.1% (wt/wt) of the amount of total cellulase present.

XII. Compositions Comprising Other Enzymes

Additional enzymes that can act in concert to hydrolyze a cellulosic substrate (such as cellulose or a starch-containing substrate) in the saccharification process may be included in the compositions of or incorporated in the methods of, this invention. Such enzymes include, but are not limited to xylanases hemicellulases, amylases, esterases, and cellulases, α-glucosidases, aminopeptidases, carbohydrases, carboxypeptidases, catalases, chitinases, cutinases, cyclodextrin glycosyltransferases, deoxyribonucleases, α-galactosidases, β-galactosidases, glucoamylases, glucocerebrosidases, invertases, laccases, lipases, mannosidases, mutanases, oxidases, pectinolytic enzymes, peroxidases, phospholipases, phytases, polyphenoloxidases, ribonucleases, and trans-glutaminases, as well as other cellulases (e.g., type 1 and type 2 cellobiohydrolases, endoglucanses, and β-glucosidases). Cellulase mixtures for efficient enzymatic hydrolysis of cellulose are known (See e.g., Viikari et al., 2007, *Adv. Biochem. Eng. Biotechnol.,* 108:121-45; and US Pat. Publns. 2009/0061484; US 2008/0057541; and US 2009/0209009, each of which is incorporated herein by reference). In some embodiments, mixtures of purified naturally occurring or recombinant enzymes are combined with cellulosic feedstock or a product of cellulose hydrolysis. In some embodiments, one or more cell populations, each producing one or more naturally occurring or recombinant cellulases, are combined with cellulosic feedstock or a product of cellulose hydrolysis.

In some additional embodiments, the present invention provides at least one GH61 and at least one endoxylanase. Endoxylanases (EC 3.2.1.8) catalyze the endohydrolysis of 1,4-β-D-xylosidic linkages in xylans. This enzyme may also be referred to as endo-1,4-β-xylanase or 1,4-β-D-xylan xylanohydrolase. In some embodiments, an alternative is EC 3.2.1.136, a glucuronoarabinoxylan endoxylanase, an enzyme that is able to hydrolyze 1,4 xylosidic linkages in glucuronoarabinoxylans.

In some additional embodiments, the present invention provides at least one GH61 and at least one β-xylosidase. 3-xylosidases (EC 3.2.1.37) catalyze the hydrolysis of 1,4-β-D-xylans, to remove successive D-xylose residues from the non-reducing termini. This enzyme may also be referred to as xylan 1,4-β-xylosidase, 1,4-O-D-xylan xylohydrolase, exo-1,4-β-xylosidase or xylobiase.

In some additional embodiments, the present invention provides at least one GH61 and at least one α-L-arabinofuranosidase. α-L-arabinofuranosidases (EC 3.2.1.55) catalyze the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

In some additional embodiments, the present invention provides at least one GH61 and at least one alpha-glucuronidase. Alpha-glucuronidases (EC 3.2.1.139) catalyze the hydrolysis of an alpha-D-glucuronoside to D-glucuronate and an alcohol.

In some additional embodiments, the present invention provides at least one GH61 and at least one acetylxylanesterase. Acetylxylanesterases (EC 3.1.1.72) catalyze the hydrolysis of acetyl groups from polymeric xylan, acetylated xylose, acetylated glucose, alpha-napthyl acetate, and p-nitrophenyl acetate.

In some additional embodiments, the present invention provides at least one GH61 and at least one feruloyl esterase. Feruloyl esterases (EC 3.1.1.73) have 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

In some additional embodiments, the present invention provides at least one GH61 and at least one coumaroyl esterase. Coumaroyl esterases (EC 3.1.1.73) catalyze a reaction of the form: coumaroyl-saccharide+$H_2O$=coumarate+saccharide. In some embodiments, the saccharide is an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73 so may also be referred to as a feruloyl esterase.

In some additional embodiments, the present invention provides at least one GH61 and at least one alpha-galactosidase. Alpha-galactosidases (EC 3.2.1.22) catalyze the hydrolysis of terminal, non-reducing α-D-galactose residues in α-D-galactosides, including galactose oligosaccharides, galactomannans, galactans and arabinogalactans. This enzyme may also be referred to as melibiase.

In some additional embodiments, the present invention provides at least one GH61 and at least one beta-galactosidase. Beta-galactosidases (EC 3.2.1.23) catalyze the hydrolysis of terminal non-reducing 3-D-galactose residues in β-D-galactosides. In some embodiments, the polypeptide is also capable of hydrolyzing α-L-arabinosides. This enzyme may also be referred to as exo-(1→4)-β-D-galactanase or lactase.

In some additional embodiments, the present invention provides at least one GH61 and at least one beta-mannanase. Beta-mannanases (EC 3.2.1.78) catalyze the random hydrolysis of 1,4-β-D-mannosidic linkages in mannans, galactomannans and glucomannans. This enzyme may also be referred to as mannan endo-1,4-β-mannosidase or endo-1,4-mannanase.

In some additional embodiments, the present invention provides at least one GH61 and at least one beta-mannosidase. Beta-mannosidases (EC 3.2.1.25) catalyze the hydrolysis of terminal, non-reducing β-D-mannose residues in β-D-mannosides. This enzyme may also be referred to as mannanase or mannase.

In some additional embodiments, the present invention provides at least one GH61 and at least one glucoamylase. Glucoamylases (EC 3.2.1.3) catalyzes the release of D-glucose from non-reducing ends of oligo- and poly-saccharide molecules. Glucoamylase is also generally considered a type of amylase known as amylo-glucosidase.

In some additional embodiments, the present invention provides at least one GH61 and at least one amylase. Amylases (EC 3.2.1.1) are starch cleaving enzymes that degrade starch and related compounds by hydrolyzing the α-1,4 and/or α-1,6 glucosidic linkages in an endo- or an exo-acting fashion. Amylases include α-amylases (EC 3.2.1.1); β-amylases (3.2.1.2), amylo-amylases (EC 3.2.1.3), α-glucosidases (EC 3.2.1.20), pullulanases (EC 3.2.1.41), and isoamylases (EC 3.2.1.68).

In some embodiments, the amylase is an α-amylase. In some embodiments one or more enzymes that degrade pectin are included in enzyme mixtures that comprise GH61 of the present invention.

A pectinase catalyzes the hydrolysis of pectin into smaller units such as oligosaccharide or monomeric saccharides. In some embodiments, the enzyme mixtures comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase and/or a xylogalacturonase.

In some additional embodiments, the present invention provides at least one GH61 and at least one endo-polygalacturonase. Endo-polygalacturonases (EC 3.2.1.15) catalyze the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide)glycanohydrolase.

In some additional embodiments, the present invention provides at least one GH61 and at least one pectin methyl esterase. Pectin methyl esterases (EC 3.1.1.11) catalyze the reaction: pectin+n H$_2$O=n methanol+pectate. The enzyme may also been known as pectinesterase, pectin demethoxylase, pectin methoxylase, pectin methylesterase, pectase, pectinoesterase or pectin pectylhydrolase.

In some additional embodiments, the present invention provides at least one GH61 and at least one endo-galactanase. Endo-galactanases (EC 3.2.1.89) catalyze the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

In some additional embodiments, the present invention provides at least one GH61 and at least one pectin acetyl esterase. Pectin acetyl esterases catalyze the deacetylation of the acetyl groups at the hydroxyl groups of GalUA residues of pectin.

In some additional embodiments, the present invention provides at least one GH61 and at least one endo-pectin lyase. Endo-pectin lyases (EC 4.2.2.10) catalyze the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin transeliminase; endo-pectin lyase, polymethylgalacturonic transeliminase, pectin methyltranseliminase, pectolyase, PL, PNL or PMGL or (1→4)-6-O-methyl-α-D-galacturonan lyase.

In some additional embodiments, the present invention provides at least one GH61 and at least one pectate lyase. Pectate lyases (EC 4.2.2.2) catalyze the eliminative cleavage of (1-4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→)-α-D-galacturonan lyase.

In some additional embodiments, the present invention provides at least one GH61 and at least one alpha-rhamnosidase. Alpha-rhamnosidases (EC 3.2.1.40) catalyze the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

In some additional embodiments, the present invention provides at least one GH61 and at least one exo-galacturonase. Exo-galacturonases (EC 3.2.1.82) hydrolyze pectic acid from the non-reducing end, releasing digalacturonate. The enzyme may also be known as exo-poly-α-galacturonosidase, exopolygalacturonosidase or exopolygalacturanosidase.

In some additional embodiments, the present invention provides at least one GH61 and at least one galacturan 1,4-alpha galacturonidase. Galacturan 1,4-alpha galacturonidases (EC 3.2.1.67) catalyze a reaction of the following type: (1,4-α-D-galacturonide)n+H2O=(1,4-α-D-galacturonide)n−i+D-galacturonate. The enzyme may also be known as poly [1→4) alpha-D-galacturonide]galacturonohydrolase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

In some additional embodiments, the present invention provides at least one GH61 and at least one exopolygalacturonate lyase. Exopolygalacturonate lyases (EC 4.2.2.9) catalyze eliminative cleavage of 4-(4-deoxy-α-D-galact-4-enuronosyl)-D-galacturonate from the reducing end of pectate (i.e. de-esterified pectin). This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

In some additional embodiments, the present invention provides at least one GH61 and at least one rhamnogalacturonanase. Rhamnogalacturonanases hydrolyze the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

In some additional embodiments, the present invention provides at least one GH61 and at least one rhamnogalacturonan lyase. Rhamnogalacturonan lyases cleave α-L-

Rhap-(1→4)-α-D-GalpA linkages in an endo-fashion in rhamnogalacturonan by beta-elimination.

In some additional embodiments, the present invention provides at least one GH61 and at least one rhamnogalacturonan acetyl esterase. Rhamnogalacturonan acetyl esterases catalyze the deacetylation of the backbone of alternating rhamnose and galacturonic acid residues in rhamnogalacturonan.

In some additional embodiments, the present invention provides at least one GH61 and at least one rhamnogalacturonan galacturonohydrolase. Rhamnogalacturonan galacturonohydrolases hydrolyze galacturonic acid from the non-reducing end of strictly alternating rhamnogalacturonan structures in an exo-fashion. This enzyme may also be known as xylogalacturonan hydrolase.

In some additional embodiments, the present invention provides at least one GH61 and at least one endo-arabinanase. Endo-arabinanases (EC 3.2.1.99) catalyze endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

In some additional embodiments, the present invention provides at least one GH61 and at least one enzyme that participates in lignin degradation in an enzyme mixture. Enzymatic lignin depolymerization can be accomplished by lignin peroxidases, manganese peroxidases, laccases and cellobiose dehydrogenases (CDH), often working in synergy. These extracellular enzymes are often referred to as "lignin-modifying enzymes" or "LMEs." Three of these enzymes comprise two glycosylated heme-containing peroxidases: lignin peroxidase (LIP); Mn-dependent peroxidase (MNP); and, a copper-containing phenoloxidase laccase (LCC).

In some additional embodiments, the present invention provides at least one GH61 and at least one laccase. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

In some additional embodiments, the present invention provides at least one GH61 and at least one Mn-dependent peroxidase. The enzymatic activity of Mn-dependent peroxidase (MnP) in is dependent on Mn2+. Without being bound by theory, it has been suggested that the main role of this enzyme is to oxidize Mn2+ to Mn3+ (See e.g., Glenn et al., Arch. Biochem. Biophys., 251:688-696 [1986]). Subsequently, phenolic substrates are oxidized by the Mn3+ generated.

In some additional embodiments, the present invention provides at least one GH61 and at least one lignin peroxidase. Lignin peroxidase is an extracellular heme that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalyzed oxidation of lignin in vivo (See e.g., Harvey, et al., *FEBS Lett.*, 195:242-246 [1986]).

In some additional embodiments, the present invention provides at least one GH61 and at least one protease, amylase, glucoamylase, and/or a lipase that participates in cellulose degradation.

As used herein, the term "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention. Some specific types of proteases include, cysteine proteases including pepsin, papain and serine proteases including chymotrypsins, carboxypeptidases and metalloendopeptidases.

As used herein, the term "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

In some additional embodiments, the present invention provides at least one GH61 and at least one expansin or expansin-like protein, such as a swollenin (See e.g., Salheimo et al., *Eur. J. Biochem.*, 269:4202-4211 [2002]) or a swollenin-like protein. Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. In some embodiments, an expansin-like protein or swollenin-like protein comprises one or both of such domains and/or disrupts the structure of cell walls (such as disrupting cellulose structure), optionally without producing detectable amounts of reducing sugars.

In some additional embodiments, the present invention provides at least one GH61 and at least one polypeptide product of a cellulose integrating protein, scaffoldin or a scaffoldin-like protein, for example CipA or CipC from *Clostridium thermocellum* or *Clostridium* cellulolyticum respectively. Scaffoldins and cellulose integrating proteins are multi-functional integrating subunits which may organize cellulolytic subunits into a multi-enzyme complex. This is accomplished by the interaction of two complementary classes of domain (i.e. a cohesion domain on scaffoldin and a dockerin domain on each enzymatic unit). The scaffoldin subunit also bears a cellulose-binding module that mediates attachment of the cellulosome to its substrate. A scaffoldin or cellulose integrating protein for the purposes of this invention may comprise one or both of such domains.

In some additional embodiments, the present invention provides at least one GH61 and at least one cellulose-induced protein or modulating protein, for example as encoded by cip1 or cip2 gene or similar genes from *Trichoderma reesei* (See e.g., Foreman et al., *J. Biol. Chem.*, 278:31988-31997 [2003]).

In some additional embodiments, the present invention provides at least one GH61 and at least one member of each of the classes of the polypeptides described above, several members of one polypeptide class, or any combination of these polypeptide classes to provide enzyme mixtures suitable for various uses.

In some embodiments, the enzyme mixture comprises other types of cellulases, selected from but not limited to cellobiohydrolase, endoglucanase, β-glucosidase, and glycoside hydrolase 61 protein (GH61) cellulases. These enzymes may be wild-type or recombinant enzymes. In some embodiments, the cellobiohydrolase is a type 1 cellobiohydrolase (e.g., a *T. reesei* cellobiohydrolase I). In some embodiments, the endoglucanase comprises a catalytic domain derived from the catalytic domain of a *Streptomyces avermitilis* endoglucanase (See e.g., US Pat. Appln. Pub. No. 2010/0267089, incorporated herein by reference). In some embodiments, the at least one cellulase is derived from *Acidothermus cellulolyticus, Thermobifida fusca, Humicola grisea, Myceliophthora thermophila, Chaetomium thermophilum, Acremonium* sp., *Thielavia* sp, *Trichoderma reesei, Aspergillus* sp., or a *Chrysosporium* sp. Cellulase enzymes of the cellulase mixture work together resulting in decrystallization and hydrolysis of the cellulose from a biomass substrate to yield fermentable sugars, such as but not limited to glucose.

Some cellulase mixtures for efficient enzymatic hydrolysis of cellulose are known (See e.g., Viikari et al., *Adv. Biochem. Eng. Biotechnol.*, 108:121-45 [2007]; and US Pat. Appln. Publn. Nos. US 2009/0061484, US 2008/0057541, and US 2009/0209009, each of which is incorporated herein by reference in their entireties). In some embodiments, mixtures of purified naturally occurring or recombinant enzymes are combined with cellulosic feedstock or a product of cellulose hydrolysis. Alternatively or in addition, one or more cell populations, each producing one or more naturally occurring or recombinant cellulases, are combined with cellulosic feedstock or a product of cellulose hydrolysis.

In some embodiments, the enzyme mixture comprises commercially available purified cellulases. Commercial cellulases are known and available (e.g., C2730 cellulase from *Trichoderma reesei* ATCC No. 25921 available from Sigma-Aldrich, Inc.; and C9870 ACCELLERASE® 1500, available from Genencor).

XIII. Cellulosic Substrate

Cellulosic substrates may be derived from any cellulose containing material, such as biomass derived from plants, animals, or microorganisms, and may include agricultural, industrial, and forestry residues, industrial and municipal wastes, and terrestrial and aquatic crops grown for energy purposes. "Cellulosic substrates" broadly encompasses any living or dead biological material that contains a polysaccharide substrate, including but not limited to cellulose, starch, other forms of long-chain carbohydrate polymers, and mixtures of such sources. It may or may not be assembled entirely or primarily from glucose or xylose, and may optionally also contain various other pentose or hexose monomers. Xylose is an aldopentose containing five carbon atoms and an aldehyde group. It is the precursor to hemicellulose, and is often a main constituent of biomass.

Cellulosic substrates are often provided as lignocellulose feedstocks which may be processed prior to hydrolysis by cellulases. As used herein, the term "lignocellulosic feedstock" refers to any type of plant biomass such as, but not limited to cultivated crops (e.g., grasses, including C4 grasses, such as switch grass, cord grass, rye grass, miscanthus, reed canary grass, or any combination thereof), sugar processing residues, for example, but not limited to baggase (e.g., sugar cane bagasse, beet pulp, or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the lignocellulosic feedstock comprises cellulosic waste material and/or forestry waste materials, including but not limited to, paper and pulp processing waste, newsprint, cardboard and the like. The biomass may also comprise transgenic plants that express ligninase and/or cellulase enzymes (US 2008/0104724 A1).

In some embodiments, the lignocellulosic feedstock comprises one species of fiber, while in some alternative embodiments, the lignocellulosic feedstock comprises a mixture of fibers that originate from different lignocellulosic feedstocks. In some other embodiments, the lignocellulosic feedstock comprises fresh lignocellulosic feedstock, partially dried lignocellulosic feedstock, fully dried lignocellulosic feedstock, and/or any combination thereof. In some embodiments, lignocellulosic feedstocks comprise cellulose in an amount greater than about 20%, more preferably greater than about 30%, more preferably greater than about 40% (w/w). For example, in some embodiments, the lignocellulosic material comprises from about 20% to about 90% (w/w) cellulose, or any amount therebetween, although in some embodiments, the lignocellulosic material comprises less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5% cellulose (w/w). Furthermore, in some embodiments, the lignocellulosic feedstock comprises lignin in an amount greater than about 10%, more typically in an amount greater than about 15% (w/w). In some embodiments, the lignocellulosic feedstock comprises small amounts of sucrose, fructose and/or starch.

The lignocellulosic feedstock is generally first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In some embodiments, at least 90% by weight of the particles produced from the size reduction have lengths less than between about 1/16 and about 4 in (the measurement may be a volume or a weight average length). In some embodiments, the equipment used to reduce the particle size reduction is a hammer mill or shredder. Subsequent to size reduction, the feedstock is typically slurried in water, as this facilitates pumping of the feedstock. In some embodiments, lignocellulosic feedstocks of particle size less than about 6 inches do not require size reduction. The biomass may optionally be pretreated to increase the susceptibility of cellulose to hydrolysis by chemical, physical and biological pretreatments (such as steam explosion, pulping, grinding, acid hydrolysis, solvent exposure, and the like, as well as combinations thereof).

In some embodiments, the feedstock is slurried prior to pretreatment. In some embodiments, the consistency of the feedstock slurry is between about 2% and about 30% and more typically between about 4% and about 15%. In some embodiments, the slurry is subjected to a water and/or acid soaking operation prior to pretreatment. In some embodiments, the slurry is dewatered using any suitable method to reduce steam and chemical usage prior to pretreatment. Examples of dewatering devices include, but are not limited to pressurized screw presses (See e.g., WO 2010/022511, incorporated herein by reference) pressurized filters and extruders.

As used herein, the terms "pretreated lignocellulosic feedstock," and "pretreated lignocellulose," refer to lignocellulosic feedstocks that have been subjected to physical and/or chemical processes to make the fiber more accessible and/or receptive to the actions of cellulolytic enzymes. Thus, "pretreated lignocellulosic feedstock," is an example of a "pretreated cellulosic substrate." In some embodiments, the pretreatment is carried out to hydrolyze hemicellulose, and/or a portion thereof present in the lignocellulosic feedstock to monomeric pentose and hexose sugars (e.g., xylose, arabinose, mannose, galactose, and/or any combination thereof). In some embodiments, the pretreatment is carried out so that nearly complete hydrolysis of the hemicellulose and a small amount of conversion of cellulose to glucose occurs. In some embodiments, an acid concentration in the aqueous slurry from about 0.02% (w/w) to about 2% (w/w), or any amount therebetween, is typically used for the treatment of the lignocellulosic feedstock. Any suitable acid finds use in these methods, including but not limited to, hydrochloric acid, nitric acid, and/or sulfuric acid. In some embodiments, the acid used during pretreatment is sulfuric acid. Steam explosion is one method of performing acid pretreatment of feedstock (See e.g., U.S. Pat. No. 4,461,648). Another method of pretreating the feedstock slurry involves continuous pretreatment (i.e., the lignocellulosic feedstock is pumped though a reactor continuously). This methods are well-known to those skilled in the art (See e.g., U.S. Pat. No. 7,754,457).

In some embodiments, alkali is used in the pretreatment. In contrast to acid pretreatment, pretreatment with alkali may not hydrolyze the hemicellulose component of the feedstock. Rather, the alkali reacts with acidic groups present on the hemicellulose to open up the surface of the substrate. In some embodiments, the addition of alkali alters the crystal structure of the cellulose so that it is more amenable to hydrolysis. Examples of alkali that find use in the pretreatment include, but are not limited to ammonia, ammonium hydroxide, potassium hydroxide, and sodium hydroxide. One method of alkali pretreatment is Ammonia Freeze Explosion, Ammonia Fiber Explosion or Ammonia Fiber Expansion ("AFEX" process; See e.g., U.S. Pat. Nos. 5,171,592; 5,037,663; 4,600,590; 6,106,888; 4,356,196; 5,939,544; 6,176,176; 5,037,663 and 5,171,592). During this process, the lignocellulosic feedstock is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. In some embodiments, the flashed ammonia is then recovered using methods known in the art. In alternative method, dilute ammonia pretreatment is utilized. The dilute ammonia pretreatment method utilizes more dilute solutions of ammonia or ammonium hydroxide than AFEX (See e.g., WO 2009/045651 and US 2007/0031953). This pretreatment process may or may not produce any monosaccharides.

An additional pretreatment process for use in the present invention includes chemical treatment of the feedstock with organic solvents, in methods such as those utilizing organic liquids in pretreatment systems (See e.g., U.S. Pat. No. 4,556,430; incorporated herein by reference). These methods have the advantage that the low boiling point liquids easily can be recovered and reused. Other pretreatments, such as the Organosolv™ process, also use organic liquids (See e.g., U.S. Pat. No. 7,465,791, which is also incorporated herein by reference). Subjecting the feedstock to pressurized water may also be a suitable pretreatment method (See e.g., Weil et al. (1997) *Appl. Biochem. Biotechnol.*, 68(1-2): 21-40, which is incorporated herein by reference).

In some embodiments, the pretreated lignocellulosic feedstock is processed after pretreatment by any of several steps, such as dilution with water, washing with water, buffering, filtration, or centrifugation, or any combination of these processes, prior to enzymatic hydrolysis, as is familiar to those skilled in the art. The pretreatment produces a pretreated feedstock composition (e.g., a "pretreated feedstock slurry") that contains a soluble component including the sugars resulting from hydrolysis of the hemicellulose, optionally acetic acid and other inhibitors, and solids including unhydrolyzed feedstock and lignin. In some embodiments, the soluble components of the pretreated feedstock composition are separated from the solids to produce a soluble fraction. In some embodiments, the soluble fraction, including the sugars released during pretreatment and other soluble components (e.g., inhibitors), is then sent to fermentation. However, in some embodiments in which the hemicellulose is not effectively hydrolyzed during the pretreatment one or more additional steps are included (e.g., a further hydrolysis step(s) and/or enzymatic treatment step(s) and/or further alkali and/or acid treatment) to produce fermentable sugars. In some embodiments, the separation is carried out by washing the pretreated feedstock composition with an aqueous solution to produce a wash stream and a solids stream comprising the unhydrolyzed, pretreated feedstock.

Alternatively, the soluble component is separated from the solids by subjecting the pretreated feedstock composition to a solids-liquid separation, using any suitable method (e.g., centrifugation, microfiltration, plate and frame filtration, cross-flow filtration, pressure filtration, vacuum filtration, etc.). Optionally, in some embodiments, a washing step is incorporated into the solids-liquids separation. In some embodiments, the separated solids containing cellulose, then undergo enzymatic hydrolysis with cellulase enzymes in order to convert the cellulose to glucose. In some embodiments, the pretreated feedstock composition is fed into the fermentation process without separation of the solids contained therein. In some embodiments, the unhydrolyzed solids are subjected to enzymatic hydrolysis with cellulase enzymes to convert the cellulose to glucose after the fermentation process. The pretreated lignocellulose is subjected to enzymatic hydrolysis with cellulase enzymes.

The pretreatment produces a pretreated feedstock composition (e.g., a pretreated feedstock slurry) that contains a soluble component including the sugars resulting from hydrolysis of the hemicellulose, optionally acetic acid and other inhibitors, and solids including unhydrolyzed feedstock and lignin.

The soluble components of the pretreated feedstock composition may be separated from the solids to produce a soluble fraction for use in a saccharification reaction.

The separation may be carried out by washing the pretreated feedstock composition with an aqueous solution to produce a wash stream, and a solids stream comprising the unhydrolyzed, pretreated feedstock. Alternatively, the soluble component is separated from the solids by subjecting the pretreated feedstock composition to a solids-liquid separation, using methods such as centrifugation, microfiltration, plate and frame filtration, cross-flow filtration, pressure filtration, and/or vacuum filtration. Optionally, a washing step may be incorporated into the solids-liquids separation. The separated solids containing cellulose may then be subjected to enzymatic hydrolysis with cellulase enzymes for conversion to glucose.

Suitably prepared lignocellulose can be subjected to enzymatic hydrolysis using one or more cellulase enzymes in the presence of one or more GH61 proteins or preparations according to this invention.

Hydrolysis of the hemicellulose and cellulose components of a lignocellulosic feedstock yields a lignocellulosic hydrolysate comprising xylose and glucose. Other sugars typically present include galactose, mannose, arabinose, fucose, rhamnose, or a combination thereof. Regardless of the means of hydrolyzing the lignocellulosic feedstock (full acid hydrolysis or chemical pretreatment with or without subsequent enzymatic hydrolysis), the xylose and glucose generally make up a large proportion of the sugars present.

If the lignocellulosic hydrolysate is a hemicellulose hydrolysate resulting from acid pretreatment, xylose will be the predominant sugar and lesser amounts of glucose will be present, because a modest amount of cellulose hydrolysis typically occurs during pretreatment. In this case, the xylose can make up between about 50 and about 90 wt % of the total carbohydrate content of the lignocellulosic hydrolysate. If the lignocellulosic hydrolysate results from sequential pretreatment and enzymatic hydrolysis of the lignocellulosic feedstock (i.e., without a solids separation step after pretreatment), the xylose can make up between about 30 and about 50 wt % of the total carbohydrate content. The relative amount of xylose present in the lignocellulosic hydrolysate will depend on the feedstock and the pretreatment that is employed.

The soluble components of the hydrolyzed substrate may be separated from the solids to produce a soluble fraction. The soluble fraction (including sugars released during hydrolysis, and sometimes inhibitors) may then be used for fermentation. If the hemicellulose is not effectively hydrolyzed during the pretreatment, it may be desirable to include a further hydrolysis step or steps with enzymes or further alkali or acid treatment to produce fermentable sugars.

XIV. Fermentation of Sugars

Fermentable sugars produced in saccharification reactions using GH61 proteins of the invention can be used to produce various end-products of interest.

In some embodiments, the sugars are used in a fermentation process to produce end-products. The term "fermentation" is used broadly to refer to the cultivation of a microorganism or a culture of microorganisms that use simple sugars, such as fermentable sugars, as an energy source to obtain a desired product. In a different embodiment, a cellulosic biomass may be treated with a composition of this invention to prepare an animal feed.

End-products include alcohols (e.g., ethanol, butanol), acetone, amino acids (e.g., glycine and lysine), organic acids (e.g., lactic acid, acetic acid, formic acid, citric acid, oxalic acid, 3-hydroxypropionic acid, acrylic acid, succinic acid, malic acid, fumaric acid or uric acid), glycerol, diols (such as 1,3 propanediol or butanediol), hydrocarbon with 1-20 carbon atoms (e.g., long chain esters), sugar alcohols (e.g., xylitol), fatty alcohols, a β-lactam, and other end-products.

Any suitable micro-organism may be used to convert sugar in the sugar hydrolysate to ethanol or other fermentation products. These include yeast from the genera *Saccharomyces, Hansenula, Pichia, Kluyveromyces* and *Candida*. Commercially available yeasts may be used, such as Turbo yeast, Ethanol Red® Safdistil®, Thermosacc®, Fermiol®, Fermivin® or Superstart™.

The yeast may be genetically engineered to ferment both hexose and pentose sugars to an end-product, including but not limited to ethanol. Alternatively, the yeast may be a strain that has been made capable of xylose and glucose fermentation by one or more non-recombinant methods, such as adaptive evolution or random mutagenesis and selection. For example, the fermentation may be performed with recombinant *Saccharomyces* yeast. The recombinant yeast may be a strain that has been made capable of xylose fermentation by recombinant incorporation of genes encoding xylose reductase (XR) and xylitol dehydrogenase (XDH) (U.S. Pat. Nos. 5,789,210, 5,866,382, 6,582,944 and 7,527,927 and EP 450 530) and/or gene(s) encoding one or more xylose isomerase (XI) (U.S. Pat. Nos. 6,475,768 and 7,622,284). In addition, the modified yeast strain may overexpress an endogenous or heterologous gene encoding xylulokinase (XK). Other yeast can ferment hexose and pentose sugars to at least one end-product, including but not limited to ethanol, such as yeast of the genera *Hansenula, Pichia, Kluyveromyces* and *Candida* (WO 2008/130603).

A typical temperature range for the fermentation of a sugar to ethanol using *Saccharomyces* spp. is between about 25° C. to about 37° C., although the temperature may be higher (up to 55° C.) if the yeast is naturally or genetically modified to be thermostable. The pH of a typical fermentation employing *Saccharomyces* spp. is between about 3 and about 6, depending on the pH optimum of the fermentation microorganism. The sugar hydrolysate may also be supplemented with additional nutrients required for growth and fermentation performance of the fermentation microorganism. For example, yeast extract, specific amino acids, phosphate, nitrogen sources, salts, trace elements and vitamins (Verduyn et al., 1992, *Yeast* 8(7):501-170, Jørgensen, 2009, *Appl Biochem Biotechnol,* 153:44-57 and Zhao et al., 2009, *Journal of Biotechnology,* 139:55-60). Typically the fermentation is conducted under anaerobic conditions, although aerobic or microaerobic conditions may also be used.

Thus, the invention provides processes for producing a fermentation product, wherein the method comprises: providing the recombinant host cells as provided herein, a fermentation medium comprising fermentable sugars such as glucose and/or xylose; and contacting the fermentation medium with the recombinant fungal host cells under conditions suitable for generating the fermentation product. In some embodiments, the processes further comprise the step of recovering the fermentation product. In some further embodiments, the fermenting step is carried out under microaerobic or aerobic conditions. In some embodiments, the fermenting step is carried out under anaerobic conditions. In some embodiments, the fermentation medium comprises product from a saccharification process.

The GH61 proteins and cellulases of the present invention may be utilized in any method used to generate alcohols or other biofuels from cellulose, and are not limited necessarily to those described herein. Two methods commonly employed are the separate saccharification and fermentation (SHF) method (see, Wilke et al., *Biotechnol. Bioengin.* 6:155-75 (1976)) or the simultaneous saccharification and fermentation (SSF) method disclosed for example in U.S. Pat. Nos. 3,990,944 and 3,990,945.

The SHF method of saccharification of the present invention comprises the steps of contacting a GH61 protein cellulase with a cellulose containing substrate to enzymatically break down cellulose into fermentable sugars (e.g., monosaccharides such as glucose), contacting the fermentable sugars with an alcohol-producing microorganism to produce alcohol (e.g., ethanol or butanol) and recovering the alcohol. In some embodiments, the method of consolidated bioprocessing (CBP) can be used, where the cellulase production from the host is simultaneous with saccharification and fermentation either from one host or from a mixed cultivation.

In addition to SHF methods, a SSF method may be used. In some cases, SSF methods result in a higher efficiency of alcohol production than is afforded by the SHF method (Drissen et al., Biocatalysis and Biotransformation 27:27-35 (2009). One disadvantage of SSF over SHF is that higher temperatures are required for SSF than for SHF.

In one embodiment, the present invention uses cellulase polypeptides that have higher thermostability than a wild-type cellulases.

EXAMPLES

Example 1

Identification of GH61 Proteins in M. thermophila

The genomic sequence of a M. thermophila wild-type fungal strain was obtained. The entire genome was analyzed to identify and evaluate protein coding regions. Twenty four proteins endogenous to the M. thermophila strain were selected based on factors including the presence of glycohydrolase family 61 (GH61) sequence motifs (Pfam domains). Pfam domains were identified using the software algorithm "PFAM v.24", developed by the Wellcome Trust Sanger Institute (Henrissat et al., 1995, Proc Natl Aced Sci USA 92:7090-94).

TABLE 1 provides the sequence of a GH61 pre-protein (SEQ ID NO:1) and the predicted secreted (mature) form (SEQ ID NO:2). The mature protein was designated "GH61a". TABLE 2 provides the sequences of other GH61 pre-proteins, with the predicted native signal peptide underlined. Two of the proteins in TABLE 2 are not predicted to have signal peptides.

Corresponding polynucleotide sequence numbering and domain structure analysis is shown in TABLE 3, below.

TABLE 3

Sequence Numbering and Domain Analysis

| Laboratory Designation | Protein SEQ ID NO | Nucleic Acid SEQ ID NO | Protein PFAM Domain |
|---|---|---|---|
| GH61a | 1 | 31 | GH61--CBM_1 |
| GH61l | 3 | 32 | Chitin_bind_3--GH61 |
| GH61m | 4 | 33 | GH61 |
| GH61n | 5 | 34 | GH61 |
| GH61o | 6 | 35 | GH61--GH61--CBM_1 |
| GH61p | 7 | 36 | GH61--GH61 |
| GH61q | 8 | 37 | GH61 |
| GH61r | 9 | 38 | GH61 |
| GH61s | 10 | 39 | GH61 |
| GH61t | 11 | 40 | GH61 |
| GH61u | 12 | 41 | GH61 |
| GH61v | 13 | 42 | GH61 |
| GH61w | 14 | 43 | GH61 |
| GH61x | 15 | 44 | GH61 |
| GH61b | 16 | 45 | GH61 |
| GH61c | 17 | 46 | GH61 |
| GH61d | 18 | 47 | GH61 |
| GH61e | 19 | 48 | GH61 |
| GH61f | 20 | 49 | GH61--CBM_1 |
| GH61g | 21 | 50 | GH61--CBM_1 |
| GH61h | 22 | 51 | GH61 |

TABLE 3-continued

Sequence Numbering and Domain Analysis

| Laboratory Designation | Protein SEQ ID NO | Nucleic Acid SEQ ID NO | Protein PFAM Domain |
|---|---|---|---|
| GH61i | 23 | 52 | GH61 |
| GH61j | 24 | 53 | GH61 |
| GH61k | 25 | 54 | GH61 |
| GH61p2 | 26 | 55 | GH61 |
| GH61q2 | 27 | 56 | GH61--GH61 |
| GH61r2 | 28 | 57 | GH61 |
| GH61t2 | 29 | 58 | GH61 |
| GH61e2 | 30 | 59 | GH61 |

SEQ ID NO:7 has a second GH61 domain (GH61-GH61), SEQ ID NOs:1,20,21 have the structure GH61-CBM1 (where "CBM1" is carbohydrate-binding module 1), SEQ ID NO:6 has the structure GH61-GH61-CBM1, SEQ ID NOs:4, 5, 8-19, and 22-25 have the structure GH61, SEQ ID NO:3 has the structure Chitin_bind_3-GH61 (where "Chitin_bind_3" is chitin-binding module 3). SEQ ID NOS:26-30 are alternative sequences corresponding to the genes encoding SEQ ID NOS:7-9, 11 and 19, respectively.

Example 2

Recombinant Expression of GH61 Proteins

Amongst the GH61 proteins identified in Example 1, certain exemplars were selected for expression based on predicted structural and functional aspects, such as whether a protein would be secreted from the cell, and its domain structure.

The six GH61 proteins listed in the following table each were cloned into an expression vector under the control of a CHI promoter (constitutive to the target cell) and transformed into a M. thermophila strain designated "CF-405" that has been adapted so as to be deficient in production of endogenous cellulases.

TABLE 4

Recombinantly expressed GH61 proteins

| Laboratory designation | Protein SEQ ID NO |
|---|---|
| GH61a | 2 |
| GH61o | 6 |
| GH61v | 13 |
| GH61x | 15 |
| GH61b | 16 |
| GH61e | 19, 30 |

Transformed cells expressing the recombinant GH61 protein were selected and seed cultures were prepared. The progeny cells were cultured for 5 days, and broth containing the secreted GH61 protein was collected ("GH61 broth").

Example 3

Cellulase-Enhancing Activity of GH61 Protein

Broth from cells expressing the recombinant GH61 protein comprising SEQ ID NO:2 was collected (Example 2), and the level of recombinant GH61 was quantitated by SDS-PAGE. Cellulase assays were conducted to determine whether addition of the GH61 protein enhanced hydrolysis of cellulosic material by cellulase enzymes.

Culture broth was collected from a culture of an *M. thermophila* strain designated "CF-402" that overexpresses β-glucosidase. Cellulose digestion assays were carried out using the broth with or without added GH61. Reactions were run in Costar 96 deep well plates in a total reaction volume of about 80 microliters. The reactions were run at 55° C. using as the cellulose-containing substrate preparations of wheat straw that had been pretreated under acid conditions (hereinafter referred to as "pretreated wheat straw"). 8.1 mg broth protein per gram substrate (0.81%) was added to each sample. In addition, samples had 0 (control), 0.22%, 0.44% or 0.66% GH61 broth protein added (final total broth protein concentration 0.81%, 1.03%, 1.25% or 1.47%). In control wells with no added GH61 broth, water was used to adjust volume so that the substrate load was equal in all wells. In other experiments, 6-10 mg broth protein per gram of substrate (0.6-1%) was added to each sample, to a final total broth protein concentration of 0.6-1.7%.

Figure 1B:
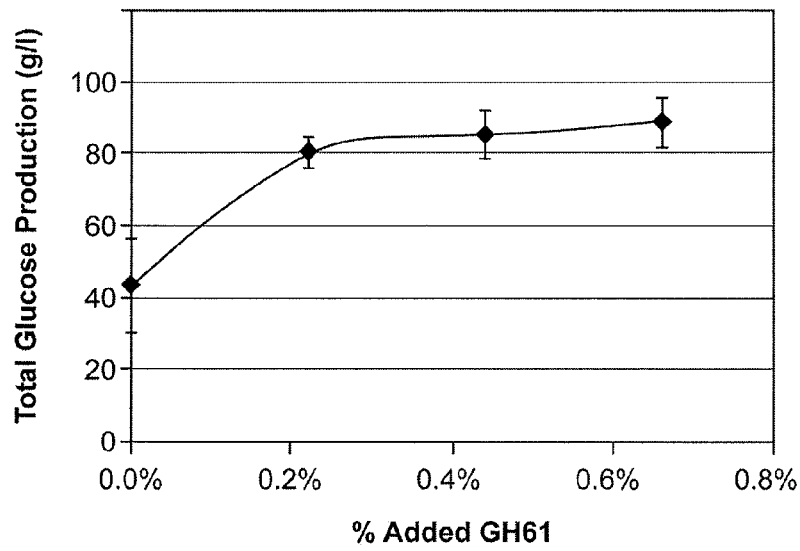
In FIG. 1(B), the data are plotted to show total glucose production.

FIG. 1 shows additional glucose yield over the control (broth without added GH61) after 48 hours of incubation. In FIG. 1(A), the percentage of improved yield over the control is shown. In FIG. 1(B), the data are plotted to show total glucose production.

Example 4

Over-Expression of GH61a in a CXP Strain

Construction of Recombinant GH61a Genes

Genomic DNA was isolated from the *M. thermophila* strain designated "CF-409". This strain endogenously produce endoglucanase, β-glucosidases, Type 1 cellobiohydrolase, and Type 2 cellobiohydrolase. The procedure was as follows. Hyphal inoculum was seeded into a growth medium and allowed to grow for 72 hours at 35° C. The mycelial mat was collected by centrifugation, washed, and 50 μL DNA extraction buffer (200 M Tris pH 8.0; 250 mM NaCl; 125 mM EDTA; 0.5% SDS) was added. The mycelia were ground with conical grinder, re-extracted with 250 μL extraction buffer, and the suspension was centrifuged. The supernatant was transferred to a new tube containing 300 μL isopropanol. DNA was collected by centrifugation, washed twice with 70% ethanol, and re-dissolved in 100 μL of deionized water.

The GH61a DNA sequence was amplified from CF-409 cells using primers PchiC1 GH61a_F and TcbhC1 GH61a_R. PCR reaction was performed by using the Phusion Polymerase, for 98° C. for 30", followed by 35 cycles of 98° C. for 10", 72° C. for 1' and final extension at 72° C. for 5'. The resulting product was cloned into pC1DX20PhR vector 3' to the chi1 promoter to create an expression vector that expressed the GH61a protein transcript under the control of the chi1 promoter (pC1DX20PhR-GH61a) using In-fusion cloning technique (In-Fusion Advantage™ PCR cloning kit with cloning enhancer, Clontech Cat. No. 639617 according to the manufacturer's instructions).

```
PchiC1GH61a_F
                                        SEQ ID NO: 69
tacttcttctccaccATGTCCAAGGCCTCTGCTCT TcbhC1GH61a_R
                                        SEQ ID NO: 70
ggatccgaattcttaTTACAAACACTGGGAGTACCA
```

Protoplast Preparation for CXP Transformation

*M. thermophila* cells ("CF-405", an Alp1 deleted-strain) were inoculated into 100 mL growth medium in an 500 mL Erlenmeyer flask using $10^6$ spores/mL. The culture was incubated for 24 hours at 35° C., 250 rpm. To harvest the mycelium, the culture was filtered over a sterile Myracloth™ filter (Calbiochem) and washed with 100 mL 1700 mosmol NaCl/CaCl$_2$ solution (0.6 M NaCl, 0.27 M CaCl$_2$.H$_2$O). The washed mycelia were transferred into a 50 mL tube and weighed. Caylase (20 mg/gram mycelia) was dissolved in 1700 mosmol NaCl/CaCl$_2$ and UV-sterilized for 90 sec. 3 ml of sterile Caylase solution was added into the washed mycelia containing tube and mixed. Further 15 mL of 1700 mosmol NaCl/CaCl$_2$ solution was added into the tube and mixed.

The mycelium/Caylase suspension was incubated at 30° C., 70 rpm for 2 hours. Protoplasts were harvested by filtering through a sterile Myracloth filter into a sterile 50 mL tube. 25 mL cold STC was added to the flow through and spun down at 2720 rpm for 10 min at 4° C. The pellet was re-suspended in 50 mL STC (1.2 M sorbitol, 50 mM CaCl$_2$.H$_2$O, 35 mM NaCl, 10 mM Tris-HCl) and centrifuged again. After the washing steps, the pellet was re-suspended in 1 mL STC.

Transformation

Into the bottom of a 15 mL sterile tube 2 μg plasmid DNA was pipetted and 1 μL aurintricarboxylic acid and 100 μL protoplast were added. The content was mixed and the protoplast with the DNA were incubated at room temperature for 25 min. 1.7 mL PEG4000 solution (60% PEG4000 [polyethylene glycol, average molecular weight 4000 Daltons], 50 mM CaCl$_2$.H$_2$O, 35 mM NaCl, 10 mM Tris-HCl) was added and mixed thoroughly. The solution was kept at room temperature for 20 min. The tube was filled with STC, mixed and centrifuged at 2500 rpm for 10 min at 4° C. The STC was poured off and the pellet was re-suspended in the remaining STC and plated on minimal media plates. The plates were incubated for 5 days at 35° C. Colonies were re-streaked and checked for the presence of the integrated plasmid. Several isolates were selected and tested for the expression of GH61a.

Transformation was carried out in CF405 strains. GH61a transformants were tested for GH61a over-expression on SDS-PAGE for the presence of the extra band which was confirmed by MS-MS analysis.

Example 5

Purification of GH61 Proteins from Cellulase Supernatant

In this experiment, GH61 protein activity was fractionated from the culture supernatant of an *M. thermophila* strain desingated "CF-401". CF-401 is a derivative of CDXF that has a deletion of CDH1 and CDH2 genes. This strain endogenously produces endoglucanase, β-glucosidases, Type 1 cellobiohydrolase, and Type 2 cellobiohydrolase.

To prepare for chromatography, the CF-401 whole cellulase supernatant was clarified by centrifugation at 12,000 rpm for 35 minutes. The supernatant was further filtered through 0.22 µm PES™ membrane, which was then concentrated and buffer-exchanged into 25 mM bis-tris buffer, pH 5.7. Saturated ammonium sulfate in 25 mM bis-tris was added to a final concentration of ~50 g/L protein in 0.9 M ammonium sulfate and 20-25 mM bis-tris. This solution was immediately loaded onto a Phenyl (High Sub) FF column (a fast-flow column packed with Phenyl-Sepharose™) and rinsed with 0.9 M ammonium sulfate in 25 mM bis-tris until the $A_{280}$ dropped to near baseline. Protein was eluted with a gradient of 0.9 M ammonium sulfate in 25 mM bis-tris to 0 M ammonium sulfate in 25 mM bis-tris, over about 10 column volumes. Fractions were collected (25 in this case) according to chromatogram peaks ($A_{280}$). To inhibit contaminant growth, $NaN_3$ was added to all fractions to a final concentration of 0.05%. After running an SDS-PAGE gel of each fraction, similar fractions were combined to create pools with a minimal set of components. Here, of the 25 fractions produced, 11 pools resulted. To prepare for the next column, each pool was concentrated down to ~150 mL using a tangential flow filtration unit equipped with 5 kDa MWCO PES™ membranes. The volume of the protein solution was then brought up to 500 mL with DI water, and concentrated back again to ~150 mL; this step was repeated 5× and effectively buffer-exchanged the solution.

Each of the 11 CF-401-derived pools was further fractionated with a Q column (quaternary ammonium ion exchange resin). After quantitation of total protein using a BCA (bicinnchroninic acid) assay, solutions of 50 g/L protein in 10 mM bis-tris pH 7.5 buffer were prepared for each pool. After application to the column, the resin was washed with 10 mM bis-tris, pH 7.5 until $A_{230}$ dropped to near baseline. Bound protein was then eluted with 1 M NaCl in 10 mM Bis-Tris, pH 7.5 using a stepwise gradient (5% over 10 minutes) and held at that concentration until the protein peak began to steadily drop. To analyze, an SDS-PAGE gel of each fraction was run, and fractions with similar compositions were pooled. Each of these second stage pools were then desalted/concentrated with tangential flow filtration.

In total, 79 pools of CF-401-derived enzymes were prepared in this way. To aid in loading in the saccharification assay, each the total protein for each pool was measured using the BCA protein assay.

Example 6

Use of GH61 Proteins to Promote Saccharification

GH61 enzymes fractionated according to the previous example were tested in saccharification in the presence of whole cellulase system obtained from a cell strain designated "CF-404". These cells were derived from the CF-401 strain and overexpress β-glucosidase. As a control experiment, 0.21% (generally 0.1-0.4%) of CF-404 was added to 0.61% (generally 0.6-1.5%) of CF-401. Thus, the total protein load was equal across all reactions. These mixtures are then incubated with 110 g/L glucan (pretreated wheat straw) at 55° C., pH 4.6-5, for 53 h. At the completion of the experiment, reactions were quenched by addition of 10 mM sulfuric acid. For glucose analysis, the samples were analyzed using an Agilent HPLC 1200 equipped with HPX-87H Ion exclusion column (300 mM×7.8 mM) with 5 mM H2SO4 as a mobile phase at a flow rate of 0.6 mL/min at 65° C. The retention time of the glucose was 9.1 minutes.

One example demonstrating improved glucose yield is shown in Table 5.

TABLE 5

Enhanced saccharification using GH61 fractions

| 0.21% GH61 supplementing 0.61% CF-404 | Glucose produced (g/L) | Corresponding SEQ ID NO: |
|---|---|---|
| GH61f | >30 | 20 |
| GH61a | >35 | 2 |
| GH61v | >35 | 13 |
| GH61p | >30 | 7 |
| GH61g | >30 | 21, 26 |
| GH61i | >35 | 23 |
| Control (CF-404) | 28.9 ± 0.66 | |

Partial protein sequence was obtained from mass spectrometry and compared with protein encoding sequences identified in the M. thermophila genome sequence (Example 1) by using BIFX alignment software available through the Bioinformatics Organization, Hudson Mass. Concordance with the known M. thermophila sequences is shown in the table above.

Example 7

Minimum Protein Combination to Convert Cellulose to Glucose

The M. thermophila enzymes, CBH1 and CBH2 were combined with various combinations of the GH61 proteins; GH61a, GH61f, and GH61p, and assayed at various relative concentrations for the ability to convert glucan to glucose. Culture supernatant from the strain CF-401 (which comprises both cellulases and GH61 proteins) was also assayed for comparison. For 110 g/L glucan, maximum possible glucose yields are approximately 135 to 145 g/L.

The saccharification reactions were carried out at 110 g/L glucan load of pretreated wheat straw at pH 5.0 at a temperature of 55° C. at 950 rpm in a total volume of 95 µL in high throughput (HTP) 96 deep well plates. 81 g/L xylose and 128 mM acetate were added to the pretreated wheat straw. Excess (in relation to glucan) β-glucosidase was also supplemented to relieve product inhibition from cellobiose. The whole cellulase (broth from CP-401 cells), as well as the individual enzymes were characterized by standard BCA assays for total protein quantification. Dose responses of the enzyme mixes were conducted by adding known total protein (calculated as wt of protein added/wt glucan). The total protein levels tested were 0.73, 1 and 3% (wt added protein/wt glucan). A dose response was measured at pH 5.0 and 55° C. for 72 hrs. The following combinations of the enzymes were used (in combination with BGL1):

a. CF-401 culture supernatant (Control; contains all 4 enzymes+GH61 proteins)
b. 50% (CBH1a+CBH2b)+50% GH61f
c. 50% (CBH1a+CBH2b)+50% GH61p
d. 50% (CBH1a+CBH2b)+25% GH61f+25% GH61p
e. 50% (CBH1a+CBH2b)+16.6% GH61a+16.6% GH61f+16.6% GH61$_p$ Reactions were quenched at 72 h by addition of 10 mM sulfuric acid. For glucose analysis, the samples were analyzed using an Agilent HPLC 1200 equipped with HPX-87H Ion exclusion column (300 mM×7.8 mM) with 5 mM $H_2SO_4$ as a mobile phase at a flow rate of 0.6 mL/min at 65° C. The retention time of the glucose was 9.1 minutes.

Figure 2:
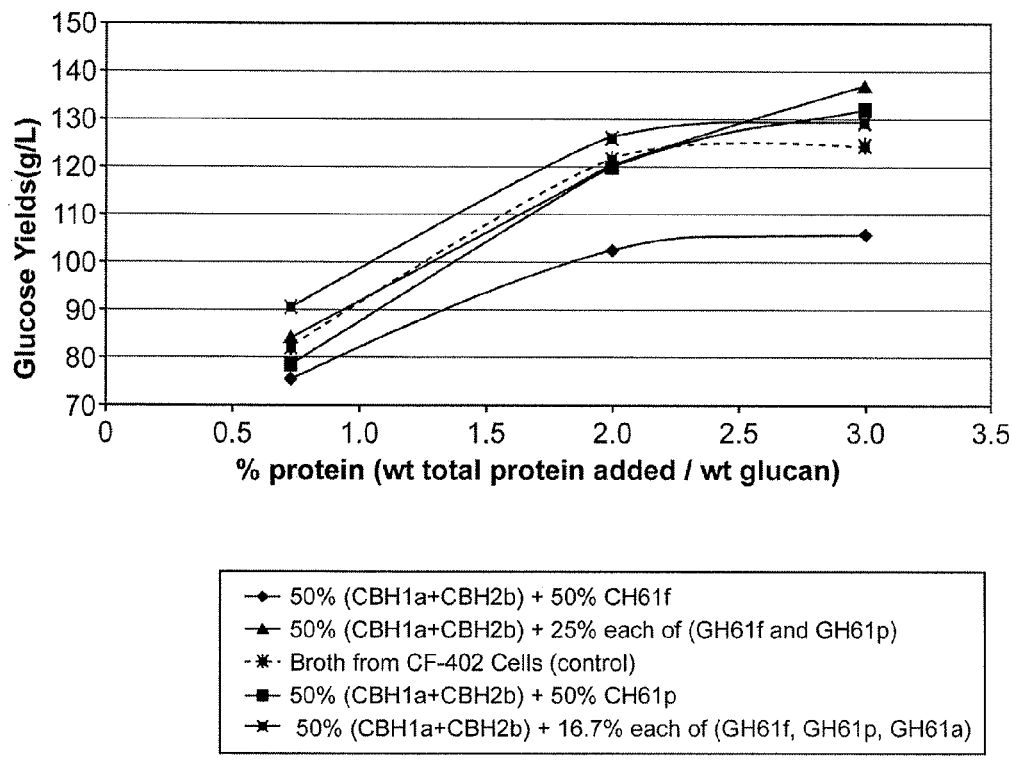
FIG. 2 is taken from an experiment using GH61 containing fractions isolated from culture broth of *M. thermophila*. GH61 proteins GH61f, GH61p, and/or GH61a were combined with CBH1a and CBH2b. These results demonstrate that an enzyme mixture comprising these components has sufficient enzyme activity for conversion of a cellulose substrate to glucose.

FIG. 2 shows the results. Cellulase enzymes CBH1 and CHB2 were combined with various GH61 proteins. The control experiment (dotted line) was culture supernatant from CF-401 cells which contains a plurality of cellulase enzymes and endogenous GH61 activity. Total protein load was added in the ratios specified on the figure.

These results establish that a minimal enzyme set is able to achieve similar glucose levels as the control: specifically, the cellulases CBH1 and CBH2, combined with one or more of GH61f, GH61p, and GH61a. All combinations generated higher glucose yields than CP-401 culture broth. Hence, it is possible to achieve maximum theoretical conversions using a minimal set of enzymes. This also demonstrates that the minimal enzyme mixture used here has all the components required for complete conversion of cellulose to glucose. However, it is contemplated that additional enzyme combinations will find use in saccharification processes.

Example 8

Synergy of GH61 Activity with Other CXP Derived Enzymes

This example describes an evaluation of GH61a for synergy with other *M. thermophila*-derived enzymes like CBH1a, CBH2b, and EG2.

Saccharification reactions were carried out at 110 g/L glucan load of pretreated wheat straw at pH 5.0 at a temperature of 55° C. at 950 rpm in a total volume of 95 µL in high throughput (HTP) 96 deep well plates. 81 g/L xylose and 128 mM acetate were added to the pretreated wheat straw. Excess β-glucosidase (wt/wt glucan) was also supplemented to relieve product inhibition from cellobiose. The whole cellulase as well as the individual enzymes was characterized by standard BCA assays for total protein quantification.

For an enzyme system comprising of two enzymes A and B, the degree of synergy was calculated by the following formula:

$$\text{Degree of Synergy} = \frac{\text{Glucose yield from the combination of GH61 and cellulase enzymes}}{\text{Glucose yield from GH61 + Glucose yield from cellulase enzymes}}$$

The glucose yield shown in the table is the yield obtained from the combination of GH61 and the enzymes. This is divided by the yield of glucose measured separately for GH61 and the enzyme mixture (not shown) to quantitate the synergy between the two.

The results show that GH61a is synergistic with all *M. thermophila*-derived enzyme systems tested. For complete conversion of cellulose to glucose, the presence of GH61a is beneficial.

Example 9

Using GH61a to Reduce Viscosity of Pretreated Wheat Straw

Purified GH61a from *M. thermophila* was evaluated to determine the enzyme function and to evaluate any endo-glucanase type activity for reduction in cellulose chain length, thereby enabling a reduction in viscosity.

GH61a alone and in combination with EG2 were tested for viscosity reduction on pretreated wheat straw at glucan load of 75 g/L glucan and at pH 5.0, 50° C. The viscosity reduction tests were carried out in a (30 minute run at 80 RPM) in a RVA-super4 viscometer (Newport Scientific, Australia) in a total weight of 21g.

Figure 3:
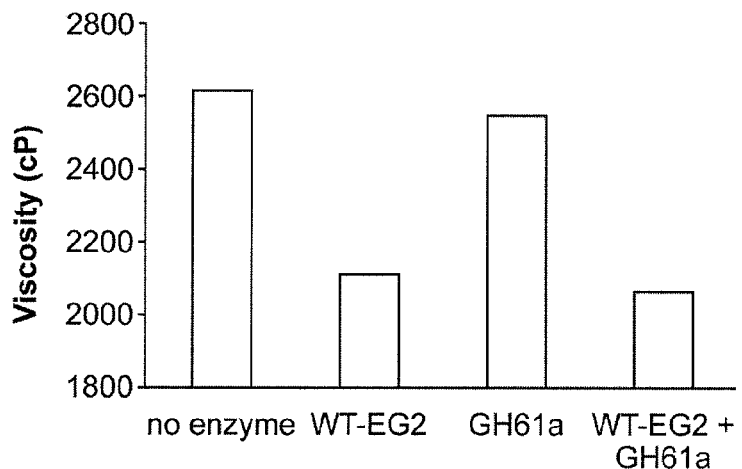
FIG. 3 shows the effect of GH61a protein on viscosity of cellulosic biomass.

FIG. 3 shows the results. Addition of 0.02% GH61a in relation to glucan exhibited approximately 2-3% viscosity reduction at pH 5, 50° C. In comparison, addition of 0.01% *M. thermophila* EG2 in relation to glucan exhibited approximately 19% viscosity reduction under the same conditions. With a combination of 0.02% GH61a and 0.01% EG2, the overall viscosity reduction was approximately 21%.

TABLE 6

Synergy of GH61a with *M. thermophila*-derived enzymes and enzyme mixtures

| Enzymes supplemented with GH61a | CBH1a % | CBH2b % | GH61a % | EG2% | Protein load (wt total protein added/wt glucan) | Glucose yield (g/L) | Degree of Synergy |
|---|---|---|---|---|---|---|---|
| CBH1a | 0.39% | — | 0.18% | — | 0.57% | >15 | >1.6 |
| CBH2b | — | 0.30% | 0.18% | — | 0.48% | >35 | >1.3 |
| EG2 | — | — | 0.18% | 0.20% | 0.38% | >25 | >1.2 |
| CBH1a + CBH2b | 0.39% | 0.30% | 0.18% | — | 0.87% | >75 | >1.7 |
| CBH2b + EG2 | — | 0.30% | 0.18% | 0.20% | 0.68% | >40 | >1.1 |
| CBH1a + CBH2b + EG2 | 0.39% | 0.30% | 0.18% | 0.20% | 1.07% | >75 | >1.4 |
| | 0.68% | — | 0.37% | 0.20% | 1.25% | >75 | >1.7 |
| | 1.35% | 1.20% | 0.37% | 0.20% | 3.12% | >125 | >1.6 |
| | 1.35% | 1.20% | 0.74% | 0.20% | 3.49% | >125 | >1.5 |

SEQUENCES

| Exemplary Cellulase Sequences |
|---|

```
C1 BGL1 precursor: SEQ ID NO: 60
MKAAALSCLFGSTLAVAGAIESRKVHQKPLARSEPFYPSPWMNPNADGWAEAYAQAKSFVSQMTLLEKVNLTTGVGWGAEQ
CVGQVGAIPRLGLRSLCMHDSPLGIRGADYNSAFPSGQTVAATWDRGLMYRRGYAMGQEAKGKGINVLLGPVAGPLGRMPE
GGRNWEGFAPDPVLTGIGMSETIKGIQDAGVIACAKHFIGNEQEHFRQVPEAQGYGYNISETLSSNIDDKTMHELYLWPFA
DAVRAGVGSVMCSYQQVNNSYACQNSKLLNDLLKNELGFQGFVMSDWQAQHTGAASAVAGLDMSMPGDTQFNTGVSFWGAN
LTLAVLNGTVPAYRLDDMAMRIMAALFKVTKTTDLEPINFSFWTDDTYGPIHWAAKQGYQEINSHVDVRADHGNLIREIAA
KGTVLLKNTGSLPLNKPKFVAVIGEDAGSSPNGPNGCSDRGCNEGTLAMGWGSGTANYPYLVSPDAALQARAIQDGTRYES
VLSNYAEEKTKALVSQANATAIVFVNADSGEGYINVDGNEGDRKNLTLWNNGDTLVKNVSSWCSNTIVVIHSVGPVLLTDW
YDNPNITAILWAGLPGQESGNSITDVLYGKVNPAARSPFTWGKTRESYGADVLYKPNNGNGAPQQDFTEGVFIDYRYFDKV
DDDSVIYEFGHGLSYTTFEYSNIRVVKSNVSEYRPTTGTTAQAPTFGNFSTDLEDYLFPKDEFPYIYQYIYPYLNTTDPRR
ASADPHYGQTAEEFLPPHATDDDPQPLLRSSGGNSPGGNRQLYDIVYTITADITNTGSVVGEEVPQLYVSLGGPEDPKVQL
RDFDRMRIEPGETRQFTGRLTRRDLSNWDVTVQDWVISRYPKTAYVGRSSRKLDLKIELP TaBGL precursor (Thermoascus aurantiacus): SEQ ID NO: 61
MRLGWLELAVAAAATVASAKDDLAYSPPFYPSPWMDGNGEWAEAYRRAVDFVSQLTLAEKVNLTTGVGWMQEKCVGETGSI
PRLGFRGLCLQDSPLGVRFADYVSAFPAGVNVAATWDKNLAYLRGKAMGEEHRGKGVDVQLGPVAGPLGRHPDGGRNWEGF
SPDPVLTGVLMAETIKGIQDAGVIACAKHFIGNEMEHFRQASEAVGYGFDITESVSSNIDDKTLHELYLWPFADAVRAGVG
SFMCSYNQVNNSYSCSNSYLLNKLLKSELDFQGFVMSDWGAHHSGVGAALAGLDMSMPGDTAFGTGKSFWGTNLTIAVLNG
TVPEWRVDDMAVRIMAAFYKVGRDRYQVPVNFDSWTKDEYGYEHALVGQNYVKVNDKVDVRADHADIIRQIGSASVVLLKN
DGGLPLTGYEKFTGVFGEDAGSNRWGADGCSDRGCDNGTLAMGWGSGTADFPYLVTPEQAIQNEILSKGKGLVSAVTDNGA
LDQMEQVASQASVSIVFVNADSGEGYINVDGNEGDRKNLTLWKGGEEVIKTVAANCNNTIVVMHTVGPVLIDEWYDNPNVT
AIVWAGLPGQESGNSLVDVLYGRVSPGGKTPFTWGKTRESYGAPLLTKPNNGKGAPQDFTEGVFIDYRRFDKYNETPIYE
FGFGLSYTTFEYSDIYVQPLNARPYTPASGSTKAAPTFGNISTDYADYLYPEDIHKVPLYIYPWLNTTDPKKSSGDPDYGM
KAEDYIPSGATDGSPQPILPAGGAPGGNPGLYDEMYRVSAIITNTGNVVGDEVPQLYVSLGGPDDPKVVLRNFDRITLHPG
QQTMWTTTLTRRDISNWDPASQNWVVTKYPKTVYIGSSSRKLHLQAPLPPY CelA BGL precursor (Azospirillum irakense): SEQ ID NO: 62
MGALRLLGSISIVALTCGGIHASTAIAQEGAAPAAILHPEKWPRPATQRLIDPAVEKRVDALLKQLSVEEKVGQVIQGDIG
TITPEDLRKYPLGSILAGGNSGPNGDDRAPPKEWLDLADAFYRVSLEKRPGHTPIPVLFGIDAVHGHGNIGSATIFPHNIA
LGATHDPELLRRIGEVTAVEMAATGIDWTFAPALSVVRDDRWGRTYEGFSEDPEIVAAYSAAIVEGVQGKFGSKDFMAPGR
IVASAKHFLADGGTDQGRDQGDARISEDELIRIHNAGYPPAIDAGVLTVMASFSSWQGIKHHGHKQLLTDVLKGQMGFNGF
IVGDWNAHDQVPGCTKFNCPTSLIAGLDMYMAADSWKQLYENTLAQVKDGTIPMARLDDAVRRILRVKVLAGLFEKPAPKD
RPGLPGLETLGSPEHRAVGREAVRKSLVLLKNDKGTLPLSPKARVLVAGDGADNIGKQSGGWTISWQGTGNRNDEFPGATS
ILGGIRDAVADAGGSVEFDVAGQYKTKPDVAIVVFGEEPYAEFQGDVETLEYQPDQKQDLALLKKLKDQGIPVVAVFLSGR
PMWVNPELNASDAFVAAWLPGTEGGGVADVLFTDKAGKVQHDFAGKLSYSWPRTAAQTTVNRGDADYNPLFAYGYGLTYKD
KSKVGTLPEESGVPAEARQNAGIYFRAGALRLPGRFL C1 CBH1a: SEQ ID NO: 63
QNACTLTAENHPSLTWSKCTSGGSCTSVQGSITIDANWRWTHRTDSATNCYEGNKWDTSYCSDGPSCASKCCIDGADYSST
YGITTSGNSLNLKFVTKGQYSTNIGSRTYLMESDTKYQMFQLLGNEFTFDVDVSNLGCGLNGALYFVSMDADGGMSKYSGN
KAGAKYGTGYCDSQCPRDLKFINGEANVENWQSSTNDANAGTGKYGSCCSEMDVWEANNMAAAFTPHPCTVIGQSRCEGDS
CGGTYSTDRYAGICDPDGCDFNSYRQGNKTFYGKGMTVDTTKKITVVTQFLKNSAGELSEIKRFYVQNGKVIPNSESTIPG
VEGNSITQDWCDRQKAAFGDVTDFQDKGGMVQMGKALAGPMVLVMSIWDDHAVNMLWLDSTWPIDGAGKPGAERGACPTTS
GVPAEVEAEAPNSNVIFSNIRFGPIGSTVSGLPDGGSGNPNPPVSSSTPVPSSSTTSSGSSGPTGGTGVAKHYEQCGGIGF
TGPTQCESPYTCTKLNDWYSQCL C1 CBH2a precursor: SEQ ID NO: 64
MKFVQSATLAFAATALAAPSRTTPQKPRQASAGCASAVTLDASTNVFQQYTLHPNNFYRAEVEAAAEAISDSALAEKARKV
ADVGTFLWLDTIENIGRLEPALEDVPCENIVGLVIYDLPGRDCAAKASNGELKVGELDRYKTEVIDKIAEILKAHSNTAFA
LVIEPDSLPNLVTNSDLQTCQQSASGYREGVAYALKQLNLPNVVMYIDAGHGGWLGWDANLKPGAQELASVYKSAGSPSQV
RGISTNVAGWNAWDQEPGEFSDASDAQYNKCQNEKIYINTFGAELKSAGMPNHAIIDTGRNGVTGLRDEWGDWCNVNGAGF
GVRPTANTGDELADAFVWVKPGGESDGTSDSSAARYDSFCGKPDAFKPSPEAGTWNQAYFEMLLKNANPSF M. thermophila Endoglucanase 2 (EG2): SEQ ID NO: 65
QSGPWQQCGGIGWQGSTDCVSGYHCVYQNDWYSQCVPGAASTTLQTSTTSRPTATSTAPPSSTTSPSKGKLKW
LGSNESGAEFGEGNYPGLWGKHFIFPSTSAIQTLINDGYNIFRIDFSMERLVPNQLTSSFDEGYLRNLTEVVN
FVTNAGKYAVLDPHNYGRYYGNVITDTNAFRTFWTNLAKQFASNSLVIFDTNNEYNTMDQTLVLNLNQAAIDG
IRAAGATSQYIFVEGNAWSGAWSWNTTNTNMAALTDPQNKIVYEMHQYLDSDSSGTHAECVSSNIGAQRVVGA
TQWLRANGKLGVLGEFAGGANAVCQQAVTGLLDHLQDNSDVWLGALWWAAGPWWGDYMYSFEPPSGTGYVNYN
SILKKYLP M. thermophila Beta-glucosidase (BG): SEQ ID NO: 66
IESRKVHQKPLARSEPFYPSPWMNPNADGWAEAYAQAKSFVSQMTLLEKVNLTTGVGWGAEQCVGQVGAIPRL
GLRSLCMHDSPLGIRGADYNSAFPSGQTVAATWDRGLMYRRGYAMGQEAKGKGINVLLGPVAGPLGRMPEGGR
NWEGFAPDPVLTGIGMSETIKGIQDAGVIACAKHFIGNEQEHFRQVPEAQGYGYNISETLSSNIDDKTMHELY
LWPFADAVRAGVGSVMCSYQQVNNSYACQNSKLLNDLLKNELGFQGFVMSDWQAQHTGAASAVAGLDMSMPGD
TQFNTGVSFWGANLTLAVLNGTVPAYRLDDMAMRIMAALFKVTKTTDLEPINFSFWTDDTYGPIHWAAKQGYQ
EINSHVDVRADHGNLIREIAAKGTVLLKNTGSLPLNKPKFVAVIGEDAGSSPNGPNGCSDRGCNEGTLAMGWG
SGTANYPYLVSPDAALQARAIQDGTRYESVLSNYAEEKTKALVSQANATAIVFVNADSGEGYINVDGNEGDRK
NLTLWNNGDTLVKNVSSWCSNTIVVIHSVGPVLLTDWYDNPNITAILWAGLPGQESGNSITDVLYGKVNPAAR
```

-continued

```
SPFTWGKTRESYGADVLYKPNNGNGAPQQDFTEGVFIDYRYFDKVDDDSVIYEFGHGLSYTTFEYSNIRVVKS
NVSEYRPTTGTTAQAPTFGNFSTDLEDYLFPKDEFPYIYQYIYPYLNTTDPRRASADPHYGQTAEEFLPPHAT
DDDPQPLLRSSGGNSPGGNRQLYDIVYTITADITNTGSVVGEEVPQLYVSLGGPEDPKVQLRDFDRMRIEPGE
TRQFTGRLTRRDLSNWDVTVQDWVISRYPKTAYVGRSSRKLDLKIELP

M. thermophila Cellobiohydrolase Type 1a (Cbh1a): SEQ ID NO: 67
QNACTLTAENHPSLTWSKCTSGGSCTSVQGSITIDANWRWTHRTDSATNCYEGNKWDTSYCSDGPSCASKCCI
DGADYSSTYGITTSGNSLNLKFVTKGQYSTNIGSRTYLMESDTKYQMFQLLGNEFTFDVDVSNLGCGLNGALY
FVSMDADGGMSKYSGNKAGAKYGTGYCDSQCPRDLKFINGEANVENWQSSTNDANAGTGKYGSCCSEMDVWEA
NNMAAAFTPHPCTVIGQSRCEGDSCGGTYSTDRYAGICDPDGCDFNSYRQGNKTFYGKGMTVDTTKKITVVTQ
FLKNSAGELSEIKRFYVQNGKVIPNSESTIPGVEGNSITQDWCDRQKAAFGDVTDFQDKGGMVQMGKALAGPM
VLVMSIWDDHAVNMLWLDSTWPIDGAGKPGAERGACPTTSGVPAEVEAEAPNSNVIFSNIRFGPIGSTVSGLP
DGGSGNPNPPVSSSTPVPSSSTTSSGSSGPTGGTGVAKHYEQCGGIGFTGPTQCESPYTCTKLNDWYSQCL M. thermophila Cellobiohydrolase Type 2b (CBH2b): SEQ ID NO: 68
APVIEERQNCGAVWTQCGGNGWQGPTCCASGSTCVAQNEWYSQCLPNSQVTSSTTPSSTSTSQRSTSTSSSTT
RSGSSSSSSTTPPPVSSPVTSIPGGATSTASYSGNPFSGVRLFANDYYRSEVHNLAIPSMTGTLAAKASAVAE
VPSFQWLDRNVTIDTLMVQTLSQVRALNKAGANPPYAAQLVVYDLPDRDCAAAASNGEFSIANGGAANYRSYI
DAIRKHIIEYSDIRIILVIEPDSMANMVTNMNVAKCSNAASTYHELTVYALKQLNLPNVAMYLDAGHAGWLGW
PANIQPAAELFAGIYNDAGKPAAVRGLATNVANYNAWSIASAPSYTSPNPNYDEKHYIEAFSPLLNSAGFPAR
FIVDTGRNGKQPTGQQQWGDWCNVKGTGFGVRPTANTGHELVDAFVWVKPGGESDGTSDTSAARYDYHCGLSD
ALQPAPEAGQWFQAYFEQLLTNANPPF
```

| GH61a Encoding Sequence |
|---|

```
SEQ ID NO: 31
atgtccaagg cctctgctct cctcgctggc ctgacgggcg cggccctcgt cgctgcacat    60
ggccacgtca gccacatcgt cgtcaacggc gtctactaca ggaactacga ccccacgaca   120
gactggtacc agcccaaccc gccaacagtc atcggctgga cggcagccga tcaggataat   180
ggcttcgttg aacccaacag ctttggcacg ccagatatca tctgccacaa gagcgccacc   240
cccggcggcg gccacgctac cgttgctgcc ggagacaaga tcaacatcgt ctggacccccc  300
gagtggcccg aatcccacat cggcccccgtc attgactacc tagccgcctg caacggtgac   360
tgcgagaccg tcgacaagtc gtcgctgcgc tggttcaaga ttgacggcgc cggctacgac   420
aaggccgccg gccgctgggc cgccgacgct ctgcgcgcca acgcaaacag ctggctcgtc   480
cagatcccgt cggatctcaa ggccggcaac tacgtcctcc gccacgagat catcgccctc   540
cacggtgctc agagcccccaa cggcgcccag gcctacccgc agtgcatcaa cctccgcgtc   600
accggcggcg gcagcaacct gcccagcggc gtcgccggca cctcgctgta caaggcgacc   660
gacccgggca tcctcttcaa cccctacgtc tcctccccgg attacaccgt ccccggcccg   720
gccctcattg ccggcgccgc cagctcgatc gcccagaagca cgtcggtcgc cactgccacc   780
ggcacggcca ccgttcccgg cggcggcggc gccaaccctca ccgccaccac caccgccgcc   840
acctccgccg ccccgagcac caccctgagg acgaccacta cctcggccgc gcagactacc   900
gccccgcct ccggcgatgt gcagaccaag tacgccagt gtggtggcaa cggatggacg   960
ggcccgacgg tgtgcgcccc cggctcgagc tgctccgtcc tcaacgagtg gtactcccag   1020
tgtttgtaa                                                            1029
```

SEQ ID NOs: 32 to 59 appear in the formal Sequence Listing for this disclosure.

Use of GH61 proteins of this invention is not intended to be limited in any way by theory as to their mode of action. Theoretically, the yield of product may be increased by action of the GH61 protein on the substrate, by interaction of the GH61 protein directly with any one or more of the cellulase enzyme(s) in a mixture, by lowering viscosity of the reaction mixture, or by any other mechanism. This invention may be practiced by following GH61 activity in an empirical fashion using assay methods described in this disclosure, without knowing the mechanism of operation of the GH61 protein being used.

While the invention has been described with reference to the specific embodiments, various changes can be made and equivalents can be substituted to adapt to a particular situation, material, composition of matter, process, process step or steps, thereby achieving benefits of the invention without departing from the scope of what is claimed.

For all purposes in the United States of America, each and every publication and patent document cited in this disclosure is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

The invention claimed is:

1. A method for increasing yield of fermentable sugars in a reaction, said method comprising:
contacting a cellulose containing substrate with:
  (i) a plurality of cellulase enzymes comprising one or more β-glucosidases (BGL) and one or more cellobiohydrolases (CBH), and
  (ii) a purified variant glycosidase hydrolase 61 (GH61) protein comprising an amino acid sequence that is at least 90% identical but not 100% identical to the amino acid residues corresponding to amino acid residues 11-323 of the amino acid sequence of SEQ ID NO: 2 and having glycosidase hydrolase (GH61) activity,
thereby increasing said yield of fermentable sugars.

2. A method of producing a biofuel containing ethanol, said method comprising:
(a) contacting a cellulose containing substrate with:
  (i) a plurality of cellulase enzymes comprising endoglucanase (EG), a β-glucosidase (BGL), a cellobiohydrolase (CBH); and
  (ii) a purified variant glycosidase hydrolase 61 (GH61) protein comprising an amino acid sequence that is at least 90% identical but not 100% identical to the amino acid residues corresponding to amino acid residues 11-323 of the amino acid sequence of SEQ ID NO: 2 and having glycosidase hydrolase (GH61) activity,
under conditions where simple sugars are produced from said cellulose containing substrate;
(b) combining said simple sugars produced in step (a) with fungal cells under fermentation conditions to produce ethanol.

3. The method of claim 2, wherein said fungal cells are yeast cells.

4. The method of claim 2, wherein said purified variant GH61 protein comprises an amino acid sequence that is at least 95% identical to the amino acid residues corresponding to amino acid residues 11-323 of the amino acid sequence of SEQ ID NO: 2.

5. The method of claim 2, wherein said purified variant GH61 protein comprises an amino acid sequence that is at least 98% identical to the amino acid residues corresponding to amino acid residues 11-323 of the amino acid sequence of SEQ ID NO: 2.

6. The method of claim 1, wherein said purified variant GH61 protein comprises an amino acid sequence that is at least 95% identical to the amino acid residues corresponding to amino acid residues 11-323 of the amino acid sequence of SEQ ID NO: 2.

7. The method of claim 1, wherein said cellulase enzymes are from *Myceliophthora thermophila*.

8. The method of claim 1, wherein said cellulase enzymes are each selected from the amino acid sequence of SEQ ID NOs: 61 to 68.

9. The method of claim 1, wherein said cellulose containing substrate is selected from the group consisting of wheat, wheat straw, sorghum, corn, rice, barley, sugar cane bagasse, grasses, switchgrass, corn grain, corn cobs, corn fiber, and a combination thereof.

10. The method of claim 1, wherein said cellulose containing substrate is wheat straw.

11. The method of claim 1, wherein said purified variant GH61 protein comprises an amino acid sequence that is at least 98% identical to the amino acid residues corresponding to amino acid residues 11-323 of the amino acid sequence of SEQ ID NO: 2.

12. The method of claim 2, wherein said cellulase enzymes are from *Myceliophthora thermophila*.

13. The method of claim 2, wherein said cellulase enzymes are each selected from the amino acid sequence of SEQ ID NOs: 61 to 68.

14. The method of claim 2, wherein said cellulose containing substrate is selected from the group consisting of wheat, wheat straw, sorghum, corn, rice, barley, sugar cane bagasse, grasses, switchgrass, corn grain, corn cobs, corn fiber, and a combination thereof.

15. The method of claim 2, wherein said cellulose containing substrate is wheat straw.

16. The method of claim 1, wherein said plurality of cellulase enzymes further comprises an endoglucanase (EG).

17. The method of claim 1, wherein said plurality of cellulase enzymes is free of added endoglucanase (EG).

18. A method for increasing yield of fermentable sugars, said method comprising:
contacting a cellulose containing substrate with:
  (i) a plurality of cellulase enzymes comprising one or more β-glucosidases (BGL) and one or more cellobiohydrolases (CBH), and (ii) a purified variant glycosidase hydrolase 61 (GH61) protein, wherein said GH61 protein consists of an amino acid sequence that is at least 90% identical to a fragment corresponding to amino acid residues 11-323 of the amino acid sequence of SEQ ID NO: 2 and having glycosidase 61 (GH61) activity, thereby increasing said yield of fermentable sugars.

19. The method of claim 18, wherein said purified variant GH61 protein consists of an amino acid sequence that is at least 95% identical to a fragment corresponding to amino acid residues 11-323 of the amino acid sequence of SEQ ID NO: 2.

20. The method of claim 18, wherein said purified variant GH61 protein consists of an amino acid sequence that is at least 98% identical to a fragment corresponding to amino acid residues 11-323 of the amino acid sequence of SEQ ID NO: 2.

21. The method of claim 18, wherein said cellulase enzymes are from *Myceliophthora thermophila*.

22. The method of claim 18, wherein said cellulase enzymes are each selected from the amino acid sequence of SEQ ID NOs: 61 to 68.

23. The method of claim 18, wherein said cellulose containing substrate is selected from the group consisting of wheat, wheat straw, sorghum, corn, rice, barley, sugar cane bagasse, grasses, switchgrass, corn grain, corn cobs, corn fiber, and a combination thereof.

24. The method of claim 18, wherein said cellulose containing substrate is wheat straw.

* * * * *

SEQUENCE LISTING

```
<160> NUMBER OF SEQ ID NOS: 70

<210> SEQ ID NO 1
<211> LENGTH: 342
<212> TYPE: PRT
<213> ORGANISM: Myceliophthora thermophila

<400> SEQUENCE: 1

Met Ser Lys Ala Ser Ala Leu Leu Ala Gly Leu Thr Gly Ala Ala Leu
```

```
            1               5                  10                 15
    Val Ala Ala His Gly His Val Ser His Ile Val Val Asn Gly Val Tyr
                    20                  25                  30
    Tyr Arg Asn Tyr Asp Pro Thr Thr Asp Trp Tyr Gln Pro Asn Pro Pro
                    35                  40                  45
    Thr Val Ile Gly Trp Thr Ala Ala Asp Gln Asp Asn Gly Phe Val Glu
    50                      55                  60
    Pro Asn Ser Phe Gly Thr Pro Asp Ile Ile Cys His Lys Ser Ala Thr
    65                  70                  75                  80
    Pro Gly Gly Gly His Ala Thr Val Ala Ala Gly Asp Lys Ile Asn Ile
                        85                  90                  95
    Val Trp Thr Pro Glu Trp Pro Glu Ser His Ile Gly Pro Val Ile Asp
                    100                 105                 110
    Tyr Leu Ala Ala Cys Asn Gly Asp Cys Glu Thr Val Asp Lys Ser Ser
                    115                 120                 125
    Leu Arg Trp Phe Lys Ile Asp Gly Ala Gly Tyr Asp Lys Ala Ala Gly
    130                     135                 140
    Arg Trp Ala Ala Asp Ala Leu Arg Ala Asn Gly Asn Ser Trp Leu Val
    145                 150                 155                 160
    Gln Ile Pro Ser Asp Leu Lys Ala Gly Asn Tyr Val Leu Arg His Glu
                    165                 170                 175
    Ile Ile Ala Leu His Gly Ala Gln Ser Pro Asn Gly Ala Gln Ala Tyr
                    180                 185                 190
    Pro Gln Cys Ile Asn Leu Arg Val Thr Gly Gly Gly Ser Asn Leu Pro
                    195                 200                 205
    Ser Gly Val Ala Gly Thr Ser Leu Tyr Lys Ala Thr Asp Pro Gly Ile
    210                     215                 220
    Leu Phe Asn Pro Tyr Val Ser Ser Pro Asp Tyr Thr Val Pro Gly Pro
    225                 230                 235                 240
    Ala Leu Ile Ala Gly Ala Ala Ser Ser Ile Ala Gln Ser Thr Ser Val
                    245                 250                 255
    Ala Thr Ala Thr Gly Thr Ala Thr Val Pro Gly Gly Gly Gly Ala Asn
                    260                 265                 270
    Pro Thr Ala Thr Thr Thr Ala Ala Thr Ser Ala Ala Pro Ser Thr Thr
                    275                 280                 285
    Leu Arg Thr Thr Thr Thr Ser Ala Ala Gln Thr Thr Ala Pro Pro Ser
                    290                 295                 300
    Gly Asp Val Gln Thr Lys Tyr Gly Gln Cys Gly Gly Asn Gly Trp Thr
    305                 310                 315                 320
    Gly Pro Thr Val Cys Ala Pro Gly Ser Ser Cys Ser Val Leu Asn Glu
                        325                 330                 335
    Trp Tyr Ser Gln Cys Leu
                340

<210> SEQ ID NO 2
<211> LENGTH: 323
<212> TYPE: PRT
<213> ORGANISM: Myceliophthora thermophila

<400> SEQUENCE: 2

His Gly His Val Ser His Ile Val Val Asn Gly Val Tyr Tyr Arg Asn
1               5                   10                  15
Tyr Asp Pro Thr Thr Asp Trp Tyr Gln Pro Asn Pro Thr Val Ile
            20                  25                  30
```

```
Gly Trp Thr Ala Ala Asp Gln Asp Asn Gly Phe Val Glu Pro Asn Ser
            35                  40                  45

Phe Gly Thr Pro Asp Ile Ile Cys His Lys Ser Ala Thr Pro Gly Gly
 50                  55                  60

Gly His Ala Thr Val Ala Ala Gly Asp Lys Ile Asn Ile Val Trp Thr
 65                  70                  75                  80

Pro Glu Trp Pro Glu Ser His Ile Gly Pro Val Ile Asp Tyr Leu Ala
                    85                  90                  95

Ala Cys Asn Gly Asp Cys Glu Thr Val Asp Lys Ser Ser Leu Arg Trp
                100                 105                 110

Phe Lys Ile Asp Gly Ala Gly Tyr Asp Lys Ala Ala Gly Arg Trp Ala
            115                 120                 125

Ala Asp Ala Leu Arg Ala Asn Gly Asn Ser Trp Leu Val Gln Ile Pro
130                 135                 140

Ser Asp Leu Lys Ala Gly Asn Tyr Val Leu Arg His Glu Ile Ile Ala
145                 150                 155                 160

Leu His Gly Ala Gln Ser Pro Asn Gly Ala Gln Ala Tyr Pro Gln Cys
                165                 170                 175

Ile Asn Leu Arg Val Thr Gly Gly Ser Asn Leu Pro Ser Gly Val
            180                 185                 190

Ala Gly Thr Ser Leu Tyr Lys Ala Thr Asp Pro Gly Ile Leu Phe Asn
            195                 200                 205

Pro Tyr Val Ser Ser Pro Asp Tyr Thr Val Pro Gly Pro Ala Leu Ile
            210                 215                 220

Ala Gly Ala Ala Ser Ser Ile Ala Gln Ser Thr Ser Val Ala Thr Ala
225                 230                 235                 240

Thr Gly Thr Ala Thr Val Pro Gly Gly Gly Ala Asn Pro Thr Ala
                245                 250                 255

Thr Thr Thr Ala Ala Thr Ser Ala Ala Pro Ser Thr Thr Leu Arg Thr
            260                 265                 270

Thr Thr Thr Ser Ala Ala Gln Thr Thr Ala Pro Pro Ser Gly Asp Val
            275                 280                 285

Gln Thr Lys Tyr Gly Gln Cys Gly Gly Asn Gly Trp Thr Gly Pro Thr
            290                 295                 300

Val Cys Ala Pro Gly Ser Ser Cys Ser Val Leu Asn Glu Trp Tyr Ser
305                 310                 315                 320

Gln Cys Leu

<210> SEQ ID NO 3
<211> LENGTH: 278
<212> TYPE: PRT
<213> ORGANISM: Myceliophthora thermophila

<400> SEQUENCE: 3

Met Phe Ser Leu Lys Phe Phe Ile Leu Ala Gly Gly Leu Ala Val Leu
 1               5                  10                  15

Thr Glu Ala His Ile Arg Leu Val Ser Pro Ala Pro Phe Thr Asn Pro
                20                  25                  30

Asp Gln Gly Pro Ser Pro Leu Leu Glu Ala Gly Ser Asp Tyr Pro Cys
            35                  40                  45

His Asn Gly Asn Gly Gly Tyr Gln Gly Thr Pro Thr Gln Met Ala
 50                  55                  60

Lys Gly Ser Lys Gln Gln Leu Ala Phe Gln Gly Ser Ala Val His Gly
 65                  70                  75                  80
```

```
Gly Gly Ser Cys Gln Val Ser Ile Thr Tyr Asp Glu Asn Pro Thr Ala
                85                  90                  95

Gln Ser Ser Phe Lys Val Ile His Ser Ile Gln Gly Cys Pro Ala
            100                 105                 110

Arg Ala Glu Thr Ile Pro Asp Cys Ser Ala Gln Asn Ile Asn Ala Cys
            115                 120                 125

Asn Ile Lys Pro Asp Asn Ala Gln Met Asp Thr Pro Asp Lys Tyr Glu
130                 135                 140

Phe Thr Ile Pro Glu Asp Leu Pro Ser Gly Lys Ala Thr Leu Ala Trp
145                 150                 155                 160

Thr Trp Ile Asn Thr Ile Gly Asn Arg Glu Phe Tyr Met Ala Cys Ala
                165                 170                 175

Pro Val Glu Ile Thr Gly Asp Gly Ser Glu Ser Ala Leu Ala Ala
            180                 185                 190

Leu Pro Asp Met Val Ile Ala Asn Ile Pro Ser Ile Gly Gly Thr Cys
            195                 200                 205

Ala Thr Glu Glu Gly Lys Tyr Tyr Glu Tyr Pro Asn Pro Gly Lys Ser
            210                 215                 220

Val Glu Thr Ile Pro Gly Trp Thr Asp Leu Val Pro Leu Gln Gly Glu
225                 230                 235                 240

Cys Gly Ala Ala Ser Gly Val Ser Gly Ser Gly Asn Ala Ser Ser
                245                 250                 255

Ala Thr Pro Ala Ala Gly Ala Ala Pro Thr Pro Ala Val Arg Gly Arg
            260                 265                 270

Arg Pro Thr Trp Asn Ala
            275

<210> SEQ ID NO 4
<211> LENGTH: 223
<212> TYPE: PRT
<213> ORGANISM: Myceliophthora thermophila

<400> SEQUENCE: 4

Met Lys Leu Ala Thr Leu Leu Ala Ala Leu Thr Leu Gly Val Ala Asp
1               5                   10                  15

Gln Leu Ser Val Gly Ser Arg Lys Phe Gly Val Tyr Glu His Ile Arg
            20                  25                  30

Lys Asn Thr Asn Tyr Asn Ser Pro Val Thr Asp Leu Ser Asp Thr Asn
        35                  40                  45

Leu Arg Cys Asn Val Gly Gly Gly Ser Gly Thr Ser Thr Thr Val Leu
    50                  55                  60

Asp Val Lys Ala Gly Asp Ser Phe Thr Phe Phe Ser Asp Val Ala Val
65                  70                  75                  80

Tyr His Gln Gly Pro Ile Ser Leu Cys Val Asp Arg Thr Ser Ala Glu
                85                  90                  95

Ser Met Asp Gly Arg Glu Pro Asp Met Arg Cys Arg Thr Gly Ser Gln
            100                 105                 110

Ala Gly Tyr Leu Ala Val Thr Asp Tyr Asp Gly Ser Gly Asp Cys Phe
            115                 120                 125

Lys Ile Tyr Asp Trp Gly Pro Thr Phe Asn Gly Gln Ala Ser Trp
130                 135                 140

Pro Thr Arg Asn Ser Tyr Glu Tyr Ser Ile Leu Lys Cys Ile Arg Asp
145                 150                 155                 160

Gly Glu Tyr Leu Leu Arg Ile Gln Ser Leu Ala Ile His Asn Pro Gly
                165                 170                 175
```

-continued

```
Ala Leu Pro Gln Phe Tyr Ile Ser Cys Ala Gln Val Asn Val Thr Gly
            180                 185                 190

Gly Gly Thr Val Thr Pro Arg Ser Arg Arg Pro Ile Leu Ile Tyr Phe
        195                 200                 205

Asn Phe His Ser Tyr Ile Val Pro Gly Pro Ala Val Phe Lys Cys
    210                 215                 220

<210> SEQ ID NO 5
<211> LENGTH: 192
<212> TYPE: PRT
<213> ORGANISM: Myceliophthora thermophila

<400> SEQUENCE: 5

Met Thr Lys Asn Ala Gln Ser Lys Gln Gly Val Glu Asn Pro Thr Ser
1               5                   10                  15

Gly Asp Ile Arg Cys Tyr Thr Ser Gln Thr Ala Ala Asn Val Val Thr
            20                  25                  30

Val Pro Ala Gly Ser Thr Ile His Tyr Ile Ser Thr Gln Gln Ile Asn
        35                  40                  45

His Pro Gly Pro Thr Gln Tyr Tyr Leu Ala Lys Val Pro Pro Gly Ser
    50                  55                  60

Ser Ala Lys Thr Phe Asp Gly Ser Gly Ala Val Trp Phe Lys Ile Ser
65                  70                  75                  80

Thr Thr Met Pro Thr Val Asp Ser Asn Lys Gln Met Phe Trp Pro Gly
                85                  90                  95

Gln Asn Thr Tyr Glu Thr Ser Asn Thr Thr Ile Pro Ala Asn Thr Pro
            100                 105                 110

Asp Gly Glu Tyr Leu Leu Arg Val Lys Gln Ile Ala Leu His Met Ala
        115                 120                 125

Ser Gln Pro Asn Lys Val Gln Phe Tyr Leu Ala Cys Thr Gln Ile Lys
    130                 135                 140

Ile Thr Gly Gly Arg Asn Gly Thr Pro Ser Pro Leu Val Ala Leu Pro
145                 150                 155                 160

Gly Ala Tyr Lys Ser Thr Asp Pro Gly Ile Leu Val Asp Ile Tyr Ser
                165                 170                 175

Met Lys Pro Glu Ser Tyr Gln Pro Pro Gly Pro Pro Val Trp Arg Gly
            180                 185                 190

<210> SEQ ID NO 6
<211> LENGTH: 283
<212> TYPE: PRT
<213> ORGANISM: Myceliophthora thermophila

<400> SEQUENCE: 6

Met Lys Pro Phe Ser Leu Val Ala Leu Ala Thr Ala Val Ser Gly His
1               5                   10                  15

Ala Ile Phe Gln Arg Val Ser Val Asn Gly Gln Asp Gln Gly Gln Leu
            20                  25                  30

Lys Gly Val Arg Ala Pro Ser Ser Asn Ser Pro Ile Gln Asn Val Asn
        35                  40                  45

Asp Ala Asn Met Ala Cys Asn Ala Asn Ile Val Tyr His Asp Asn Thr
    50                  55                  60

Ile Ile Lys Val Pro Ala Gly Ala Arg Val Gly Ala Trp Trp Gln His
65                  70                  75                  80

Val Ile Gly Gly Pro Gln Gly Ala Asn Asp Pro Asp Asn Pro Ile Ala
                85                  90                  95
```

```
Ala Ser His Lys Gly Pro Ile Gln Val Tyr Leu Ala Lys Val Asp Asn
            100                 105                 110

Ala Ala Thr Ala Ser Pro Ser Gly Leu Lys Trp Phe Lys Val Ala Glu
        115                 120                 125

Arg Gly Leu Asn Asn Gly Val Trp Ala Tyr Leu Met Arg Val Glu Leu
    130                 135                 140

Leu Ala Leu His Ser Ala Ser Ser Pro Gly Gly Ala Gln Phe Tyr Met
145                 150                 155                 160

Gly Cys Ala Gln Ile Glu Val Thr Gly Ser Gly Thr Asn Ser Gly Ser
                165                 170                 175

Asp Phe Val Ser Phe Pro Gly Ala Tyr Ser Ala Asn Asp Pro Gly Ile
            180                 185                 190

Leu Leu Ser Ile Tyr Asp Ser Ser Gly Lys Pro Asn Asn Gly Gly Arg
        195                 200                 205

Ser Tyr Pro Ile Pro Gly Pro Arg Pro Ile Ser Cys Ser Gly Ser Gly
    210                 215                 220

Gly Gly Gly Asn Asn Gly Gly Asp Gly Gly Asp Asp Asn Asn Gly Gly
225                 230                 235                 240

Gly Asn Asn Asn Gly Gly Ser Val Pro Leu Tyr Gly Gln Cys Gly
                245                 250                 255

Gly Ile Gly Tyr Thr Gly Pro Thr Thr Cys Ala Gln Gly Thr Cys Lys
            260                 265                 270

Val Ser Asn Glu Tyr Tyr Ser Gln Cys Leu Pro
        275                 280

<210> SEQ ID NO 7
<211> LENGTH: 212
<212> TYPE: PRT
<213> ORGANISM: Myceliophthora thermophila

<400> SEQUENCE: 7

Met Lys Leu Thr Ser Ser Leu Ala Val Leu Ala Ala Ala Gly Ala Gln
1               5                   10                  15

Ala His Tyr Thr Phe Pro Arg Ala Gly Thr Gly Gly Ser Leu Ser Gly
            20                  25                  30

Glu Trp Glu Val Val Arg Met Thr Glu Asn His Tyr Ser His Gly Pro
        35                  40                  45

Val Thr Asp Val Thr Ser Pro Glu Met Thr Cys Tyr Gln Ser Gly Val
    50                  55                  60

Gln Gly Ala Pro Gln Thr Val Gln Val Lys Ala Gly Ser Gln Phe Thr
65                  70                  75                  80

Phe Ser Val Asp Pro Ser Ile Gly His Pro Gly Pro Leu Gln Phe Tyr
                85                  90                  95

Met Ala Lys Val Pro Ser Gly Gln Thr Ala Ala Thr Phe Asp Gly Thr
            100                 105                 110

Gly Ala Val Trp Phe Lys Ile Tyr Gln Asp Gly Pro Asn Gly Leu Gly
        115                 120                 125

Thr Asp Ser Ile Thr Trp Pro Ser Ala Gly Lys Thr Glu Val Ser Val
    130                 135                 140

Thr Ile Pro Ser Cys Ile Glu Asp Gly Glu Tyr Leu Leu Arg Val Glu
145                 150                 155                 160

His Thr Pro Leu Pro Thr Ala Pro Ala Gln Asn Arg Ala Arg Ser
                165                 170                 175

Ser Pro Ser Pro Ala Ala Tyr Lys Ala Thr Asp Pro Gly Ile Leu Phe
```

```
                    180                 185                 190
Gln Leu Tyr Trp Pro Ile Pro Thr Glu Tyr Ile Asn Pro Gly Pro Ala
            195                 200                 205

Pro Val Ser Cys
        210

<210> SEQ ID NO 8
<211> LENGTH: 149
<212> TYPE: PRT
<213> ORGANISM: Myceliophthora thermophila

<400> SEQUENCE: 8

Met Pro Pro Arg Leu Ser Thr Leu Leu Pro Leu Leu Ala Leu Ile
1               5                   10                  15

Ala Pro Thr Ala Leu Gly His Ser His Leu Gly Tyr Ile Ile Asn
            20                  25                  30

Gly Glu Val Tyr Gln Gly Phe Asp Pro Arg Pro Glu Gln Ala Asn Ser
            35                  40                  45

Pro Leu Arg Val Gly Trp Ser Thr Gly Ala Ile Asp Asp Gly Phe Val
    50                  55                  60

Ala Pro Ala Asn Tyr Ser Ser Pro Asp Ile Ile Cys His Ile Glu Gly
65                  70                  75                  80

Ala Ser Pro Pro Ala His Ala Pro Val Arg Ala Gly Asp Arg Val His
                85                  90                  95

Val Gln Trp Asn Gly Trp Pro Leu Gly His Val Gly Pro Val Leu Ser
            100                 105                 110

Tyr Leu Ala Pro Cys Gly Gly Leu Glu Gly Ser Glu Ser Gly Cys Ala
            115                 120                 125

Gly Val Asp Lys Arg Gln Leu Arg Trp Thr Lys Val Asp Asp Ser Leu
    130                 135                 140

Pro Ala Met Glu Leu
145

<210> SEQ ID NO 9
<211> LENGTH: 151
<212> TYPE: PRT
<213> ORGANISM: Myceliophthora thermophila

<400> SEQUENCE: 9

Met Arg Ser Thr Leu Ala Gly Ala Leu Ala Ala Ile Ala Ala Gln Lys
1               5                   10                  15

Val Ala Gly His Ala Thr Phe Gln Gln Leu Trp His Gly Ser Ser Cys
            20                  25                  30

Val Arg Leu Pro Ala Ser Asn Ser Pro Val Thr Asn Val Gly Ser Arg
            35                  40                  45

Asp Phe Val Cys Asn Ala Gly Thr Arg Pro Val Ser Gly Lys Cys Pro
    50                  55                  60

Val Lys Ala Gly Gly Thr Val Thr Ile Glu Met His Gln Gln Pro Gly
65                  70                  75                  80

Asp Arg Ser Cys Asn Asn Glu Ala Ile Gly Gly Ala His Trp Gly Pro
                85                  90                  95

Val Gln Val Tyr Leu Thr Lys Val Gln Asp Ala Ala Thr Ala Asp Gly
            100                 105                 110

Ser Thr Gly Trp Phe Lys Ile Phe Ser Asp Ser Trp Ser Lys Lys Pro
            115                 120                 125

Gly Gly Asn Leu Gly Asp Asp Asp Asn Trp Gly Thr Arg Asp Leu Asn
```

```
                130                 135                 140
Ala Cys Cys Gly Lys Met Asp
145                 150

<210> SEQ ID NO 10
<211> LENGTH: 245
<212> TYPE: PRT
<213> ORGANISM: Myceliophthora thermophila

<400> SEQUENCE: 10

Met Leu Leu Leu Thr Leu Ala Thr Leu Val Thr Leu Ala Arg His
1               5                   10                  15

Val Ser Ala His Ala Arg Leu Phe Arg Val Ser Val Asp Gly Lys Asp
                20                  25                  30

Gln Gly Asp Gly Leu Asn Lys Tyr Ile Arg Ser Pro Ala Thr Asn Asp
            35                  40                  45

Pro Val Arg Asp Leu Ser Ser Ala Ala Ile Val Cys Asn Thr Gln Gly
    50                  55                  60

Ser Lys Ala Ala Pro Asp Phe Val Arg Ala Ala Gly Asp Lys Leu
65                  70                  75                  80

Thr Phe Leu Trp Ala His Asp Asn Pro Asp Pro Val Asp Tyr Val
                85                  90                  95

Leu Asp Pro Ser His Lys Gly Ala Ile Leu Thr Tyr Val Ala Ala Tyr
            100                 105                 110

Pro Ser Gly Asp Pro Thr Gly Pro Ile Trp Ser Lys Leu Ala Glu Glu
        115                 120                 125

Gly Phe Thr Gly Gly Gln Trp Ala Thr Ile Lys Met Ile Asp Asn Gly
        130                 135                 140

Gly Lys Val Asp Val Thr Leu Pro Glu Ala Leu Ala Pro Gly Lys Tyr
145                 150                 155                 160

Leu Ile Arg Gln Glu Leu Leu Ala Leu His Arg Ala Asp Phe Ala Cys
                165                 170                 175

Asp Asp Pro Ala His Pro Asn Arg Gly Ala Glu Ser Tyr Pro Asn Cys
            180                 185                 190

Val Gln Val Glu Val Ser Gly Ser Gly Asp Lys Lys Pro Asp Gln Asn
        195                 200                 205

Phe Asp Phe Asn Lys Gly Tyr Thr Cys Asp Asn Lys Gly Leu His Phe
    210                 215                 220

Lys Ile Tyr Ile Gly Gln Asp Ser Gln Tyr Val Ala Pro Gly Pro Arg
225                 230                 235                 240

Pro Trp Asn Gly Ser
            245

<210> SEQ ID NO 11
<211> LENGTH: 199
<212> TYPE: PRT
<213> ORGANISM: Myceliophthora thermophila

<400> SEQUENCE: 11

Met Phe Thr Ser Leu Cys Ile Thr Asp His Trp Arg Thr Leu Ser Ser
1               5                   10                  15

His Ser Gly Pro Val Met Asn Tyr Leu Ala His Cys Thr Asn Asp Asp
                20                  25                  30

Cys Lys Ser Phe Lys Gly Asp Ser Gly Asn Val Trp Val Lys Ile Glu
            35                  40                  45

Gln Leu Ala Tyr Asn Pro Ser Ala Asn Pro Pro Trp Ala Ser Asp Leu
```

```
                          50                  55                  60
Leu Arg Glu His Gly Ala Lys Trp Lys Val Thr Ile Pro Pro Ser Leu
 65                  70                  75                  80

Val Pro Gly Glu Tyr Leu Leu Arg His Glu Ile Leu Gly Leu His Val
                     85                  90                  95

Ala Gly Thr Val Met Gly Ala Gln Phe Tyr Pro Gly Cys Thr Gln Ile
                    100                 105                 110

Arg Val Thr Glu Gly Gly Ser Thr Gln Leu Pro Ser Gly Ile Ala Leu
                    115                 120                 125

Pro Gly Ala Tyr Gly Pro Gln Asp Glu Gly Ile Leu Val Asp Leu Trp
                130                 135                 140

Arg Val Asn Gln Gly Gln Val Asn Tyr Thr Ala Pro Gly Gly Pro Val
145                 150                 155                 160

Trp Ser Glu Ala Trp Asp Thr Glu Phe Gly Gly Ser Asn Thr Thr Glu
                    165                 170                 175

Cys Ala Thr Met Leu Asp Asp Leu Leu Asp Tyr Met Ala Ala Asn Asp
                    180                 185                 190

Glu Trp Ile Gly Trp Thr Ala
                    195

<210> SEQ ID NO 12
<211> LENGTH: 227
<212> TYPE: PRT
<213> ORGANISM: Myceliophthora thermophila

<400> SEQUENCE: 12

Met Lys Leu Ser Ala Ala Ile Ala Val Leu Ala Ala Leu Ala Glu
 1               5                  10                  15

Gly His Tyr Thr Phe Pro Ser Ile Ala Asn Thr Ala Asp Trp Gln Tyr
                     20                  25                  30

Val Arg Ile Thr Thr Asn Phe Gln Ser Asn Gly Pro Val Thr Asp Val
                 35                  40                  45

Asn Ser Asp Gln Ile Arg Cys Tyr Glu Arg Asn Pro Gly Thr Gly Ala
 50                  55                  60

Pro Gly Ile Tyr Asn Val Thr Ala Gly Thr Thr Ile Asn Tyr Asn Ala
 65                  70                  75                  80

Lys Ser Ser Ile Ser His Pro Gly Pro Met Ala Phe Tyr Ile Ala Lys
                     85                  90                  95

Val Pro Ala Gly Gln Ser Ala Ala Thr Trp Asp Gly Lys Gly Ala Val
                    100                 105                 110

Trp Ser Lys Ile His Gln Glu Met Pro His Phe Gly Thr Ser Leu Thr
                    115                 120                 125

Trp Asp Ser Asn Gly Arg Thr Ser Met Pro Val Thr Ile Pro Arg Cys
                130                 135                 140

Leu Gln Asp Gly Glu Tyr Leu Leu Arg Ala Glu His Ile Ala Leu His
145                 150                 155                 160

Ser Ala Gly Ser Pro Gly Gly Ala Gln Phe Tyr Ile Ser Cys Ala Gln
                    165                 170                 175

Leu Ser Val Thr Gly Gly Ser Gly Thr Trp Asn Pro Arg Asn Lys Val
                    180                 185                 190

Ser Phe Pro Gly Ala Tyr Lys Ala Thr Asp Pro Gly Ile Leu Ile Asn
                    195                 200                 205

Ile Tyr Tyr Pro Val Pro Thr Ser Tyr Thr Pro Ala Gly Pro Pro Val
                210                 215                 220
```

Asp Thr Cys
225

<210> SEQ ID NO 13
<211> LENGTH: 255
<212> TYPE: PRT
<213> ORGANISM: Myceliophthora thermophila

<400> SEQUENCE: 13

| Met | Tyr | Arg | Thr | Leu | Gly | Ser | Ile | Ala | Leu | Leu | Ala | Gly | Gly | Ala | Ala |
|-----|-----|-----|-----|-----|-----|-----|-----|-----|-----|-----|-----|-----|-----|-----|-----|
| 1 | | | | 5 | | | | | 10 | | | | | 15 | |

Ala His Gly Ala Val Thr Ser Tyr Asn Ile Ala Gly Lys Asp Tyr Pro
            20                  25                  30

Gly Tyr Ser Gly Phe Ala Pro Thr Gly Gln Asp Val Ile Gln Trp Gln
        35                  40                  45

Trp Pro Asp Tyr Asn Pro Val Leu Ser Ala Ser Asp Pro Lys Leu Arg
50                  55                  60

Cys Asn Gly Gly Thr Gly Ala Ala Leu Tyr Ala Glu Ala Ala Pro Gly
65                  70                  75                  80

Asp Thr Ile Thr Ala Thr Trp Ala Gln Trp Thr His Ser Gln Gly Pro
                85                  90                  95

Ile Leu Val Trp Met Tyr Lys Cys Pro Gly Asp Phe Ser Ser Cys Asp
            100                 105                 110

Gly Ser Gly Ala Gly Trp Phe Lys Ile Asp Glu Ala Gly Phe His Gly
        115                 120                 125

Asp Gly Thr Thr Val Phe Leu Asp Thr Glu Thr Pro Ser Gly Trp Asp
    130                 135                 140

Ile Ala Lys Leu Val Gly Gly Asn Lys Ser Trp Ser Ser Lys Ile Pro
145                 150                 155                 160

Asp Gly Leu Ala Pro Gly Asn Tyr Leu Val Arg His Glu Leu Ile Ala
                165                 170                 175

Leu His Gln Ala Asn Asn Pro Gln Phe Tyr Pro Glu Cys Ala Gln Ile
            180                 185                 190

Lys Val Thr Gly Ser Gly Thr Ala Glu Pro Ala Ala Ser Tyr Lys Ala
        195                 200                 205

Ala Ile Pro Gly Tyr Cys Gln Gln Ser Asp Pro Asn Ile Ser Phe Asn
    210                 215                 220

Ile Asn Asp His Ser Leu Pro Gln Glu Tyr Lys Ile Pro Gly Pro Pro
225                 230                 235                 240

Val Phe Lys Gly Thr Ala Ser Ala Lys Ala Arg Ala Phe Gln Ala
                245                 250                 255

<210> SEQ ID NO 14
<211> LENGTH: 225
<212> TYPE: PRT
<213> ORGANISM: Myceliophthora thermophila

<400> SEQUENCE: 14

Met Leu Thr Thr Thr Phe Ala Leu Leu Thr Ala Ala Leu Gly Val Ser
1               5                   10                  15

Ala His Tyr Thr Leu Pro Arg Val Gly Thr Gly Ser Asp Trp Gln His
            20                  25                  30

Val Arg Arg Ala Asp Asn Trp Gln Asn Asn Gly Phe Val Gly Asp Val
        35                  40                  45

Asn Ser Glu Gln Ile Arg Cys Phe Gln Ala Thr Pro Ala Gly Ala Gln
    50                  55                  60

-continued

Asp Val Tyr Thr Val Gln Ala Gly Ser Thr Val Thr Tyr His Ala Asn
 65                  70                  75                  80

Pro Ser Ile Tyr His Pro Gly Pro Met Gln Phe Tyr Leu Ala Arg Val
                 85                  90                  95

Pro Asp Gly Gln Asp Val Lys Ser Trp Thr Gly Glu Gly Ala Val Trp
            100                 105                 110

Phe Lys Val Tyr Glu Glu Gln Pro Gln Phe Gly Ala Gln Leu Thr Trp
        115                 120                 125

Pro Ser Asn Gly Lys Ser Ser Phe Glu Val Pro Ile Pro Ser Cys Ile
130                 135                 140

Arg Ala Gly Asn Tyr Leu Leu Arg Ala Glu His Ile Ala Leu His Val
145                 150                 155                 160

Ala Gln Ser Gln Gly Gly Ala Gln Phe Tyr Ile Ser Cys Ala Gln Leu
                165                 170                 175

Gln Val Thr Gly Gly Ser Thr Glu Pro Ser Gln Lys Val Ser Phe
            180                 185                 190

Pro Gly Ala Tyr Lys Ser Thr Asp Pro Gly Ile Leu Ile Asn Ile Asn
        195                 200                 205

Tyr Pro Val Pro Thr Ser Tyr Gln Asn Pro Gly Pro Ala Val Phe Arg
    210                 215                 220

Cys
225

<210> SEQ ID NO 15
<211> LENGTH: 237
<212> TYPE: PRT
<213> ORGANISM: Myceliophthora thermophila

<400> SEQUENCE: 15

Met Lys Val Leu Ala Pro Leu Ile Leu Ala Gly Ala Ala Ser Ala His
  1               5                  10                  15

Thr Ile Phe Ser Ser Leu Glu Val Gly Gly Val Asn Gln Gly Ile Gly
             20                  25                  30

Gln Gly Val Arg Val Pro Ser Tyr Asn Gly Pro Ile Glu Asp Val Thr
         35                  40                  45

Ser Asn Ser Ile Ala Cys Asn Gly Pro Pro Asn Pro Thr Thr Pro Thr
 50                  55                  60

Asn Lys Val Ile Thr Val Arg Ala Gly Glu Thr Val Thr Ala Val Trp
 65                  70                  75                  80

Arg Tyr Met Leu Ser Thr Thr Gly Ser Ala Pro Asn Asp Ile Met Asp
                 85                  90                  95

Ser Ser His Lys Gly Pro Thr Met Ala Tyr Leu Lys Lys Val Asp Asn
            100                 105                 110

Ala Thr Thr Asp Ser Gly Val Gly Gly Gly Trp Phe Lys Ile Gln Glu
        115                 120                 125

Asp Gly Leu Thr Asn Gly Val Trp Gly Thr Glu Arg Val Ile Asn Gly
130                 135                 140

Gln Gly Arg His Asn Ile Lys Ile Pro Glu Cys Ile Ala Pro Gly Gln
145                 150                 155                 160

Tyr Leu Leu Arg Ala Glu Met Leu Ala Leu His Gly Ala Ser Asn Tyr
                165                 170                 175

Pro Gly Ala Gln Phe Tyr Met Glu Cys Ala Gln Leu Asn Ile Val Gly
            180                 185                 190

Gly Thr Gly Ser Lys Thr Pro Ser Thr Val Ser Phe Pro Gly Ala Tyr
        195                 200                 205

Lys Gly Thr Asp Pro Gly Val Lys Ile Asn Ile Tyr Trp Pro Pro Val
    210                 215                 220

Thr Ser Tyr Gln Ile Pro Gly Pro Gly Val Phe Thr Cys
225                 230                 235

<210> SEQ ID NO 16
<211> LENGTH: 246
<212> TYPE: PRT
<213> ORGANISM: Myceliophthora thermophila

<400> SEQUENCE: 16

Met Lys Leu Ser Leu Phe Ser Val Leu Ala Thr Ala Leu Thr Val Glu
1               5                   10                  15

Gly His Ala Ile Phe Gln Lys Val Ser Val Asn Gly Ala Asp Gln Gly
                20                  25                  30

Ser Leu Thr Gly Leu Arg Ala Pro Asn Asn Asn Asn Pro Val Gln Asn
            35                  40                  45

Val Asn Ser Gln Asp Met Ile Cys Gly Gln Ser Gly Ser Thr Ser Asn
    50                  55                  60

Thr Ile Ile Glu Val Lys Ala Gly Asp Arg Ile Gly Ala Trp Tyr Gln
65                  70                  75                  80

His Val Ile Gly Gly Ala Gln Phe Pro Asn Asp Pro Asp Asn Pro Ile
                85                  90                  95

Ala Lys Ser His Lys Gly Pro Val Met Ala Tyr Leu Ala Lys Val Asp
                100                 105                 110

Asn Ala Ala Thr Ala Ser Lys Thr Gly Leu Lys Trp Phe Lys Ile Trp
            115                 120                 125

Glu Asp Thr Phe Asn Pro Ser Thr Lys Thr Trp Gly Val Asp Asn Leu
    130                 135                 140

Ile Asn Asn Asn Gly Trp Val Tyr Phe Asn Leu Pro Gln Cys Ile Ala
145                 150                 155                 160

Asp Gly Asn Tyr Leu Leu Arg Val Glu Val Leu Ala Leu His Ser Ala
                165                 170                 175

Tyr Ser Gln Gly Gln Ala Gln Phe Tyr Gln Ser Cys Ala Gln Ile Asn
                180                 185                 190

Val Ser Gly Gly Gly Ser Phe Thr Pro Ala Ser Thr Val Ser Phe Pro
            195                 200                 205

Gly Ala Tyr Ser Ala Ser Asp Pro Gly Ile Leu Ile Asn Ile Tyr Gly
    210                 215                 220

Ala Thr Gly Gln Pro Asp Asn Asn Gly Gln Pro Tyr Thr Ala Pro Gly
225                 230                 235                 240

Pro Ala Pro Ile Ser Cys
                245

<210> SEQ ID NO 17
<211> LENGTH: 254
<212> TYPE: PRT
<213> ORGANISM: Myceliophthora thermophila

<400> SEQUENCE: 17

Met Ala Leu Gln Leu Leu Ala Ser Leu Ala Leu Leu Ser Val Pro Ala
1               5                   10                  15

Leu Ala His Gly Gly Leu Ala Asn Tyr Thr Val Gly Asp Thr Trp Tyr
                20                  25                  30

Arg Gly Tyr Asp Pro Asn Leu Pro Pro Glu Thr Gln Leu Asn Gln Thr
            35                  40                  45

-continued

```
Trp Met Ile Gln Arg Gln Trp Ala Thr Ile Asp Pro Val Phe Thr Val
    50                  55                  60

Ser Glu Pro Tyr Leu Ala Cys Asn Asn Pro Gly Ala Pro Pro Ser
65                  70                  75                  80

Tyr Ile Pro Ile Arg Ala Gly Asp Lys Ile Thr Ala Val Tyr Trp Tyr
                85                  90                  95

Trp Leu His Ala Ile Gly Pro Met Ser Val Trp Leu Ala Arg Cys Gly
                100                 105                 110

Asp Thr Pro Ala Ala Asp Cys Arg Asp Val Asp Val Asn Arg Val Gly
                115                 120                 125

Trp Phe Lys Ile Trp Glu Gly Gly Leu Leu Glu Gly Pro Asn Leu Ala
            130                 135                 140

Glu Gly Leu Trp Tyr Gln Lys Asp Phe Gln Arg Trp Asp Gly Ser Pro
145                 150                 155                 160

Ser Leu Trp Pro Val Thr Ile Pro Lys Gly Leu Lys Ser Gly Thr Tyr
                165                 170                 175

Ile Ile Arg His Glu Ile Leu Ser Leu His Val Ala Leu Lys Pro Gln
                180                 185                 190

Phe Tyr Pro Glu Cys Ala His Leu Asn Ile Thr Gly Gly Gly Asp Leu
                195                 200                 205

Leu Pro Pro Glu Glu Thr Leu Val Arg Phe Pro Gly Val Tyr Lys Glu
210                 215                 220

Asp Asp Pro Ser Ile Phe Ile Asp Val Tyr Ser Glu Glu Asn Ala Asn
225                 230                 235                 240

Arg Thr Asp Tyr Thr Val Pro Gly Gly Pro Ile Trp Glu Gly
                245                 250

<210> SEQ ID NO 18
<211> LENGTH: 235
<212> TYPE: PRT
<213> ORGANISM: Myceliophthora thermophila

<400> SEQUENCE: 18

Met Lys Ala Leu Ser Leu Leu Ala Ala Ala Gly Ala Val Ser Ala His
1               5                   10                  15

Thr Ile Phe Val Gln Leu Glu Ala Asp Gly Thr Arg Tyr Pro Val Ser
                20                  25                  30

Tyr Gly Ile Arg Asp Pro Thr Tyr Asp Gly Pro Ile Thr Asp Val Thr
                35                  40                  45

Ser Asn Asp Val Ala Cys Asn Gly Gly Pro Asn Pro Thr Thr Pro Ser
    50                  55                  60

Ser Asp Val Ile Thr Val Thr Ala Gly Thr Thr Val Lys Ala Ile Trp
65                  70                  75                  80

Arg His Thr Leu Gln Ser Gly Pro Asp Asp Val Met Asp Ala Ser His
                85                  90                  95

Lys Gly Pro Thr Leu Ala Tyr Ile Lys Lys Val Gly Asp Ala Thr Lys
                100                 105                 110

Asp Ser Gly Val Gly Gly Gly Trp Phe Lys Ile Gln Glu Asp Gly Tyr
            115                 120                 125

Asn Asn Gly Gln Trp Gly Thr Ser Thr Val Ile Ser Asn Gly Gly Glu
            130                 135                 140

His Tyr Ile Asp Ile Pro Ala Cys Ile Pro Glu Gly Gln Tyr Leu Leu
145                 150                 155                 160

Arg Ala Glu Met Ile Ala Leu His Ala Ala Gly Ser Pro Gly Gly Ala
```

```
                    165                 170                 175
Gln Leu Tyr Met Glu Cys Ala Gln Ile Asn Ile Val Gly Gly Ser Gly
            180                 185                 190

Ser Val Pro Ser Ser Thr Val Ser Phe Pro Gly Ala Tyr Ser Pro Asn
            195                 200                 205

Asp Pro Gly Leu Leu Ile Asn Ile Tyr Ser Met Ser Pro Ser Ser Ser
            210                 215                 220

Tyr Thr Ile Pro Gly Pro Pro Val Phe Lys Cys
225                 230                 235

<210> SEQ ID NO 19
<211> LENGTH: 304
<212> TYPE: PRT
<213> ORGANISM: Myceliophthora thermophila

<400> SEQUENCE: 19

Met Lys Ser Ser Thr Pro Ala Leu Phe Ala Ala Gly Leu Leu Ala Gln
1               5                   10                  15

His Ala Ala His Ser Ile Phe Gln Gln Ala Ser Ser Gly Ser Thr
            20                  25                  30

Asp Phe Asp Thr Leu Cys Thr Arg Met Pro Asn Asn Ser Pro Val
        35                  40                  45

Thr Ser Val Thr Ser Gly Asp Met Thr Cys Lys Val Gly Gly Thr Lys
50                  55                  60

Gly Val Ser Gly Phe Cys Glu Val Asn Ala Gly Asp Glu Phe Thr Val
65                  70                  75                  80

Glu Met His Ala Gln Pro Gly Asp Arg Ser Cys Ala Asn Glu Ala Ile
                85                  90                  95

Gly Gly Asn His Phe Gly Pro Val Leu Ile Tyr Met Ser Lys Val Asp
            100                 105                 110

Asp Ala Ser Thr Ala Asp Gly Ser Gly Asp Trp Phe Lys Val Asp Glu
        115                 120                 125

Phe Gly Tyr Asp Ala Ser Thr Lys Thr Trp Gly Thr Asp Lys Leu Asn
130                 135                 140

Glu Asn Cys Gly Lys Arg Thr Phe Asn Ile Pro Ser His Ile Pro Ala
145                 150                 155                 160

Gly Asp Tyr Leu Val Arg Ala Glu Ala Ile Ala Leu His Thr Ala Asn
                165                 170                 175

Gln Pro Gly Gly Ala Gln Phe Tyr Met Ser Cys Tyr Gln Val Arg Ile
            180                 185                 190

Ser Gly Gly Glu Gly Gly Leu Pro Ala Gly Val Lys Ile Pro Gly
        195                 200                 205

Ala Tyr Ser Ala Asn Asp Pro Gly Ile Leu Val Asp Ile Trp Gly Asn
210                 215                 220

Asp Phe Asn Asp Pro Gly His Ser Ala Arg His Ala Ile Ile Ile
225                 230                 235                 240

Ile Ser Ser Ser Ser Asn Asn Ser Gly Ala Lys Met Thr Lys Lys Ile
                245                 250                 255

Gln Glu Pro Thr Ile Thr Ser Val Thr Asp Leu Pro Thr Asp Glu Ala
            260                 265                 270

Lys Trp Ile Ala Leu Gln Lys Ile Ser Tyr Val Asp Gln Thr Gly Thr
        275                 280                 285

Ala Arg Thr Tyr Glu Pro Ala Ser Arg Lys Thr Arg Ser Pro Arg Val
290                 295                 300
```

<210> SEQ ID NO 20
<211> LENGTH: 323
<212> TYPE: PRT
<213> ORGANISM: Myceliophthora thermophila

<400> SEQUENCE: 20

Met Lys Ser Phe Thr Leu Thr Thr Leu Ala Leu Ala Gly Asn Ala
1               5                   10                  15

Ala Ala His Ala Thr Phe Gln Ala Leu Trp Val Asp Gly Val Asp Tyr
            20                  25                  30

Gly Ala Gln Cys Ala Arg Leu Pro Ala Ser Asn Ser Pro Val Thr Asp
        35                  40                  45

Val Thr Ser Asn Ala Ile Arg Cys Asn Ala Asn Pro Ser Pro Ala Arg
    50                  55                  60

Gly Lys Cys Pro Val Lys Ala Gly Ser Thr Val Thr Val Glu Met His
65                  70                  75                  80

Gln Gln Pro Gly Asp Arg Ser Cys Ser Ser Glu Ala Ile Gly Ala
                85                  90                  95

His Tyr Gly Pro Val Met Val Tyr Met Ser Lys Val Ser Asp Ala Ala
            100                 105                 110

Ser Ala Asp Gly Ser Ser Gly Trp Phe Lys Val Phe Glu Asp Gly Trp
        115                 120                 125

Ala Lys Asn Pro Ser Gly Gly Ser Gly Asp Asp Tyr Trp Gly Thr
    130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Ala Gln Phe Tyr Met Thr Cys Tyr
            180                 185                 190

Gln Leu Thr Val Thr Gly Ser Gly Ser Ala Ser Pro Pro Thr Val Ser
        195                 200                 205

Phe Pro Gly Ala Tyr Lys Ala Thr Asp Pro Gly Ile Leu Val Asn Ile
    210                 215                 220

His Ala Pro Leu Ser Gly Tyr Thr Val Pro Gly Pro Ala Val Tyr Ser
225                 230                 235                 240

Gly Gly Ser Thr Lys Lys Ala Gly Ser Ala Cys Thr Gly Cys Glu Ser
                245                 250                 255

Thr Cys Ala Val Gly Ser Gly Pro Thr Ala Thr Val Ser Gln Ser Pro
            260                 265                 270

Gly Ser Thr Ala Thr Ser Ala Pro Gly Gly Gly Gly Cys Thr Val
        275                 280                 285

Gln Lys Tyr Gln Gln Cys Gly Gly Gln Gly Tyr Thr Gly Cys Thr Asn
    290                 295                 300

Cys Ala Ser Gly Ser Thr Cys Ser Ala Val Ser Pro Pro Tyr Tyr Ser
305                 310                 315                 320

Gln Cys Val

<210> SEQ ID NO 21
<211> LENGTH: 289
<212> TYPE: PRT
<213> ORGANISM: Myceliophthora thermophila

<400> SEQUENCE: 21

Met Lys Gly Leu Leu Gly Ala Ala Ala Leu Ser Leu Ala Val Ser Asp

```
  1               5                   10                  15
Val Ser Ala His Tyr Ile Phe Gln Gln Leu Thr Thr Gly Gly Val Lys
                20                  25                  30
His Ala Val Tyr Gln Tyr Ile Arg Lys Asn Thr Asn Tyr Asn Ser Pro
                35                  40                  45
Val Thr Asp Leu Thr Ser Asn Asp Leu Arg Cys Asn Val Gly Ala Thr
 50                      55                  60
Gly Ala Gly Thr Asp Thr Val Thr Val Arg Ala Gly Asp Ser Phe Thr
 65                      70                  75                  80
Phe Thr Thr Asp Thr Pro Val Tyr His Gln Gly Pro Thr Ser Ile Tyr
                85                  90                  95
Met Ser Lys Ala Pro Gly Ser Ala Ser Asp Tyr Asp Gly Ser Gly Gly
                100                 105                 110
Trp Phe Lys Ile Lys Asp Trp Ala Asp Tyr Thr Ala Thr Ile Pro Glu
                115                 120                 125
Cys Ile Pro Pro Gly Asp Tyr Leu Leu Arg Ile Gln Gln Leu Gly Ile
                130                 135                 140
His Asn Pro Trp Pro Ala Gly Ile Pro Gln Phe Tyr Ile Ser Cys Ala
145                     150                 155                 160
Gln Ile Thr Val Thr Gly Gly Ser Ala Asn Pro Gly Pro Thr Val
                165                 170                 175
Ser Ile Pro Gly Ala Phe Lys Glu Thr Asp Pro Gly Tyr Thr Val Asn
                180                 185                 190
Ile Tyr Asn Asn Phe His Asn Tyr Thr Val Pro Gly Pro Ala Val Phe
                195                 200                 205
Thr Cys Asn Gly Ser Gly Gly Asn Gly Gly Ser Asn Pro Val
210                     215                 220
Thr Thr Thr Thr Thr Thr Thr Arg Pro Ser Thr Ser Thr Ala Gln
225                     230                 235                 240
Ser Gln Pro Ser Ser Pro Thr Ser Pro Ser Ser Cys Thr Val Ala
                245                 250                 255
Lys Trp Gly Gln Cys Gly Gly Gln Gly Tyr Ser Gly Cys Thr Val Cys
                260                 265                 270
Ala Ala Gly Ser Thr Cys Gln Lys Thr Asn Asp Tyr Tyr Ser Gln Cys
                275                 280                 285
Leu
```

<210> SEQ ID NO 22
<211> LENGTH: 346
<212> TYPE: PRT
<213> ORGANISM: Myceliophthora thermophila

<400> SEQUENCE: 22

```
Met Ser Ser Phe Thr Ser Lys Gly Leu Leu Ser Ala Leu Met Gly Ala
 1               5                   10                  15
Ala Thr Val Ala Ala His Gly His Val Thr Asn Ile Val Ile Asn Gly
                20                  25                  30
Val Ser Tyr Gln Asn Phe Asp Pro Phe Thr His Pro Tyr Met Gln Asn
                35                  40                  45
Pro Pro Thr Val Val Gly Trp Thr Ala Ser Asn Thr Asp Asn Gly Phe
 50                      55                  60
Val Gly Pro Glu Ser Phe Ser Ser Pro Asp Ile Ile Cys His Lys Ser
 65                      70                  75                  80
Ala Thr Asn Ala Gly Gly His Ala Val Val Ala Ala Gly Asp Lys Val
```

```
                85                  90                  95
Phe Ile Gln Trp Asp Thr Trp Pro Glu Ser His His Gly Pro Val Ile
            100                 105                 110
Asp Tyr Leu Ala Asp Cys Gly Asp Ala Gly Cys Glu Lys Val Asp Lys
            115                 120                 125
Thr Thr Leu Lys Phe Phe Lys Ile Ser Glu Ser Gly Leu Leu Asp Gly
            130                 135                 140
Thr Asn Ala Pro Gly Lys Trp Ala Ser Asp Thr Leu Ile Ala Asn Asn
145                 150                 155                 160
Asn Ser Trp Leu Val Gln Ile Pro Pro Asn Ile Ala Pro Gly Asn Tyr
                165                 170                 175
Val Leu Arg His Glu Ile Ile Ala Leu His Ser Ala Gly Gln Gln Asn
            180                 185                 190
Gly Ala Gln Asn Tyr Pro Gln Cys Phe Asn Leu Gln Val Thr Gly Ser
            195                 200                 205
Gly Thr Gln Lys Pro Ser Gly Val Leu Gly Thr Glu Leu Tyr Lys Ala
            210                 215                 220
Thr Asp Ala Gly Ile Leu Ala Asn Ile Tyr Thr Ser Pro Val Thr Tyr
225                 230                 235                 240
Gln Ile Pro Gly Pro Ala Ile Ile Ser Gly Ala Ser Ala Val Gln Gln
                245                 250                 255
Thr Thr Ser Ala Ile Thr Ala Ser Ala Ser Ala Ile Thr Gly Ser Ala
            260                 265                 270
Thr Ala Ala Pro Thr Ala Ala Thr Thr Ala Ala Ala Ala Thr
            275                 280                 285
Thr Thr Thr Thr Ala Gly Ser Gly Ala Thr Ala Thr Pro Ser Thr Gly
            290                 295                 300
Gly Ser Pro Ser Ser Ala Gln Pro Ala Pro Thr Thr Ala Ala Ala Thr
305                 310                 315                 320
Ser Ser Pro Ala Arg Pro Thr Arg Cys Ala Gly Leu Lys Lys Arg Arg
                325                 330                 335
Arg His Ala Arg Asp Val Lys Val Ala Leu
            340                 345

<210> SEQ ID NO 23
<211> LENGTH: 237
<212> TYPE: PRT
<213> ORGANISM: Myceliophthora thermophila

<400> SEQUENCE: 23

Met Lys Thr Leu Ala Ala Leu Val Val Ser Ala Ala Leu Val Ala Ala
1               5                   10                  15
His Gly Tyr Val Asp His Ala Thr Ile Gly Gly Lys Asp Tyr Gln Phe
            20                  25                  30
Tyr Gln Pro Tyr Gln Asp Pro Tyr Met Gly Asp Asn Lys Pro Asp Arg
            35                  40                  45
Val Ser Arg Ser Ile Pro Gly Asn Gly Pro Val Glu Asp Val Asn Ser
        50                  55                  60
Ile Asp Leu Gln Cys His Ala Gly Ala Glu Pro Ala Lys Leu His Ala
65                  70                  75                  80
Pro Ala Ala Gly Ser Thr Val Thr Leu Tyr Trp Thr Leu Trp Pro
                85                  90                  95
Asp Ser His Val Gly Pro Val Ile Thr Tyr Met Ala Arg Cys Pro Asp
            100                 105                 110
```

```
Thr Gly Cys Gln Asp Trp Ser Pro Gly Thr Lys Pro Val Trp Phe Lys
            115                 120                 125

Ile Lys Glu Gly Gly Arg Glu Gly Thr Ser Asn Thr Pro Leu Met Thr
130                 135                 140

Ala Pro Ser Ala Tyr Thr Tyr Thr Ile Pro Ser Cys Leu Lys Ser Gly
145                 150                 155                 160

Tyr Tyr Leu Val Arg His Glu Ile Ile Ala Leu His Ser Ala Trp Gln
                165                 170                 175

Tyr Pro Gly Ala Gln Phe Tyr Pro Gly Cys His Gln Leu Gln Val Thr
            180                 185                 190

Gly Gly Gly Ser Thr Val Pro Ser Thr Asn Leu Val Ser Phe Pro Gly
        195                 200                 205

Ala Tyr Lys Gly Ser Asp Pro Gly Ile Thr Tyr Asp Ala Tyr Lys Ala
    210                 215                 220

Gln Pro Tyr Thr Ile Pro Gly Pro Ala Val Phe Thr Cys
225                 230                 235

<210> SEQ ID NO 24
<211> LENGTH: 225
<212> TYPE: PRT
<213> ORGANISM: Myceliophthora thermophila

<400> SEQUENCE: 24

Met Arg Tyr Phe Leu Gln Leu Ala Ala Ala Ala Phe Ala Val Asn
1               5                   10                  15

Ser Ala Ala Gly His Tyr Ile Phe Gln Gln Phe Ala Thr Gly Gly Ser
            20                  25                  30

Lys Tyr Pro Pro Trp Lys Tyr Ile Arg Arg Asn Thr Asn Pro Asp Trp
        35                  40                  45

Leu Gln Asn Gly Pro Val Thr Asp Leu Ser Ser Thr Asp Leu Arg Cys
    50                  55                  60

Asn Val Gly Gly Gln Val Ser Asn Gly Thr Glu Thr Ile Thr Leu Asn
65                  70                  75                  80

Ala Gly Asp Glu Phe Ser Phe Ile Leu Asp Thr Pro Val Tyr His Ala
                85                  90                  95

Gly Pro Thr Ser Leu Tyr Met Ser Lys Ala Pro Gly Ala Val Ala Asp
            100                 105                 110

Tyr Asp Gly Gly Ala Trp Phe Lys Ile Tyr Asp Trp Gly Pro Ser
        115                 120                 125

Gly Thr Ser Trp Thr Leu Ser Gly Thr Tyr Gln Arg Ile Pro Lys
    130                 135                 140

Cys Ile Pro Asp Gly Glu Tyr Leu Leu Arg Ile Gln Gln Ile Gly Leu
145                 150                 155                 160

His Asn Pro Gly Ala Ala Pro Gln Phe Tyr Ile Ser Cys Ala Gln Val
                165                 170                 175

Lys Val Val Asp Gly Gly Ser Thr Asn Pro Thr Pro Thr Ala Gln Ile
            180                 185                 190

Pro Gly Ala Phe His Ser Asn Asp Pro Gly Leu Thr Val Asn Ile Tyr
        195                 200                 205

Asn Asp Pro Leu Thr Asn Tyr Val Val Pro Gly Pro Arg Val Ser His
    210                 215                 220

Trp
225

<210> SEQ ID NO 25
```

```
<211> LENGTH: 444
<212> TYPE: PRT
<213> ORGANISM: Myceliophthora thermophila

<400> SEQUENCE: 25

Met His Pro Ser Leu Leu Phe Thr Leu Gly Leu Ala Ser Val Leu Val
1               5                   10                  15

Pro Leu Ser Ser Ala His Thr Thr Phe Thr Thr Leu Phe Val Asn Asp
            20                  25                  30

Val Asn Gln Gly Asp Gly Thr Cys Ile Arg Met Ala Lys Lys Gly Asn
        35                  40                  45

Val Ala Thr His Pro Leu Ala Gly Gly Leu Asp Ser Glu Asp Met Ala
    50                  55                  60

Cys Gly Arg Asp Gly Gln Glu Pro Val Ala Phe Thr Cys Pro Ala Pro
65                  70                  75                  80

Ala Gly Ala Lys Leu Thr Leu Glu Phe Arg Met Trp Ala Asp Ala Ser
                85                  90                  95

Gln Ser Gly Ser Ile Asp Pro Ser His Leu Gly Val Met Ala Ile Tyr
            100                 105                 110

Leu Lys Lys Val Ser Asp Met Lys Ser Asp Ala Ala Ala Gly Pro Gly
        115                 120                 125

Trp Phe Lys Ile Trp Asp Gln Gly Tyr Asp Leu Ala Ala Lys Lys Trp
    130                 135                 140

Ala Thr Glu Lys Leu Ile Asp Asn Asn Gly Leu Leu Ser Val Asn Leu
145                 150                 155                 160

Pro Thr Gly Leu Pro Thr Gly Tyr Tyr Leu Ala Arg Gln Glu Ile Ile
                165                 170                 175

Thr Leu Gln Asn Val Thr Asn Asp Arg Pro Glu Pro Gln Phe Tyr Val
            180                 185                 190

Gly Cys Ala Gln Leu Tyr Val Glu Gly Thr Ser Asp Ser Pro Ile Pro
        195                 200                 205

Ser Asp Lys Thr Val Ser Ile Pro Gly His Ile Ser Asp Pro Ala Asp
    210                 215                 220

Pro Gly Leu Thr Phe Asn Val Tyr Thr Gly Asp Ala Ser Thr Tyr Lys
225                 230                 235                 240

Pro Pro Gly Pro Glu Val Tyr Phe Pro Thr Thr Thr Thr Thr Thr Ser
                245                 250                 255

Ser Ser Ser Ser Gly Ser Ser Asp Asn Lys Gly Ala Arg Arg Gln Gln
            260                 265                 270

Thr Pro Asp Asp Lys Gln Ala Asp Gly Leu Val Pro Ala Asp Cys Leu
        275                 280                 285

Val Lys Asn Ala Asn Trp Cys Ala Ala Ala Leu Pro Pro Tyr Thr Asp
    290                 295                 300

Glu Ala Gly Cys Trp Ala Ala Ala Glu Asp Cys Asn Lys Gln Leu Asp
305                 310                 315                 320

Ala Cys Tyr Thr Ser Ala Pro Pro Ser Gly Ser Lys Gly Cys Lys Val
                325                 330                 335

Trp Glu Glu Gln Val Cys Thr Val Val Ser Gln Lys Cys Glu Ala Gly
            340                 345                 350

Asp Phe Lys Gly Pro Pro Gln Leu Gly Lys Glu Leu Gly Glu Gly Ile
        355                 360                 365

Asp Glu Pro Ile Pro Gly Gly Lys Leu Pro Pro Ala Val Asn Ala Gly
    370                 375                 380

Glu Asn Gly Asn His Gly Gly Gly Gly Gly Asp Asp Gly Asp Asp Asp
```

Asn Asp Glu Ala Gly Ala Gly Ala Ala Ser Thr Pro Thr Phe Ala Ala
            385                 390                 395                 400

Pro Gly Ala Ala Lys Thr Pro Gln Pro Asn Ser Glu Arg Ala Arg Arg
            405                 410                 415

Arg Glu Ala His Trp Arg Arg Leu Glu Ser Ala Glu
            420                 425                 430

435                 440

<210> SEQ ID NO 26
<211> LENGTH: 232
<212> TYPE: PRT
<213> ORGANISM: Myceliophthora thermophila

<400> SEQUENCE: 26

Met Lys Leu Thr Ser Ser Leu Ala Val Leu Ala Ala Gly Ala Gln
1               5                   10                  15

Ala His Tyr Thr Phe Pro Arg Ala Gly Thr Gly Gly Ser Leu Ser Gly
            20                  25                  30

Glu Trp Glu Val Val Arg Met Thr Glu Asn His Tyr Ser His Gly Pro
        35                  40                  45

Val Thr Asp Val Thr Ser Pro Glu Met Thr Cys Tyr Gln Ser Gly Val
    50                  55                  60

Gln Gly Ala Pro Gln Thr Val Gln Val Lys Ala Gly Ser Gln Phe Thr
65                  70                  75                  80

Phe Ser Val Asp Pro Ser Ile Gly His Pro Gly Pro Leu Gln Phe Tyr
                85                  90                  95

Met Ala Lys Val Pro Ser Gly Gln Thr Ala Ala Thr Phe Asp Gly Thr
            100                 105                 110

Gly Ala Val Trp Phe Lys Ile Tyr Gln Asp Gly Pro Asn Gly Leu Gly
        115                 120                 125

Thr Asp Ser Ile Thr Trp Pro Ser Ala Gly Lys Thr Glu Val Ser Val
    130                 135                 140

Thr Ile Pro Ser Cys Ile Glu Asp Gly Glu Tyr Leu Leu Arg Val Glu
145                 150                 155                 160

His Ile Ala Leu His Ser Ala Ser Ser Val Gly Gly Ala Gln Phe Tyr
                165                 170                 175

Ile Ala Cys Ala Gln Leu Ser Val Thr Gly Gly Ser Gly Thr Leu Asn
            180                 185                 190

Thr Gly Ser Leu Val Ser Leu Pro Gly Ala Tyr Lys Ala Thr Asp Pro
        195                 200                 205

Gly Ile Leu Phe Gln Leu Tyr Trp Pro Ile Pro Thr Glu Tyr Ile Asn
    210                 215                 220

Pro Gly Pro Ala Pro Val Ser Cys
225                 230

<210> SEQ ID NO 27
<211> LENGTH: 392
<212> TYPE: PRT
<213> ORGANISM: Myceliophthora thermophila

<400> SEQUENCE: 27

Met Pro Pro Pro Arg Leu Ser Thr Leu Leu Pro Leu Leu Ala Leu Ile
1               5                   10                  15

Ala Pro Thr Ala Leu Gly His Ser His Leu Gly Tyr Ile Ile Ile Asn
            20                  25                  30

Gly Glu Val Tyr Gln Gly Phe Asp Pro Arg Pro Glu Gln Ala Asn Ser

```
                35                  40                  45
Pro Leu Arg Val Gly Trp Ser Thr Gly Ala Ile Asp Asp Gly Phe Val
 50                  55                  60

Ala Pro Ala Asn Tyr Ser Ser Pro Asp Ile Ile Cys His Ile Glu Gly
 65                  70                  75                  80

Ala Ser Pro Pro Ala His Ala Pro Val Arg Ala Gly Asp Arg Val His
                 85                  90                  95

Val Gln Trp Lys Arg Leu Ala Ala Arg Thr Arg Gly Ala Gly Ala Val
            100                 105                 110

Val Pro Gly Ala Leu Arg Arg Ala Gly Val Arg Glu Arg Val Asp
        115                 120                 125

Asp Ser Leu Pro Ala Met Glu Leu Val Gly Ala Ala Gly Gly Ala Gly
        130                 135                 140

Gly Glu Asp Asp Gly Ser Gly Ser Asp Gly Ser Gly Ser Gly Gly Ser
145                 150                 155                 160

Gly Arg Val Gly Val Pro Gly Gln Arg Trp Ala Thr Asp Val Leu Ile
                165                 170                 175

Ala Ala Asn Asn Ser Trp Gln Val Glu Ile Pro Arg Gly Leu Arg Asp
            180                 185                 190

Gly Pro Tyr Val Leu Arg His Glu Ile Val Ala Leu His Tyr Ala Ala
        195                 200                 205

Glu Pro Gly Gly Ala Gln Asn Tyr Pro Leu Cys Val Asn Leu Trp Val
210                 215                 220

Glu Gly Gly Asp Gly Ser Met Glu Leu Asp His Phe Asp Ala Thr Gln
225                 230                 235                 240

Phe Tyr Arg Pro Asp Asp Pro Gly Ile Leu Leu Asn Val Thr Ala Gly
                245                 250                 255

Leu Arg Ser Tyr Ala Val Pro Gly Pro Thr Leu Ala Ala Gly Ala Thr
            260                 265                 270

Pro Val Pro Tyr Ala Gln Gln Asn Ile Ser Ser Ala Arg Ala Asp Gly
        275                 280                 285

Thr Pro Val Ile Val Thr Arg Ser Thr Glu Thr Val Pro Phe Thr Ala
290                 295                 300

Ala Pro Thr Pro Ala Glu Thr Ala Glu Ala Lys Gly Gly Arg Tyr Asp
305                 310                 315                 320

Asp Gln Thr Arg Thr Lys Asp Leu Asn Glu Arg Phe Phe Tyr Ser Ser
                325                 330                 335

Arg Pro Glu Gln Lys Arg Leu Thr Ala Thr Ser Arg Arg Glu Leu Val
            340                 345                 350

Asp His Arg Thr Arg Tyr Leu Ser Val Ala Val Cys Ala Asp Phe Gly
        355                 360                 365

Ala His Lys Ala Ala Glu Thr Asn His Glu Ala Leu Arg Gly Gly Asn
        370                 375                 380

Lys His His Gly Gly Val Ser Glu
385                 390

<210> SEQ ID NO 28
<211> LENGTH: 279
<212> TYPE: PRT
<213> ORGANISM: Myceliophthora thermophila

<400> SEQUENCE: 28

Met Arg Ser Thr Leu Ala Gly Ala Leu Ala Ala Ile Ala Ala Gln Lys
 1               5                  10                  15
```

```
Val Ala Gly His Ala Thr Phe Gln Gln Leu Trp His Gly Ser Ser Cys
             20                  25                  30

Val Arg Leu Pro Ala Ser Asn Ser Pro Val Thr Asn Val Gly Ser Arg
             35                  40                  45

Asp Phe Val Cys Asn Ala Gly Thr Arg Pro Val Ser Gly Lys Cys Pro
             50                  55                  60

Val Lys Ala Gly Gly Thr Val Thr Ile Glu Met His Gln Gln Pro Gly
 65                  70                  75                  80

Asp Arg Ser Cys Asn Asn Glu Ala Ile Gly Gly Ala His Trp Gly Pro
                     85                  90                  95

Val Gln Val Tyr Leu Thr Lys Val Gln Asp Ala Ala Thr Ala Asp Gly
                100                 105                 110

Ser Thr Gly Trp Phe Lys Ile Phe Ser Asp Ser Trp Ser Lys Lys Pro
            115                 120                 125

Gly Gly Asn Ser Gly Asp Asp Asp Asn Trp Gly Thr Arg Asp Leu Asn
            130                 135                 140

Ala Cys Cys Gly Lys Met Asp Val Ala Ile Pro Ala Asp Ile Ala Ser
145                 150                 155                 160

Gly Asp Tyr Leu Leu Arg Ala Glu Ala Leu Ala Leu His Thr Ala Gly
                165                 170                 175

Gln Ala Gly Gly Ala Gln Phe Tyr Met Ser Cys Tyr Gln Met Thr Val
            180                 185                 190

Glu Gly Gly Ser Gly Thr Ala Asn Pro Pro Thr Val Lys Phe Pro Gly
            195                 200                 205

Ala Tyr Ser Ala Asn Asp Pro Gly Ile Leu Val Asn Ile His Ala Pro
210                 215                 220

Leu Ser Ser Tyr Thr Ala Pro Gly Pro Ala Val Tyr Ala Gly Gly Thr
225                 230                 235                 240

Ile Arg Glu Ala Gly Ser Ala Cys Thr Gly Cys Ala Gln Thr Cys Lys
                245                 250                 255

Val Gly Ser Ser Pro Ser Ala Val Ala Pro Gly Ser Gly Ala Gly Asn
            260                 265                 270

Gly Gly Gly Phe Gln Pro Arg
        275

<210> SEQ ID NO 29
<211> LENGTH: 231
<212> TYPE: PRT
<213> ORGANISM: Myceliophthora thermophila

<400> SEQUENCE: 29

Met Asn Tyr Leu Ala His Cys Thr Asn Asp Asp Cys Lys Ser Phe Lys
1               5                  10                  15

Gly Asp Ser Gly Asn Val Trp Val Lys Ile Glu Gln Leu Ala Tyr Asn
             20                  25                  30

Pro Ser Ala Asn Pro Pro Trp Ala Ser Asp Leu Leu Arg Glu His Gly
             35                  40                  45

Ala Lys Trp Lys Val Thr Ile Pro Pro Ser Leu Val Pro Gly Glu Tyr
 50                  55                  60

Leu Leu Arg His Glu Ile Leu Gly Leu His Val Ala Gly Thr Val Met
 65                  70                  75                  80

Gly Ala Gln Phe Tyr Pro Gly Cys Thr Gln Ile Arg Val Thr Glu Gly
                 85                  90                  95

Gly Ser Thr Gln Leu Pro Ser Gly Ile Ala Leu Pro Gly Ala Tyr Gly
                100                 105                 110
```

```
Pro Gln Asp Glu Gly Ile Leu Val Asp Leu Trp Arg Val Asn Gln Gly
        115                 120                 125

Gln Val Asn Tyr Thr Ala Pro Gly Pro Val Trp Ser Glu Ala Trp
    130                 135                 140

Asp Thr Glu Phe Gly Gly Ser Asn Thr Thr Glu Cys Ala Thr Met Leu
145                 150                 155                 160

Asp Asp Leu Leu Asp Tyr Met Ala Ala Asn Asp Pro Cys Cys Thr
                165                 170                 175

Asp Gln Asn Gln Phe Gly Ser Leu Glu Pro Gly Ser Lys Ala Ala Gly
                180                 185                 190

Gly Ser Pro Ser Leu Tyr Asp Thr Val Leu Val Pro Val Leu Gln Lys
        195                 200                 205

Lys Val Pro Thr Lys Leu Gln Trp Ser Gly Pro Ala Ser Val Asn Gly
        210                 215                 220

Asp Glu Leu Thr Glu Arg Pro
225                 230

<210> SEQ ID NO 30
<211> LENGTH: 242
<212> TYPE: PRT
<213> ORGANISM: Myceliophthora thermophila

<400> SEQUENCE: 30

Met Lys Ser Ser Thr Pro Ala Leu Phe Ala Ala Gly Leu Leu Ala Gln
1               5                   10                  15

His Ala Ala His Ser Ile Phe Gln Gln Ala Ser Ser Gly Ser Thr
            20                  25                  30

Asp Phe Asp Thr Leu Cys Thr Arg Met Pro Pro Asn Asn Ser Pro Val
                35                  40                  45

Thr Ser Val Thr Ser Gly Asp Met Thr Cys Asn Val Gly Gly Thr Lys
    50                  55                  60

Gly Val Ser Gly Phe Cys Glu Val Asn Ala Gly Asp Glu Phe Thr Val
65                  70                  75                  80

Glu Met His Ala Gln Pro Gly Asp Arg Ser Cys Ala Asn Glu Ala Ile
                85                  90                  95

Gly Gly Asn His Phe Gly Pro Val Leu Ile Tyr Met Ser Lys Val Asp
                100                 105                 110

Asp Ala Ser Thr Ala Asp Gly Ser Gly Asp Trp Phe Lys Val Asp Glu
            115                 120                 125

Phe Gly Tyr Asp Ala Ser Thr Lys Thr Trp Gly Thr Asp Lys Leu Asn
        130                 135                 140

Glu Asn Cys Gly Lys Arg Thr Phe Asn Ile Pro Ser His Ile Pro Ala
145                 150                 155                 160

Gly Asp Tyr Leu Val Arg Ala Glu Ala Ile Ala Leu His Thr Ala Asn
                165                 170                 175

Gln Pro Gly Gly Ala Gln Phe Tyr Met Ser Cys Tyr Gln Val Arg Ile
            180                 185                 190

Ser Gly Gly Glu Gly Gly Gln Leu Pro Ala Gly Val Lys Ile Pro Gly
        195                 200                 205

Ala Tyr Ser Ala Asn Asp Pro Gly Ile Leu Val Asp Ile Trp Gly Asn
        210                 215                 220

Asp Phe Asn Glu Tyr Val Ile Pro Gly Pro Pro Val Ile Asp Ser Ser
225                 230                 235                 240

Tyr Phe
```

```
<210> SEQ ID NO 31
<211> LENGTH: 1029
<212> TYPE: DNA
<213> ORGANISM: Myceliophthora thermophila

<400> SEQUENCE: 31
atgtccaagg cctctgctct cctcgctggc ctgacgggcg cggccctcgt cgctgcacat      60
ggccacgtca gccacatcgt cgtcaacggc gtctactaca ggaactacga ccccacgaca     120
gactggtacc agcccaaccc gccaacagtc atcggctgga cggcagccga tcaggataat     180
ggcttcgttg aacccaacag ctttggcacg ccagatatca tctgccacaa gagcgccacc     240
cccggcggcg ccacgctac cgttgctgcc ggagacaaga tcaacatcgt ctggaccccc     300
gagtggcccg aatcccacat cggccccgtc attgactacc tagccgcctg caacggtgac     360
tgcgagaccg tcgacaagtc gtcgctgcgc tggttcaaga ttgacggcgc cggctacgac     420
aaggccgccg ccgctgggc cgccgacgct ctgcgcgcca acggcaacag ctggctcgtc     480
cagatcccgt cggatctcaa ggccggcaac tacgtcctcc gccacgagat catcgccctc     540
cacggtgctc agagccccaa cggcgcccag gcctacccgc agtgcatcaa cctccgcgtc     600
accggcggcg gcagcaacct gcccagcggc gtcgccggca cctcgctgta caaggcgacc     660
gacccgggca tcctcttcaa cccctacgtc tcctccccgg attacaccgt ccccggcccg     720
gccctcattg ccggcgccgc cagctcgatc gcccagagca cgtcggtcgc cactgccacc     780
ggcacggcca ccgttcccgg cggcggcggc gccaaccccta ccgccaccac caccgccgcc     840
acctccgccg ccccgagcac caccctgagg acgaccacta cctcggccgc gcagactacc     900
gccccgccct ccggcgatgt gcagaccaag tacggccagt gtggtggcaa cggatggacg     960
ggcccgacgg tgtgcgcccc cggctcgagc tgctccgtcc tcaacgagtg gtactcccag    1020
tgtttgtaa                                                           1029

<210> SEQ ID NO 32
<211> LENGTH: 837
<212> TYPE: DNA
<213> ORGANISM: Myceliophthora thermophila

<400> SEQUENCE: 32 atgtttctc tcaagttctt tatcttggcc ggtgggcttg ctgtcctcac cgaggctcac       60
ataagactag tgtcgcccgc ccctttttacc aaccctgacc agggccccag cccactccta    120
gaggctggca gcgactatcc ctgccacaac ggcaatgggg gcggttatca gggaacgcca    180
acccagatgg caaagggttc taagcagcag ctagccttcc agggggtctgc cgttcatggg    240
ggtggctcct gccaagtgtc catcacctac gacgaaaacc cgaccgctca gagctccttc    300
aaggtcattc actcgattca aggtggctgc cccgccaggg ccgagacgat cccggattgc    360
agcgcacaaa atatcaacgc ctgcaatata aagcccgata tgcccagat ggacacccccg    420
gataagtatg agttcacgat cccggaggat ctccccagtg gcaaggccac cctcgcctgg    480
acatggatca acactatcgg caaccgcgag tttatatgg catgcgcccc ggttgagatc    540
accggcgacg gcggtagcga gtcggctctg gctgcgctgc ccgacatggt cattgccaac    600
atcccgtcca tcggaggaac ctgcgcgacc gaggagggga agtactacga atatcccaac    660
cccggtaagt cggtcgaaac catcccgggc tggaccgatt tggttcccct gcaaggcgaa    720
tgcggtgctg cctccggtgt ctcgggctcc ggcggaaacg ccagcagtgc tacccctgcc    780
```
gcaggggccg ccccgactcc tgctgtccgc ggccgccgtc ccacctggaa cgcctaa    837

<210> SEQ ID NO 33
<211> LENGTH: 672
<212> TYPE: DNA
<213> ORGANISM: Myceliophthora thermophila

<400> SEQUENCE: 33
atgaagctcg ccacgctcct cgccgccctc accctcgggg tggccgacca gctcagcgtc    60
gggtccagaa agtttggcgt gtacgagcac attcgcaaga acacgaacta caactcgccc   120
gttaccgacc tgtcggacac caacctgcgc tgcaacgtcg gcggggggctc gggcaccagc   180 accaccgtgc tcgacgtcaa ggccggagac tcgttcacct tcttcagcga cgttgccgtc   240
taccaccagg ggcccatctc gctgtgcgtg gaccggacca gtgcagagag catggatgga   300
cgggaaccgg acatgcgctg ccgaactggc tcacaagctg gctacctggc ggtgactgac   360
tacgacgggt ccggtgactg tttcaagatc tatgactggg accgacgtt caacggggc    420 caggcgtcgt ggccgacgag gaattcgtac gagtacagca tcctcaagtg catcagggac   480
ggcgaatacc tactgcggat tcagtccctg gccatccata acccaggtgc ccttccgcag   540
ttctacatca gctgcgccca ggtgaatgtg acgggcggag gcaccgtcac cccgagatca   600
aggcgaccga tcctgatcta tttcaacttc cactcgtata tcgtccctgg ccggcagtg    660 ttcaagtgct ag                                                       672

<210> SEQ ID NO 34
<211> LENGTH: 579
<212> TYPE: DNA
<213> ORGANISM: Myceliophthora thermophila

<400> SEQUENCE: 34
atgaccaaga atgcgcagag caagcagggc gttgagaacc caacaagcgg cgacatccgc    60
tgctacacct cgcagacggc ggccaacgtc gtgaccgtgc cggccggctc gaccattcac   120
tacatctcga cccagcagat caaccacccc ggcccgactc agtactacct ggccaaggta   180
ccccccggct cgtcggccaa gaccttttgac gggtccggcg ccgtctggtt caagatctcg   240
accacgatgc ctaccgtgga cagcaacaag cagatgttct ggccagggca gaacacttat   300
gagacctcaa acaccaccat tcccgccaac accccgacg gcgagtacct ccttcgcgtc   360
aagcagatcg ccctccacat ggcgtctcag cccaacaagg tccagttcta cctcgcctgc   420
acccagatca agatcaccgg tggtcgcaac ggcaccccca gcccgctggt cgcgctgccc   480
ggagcctaca agagcaccga ccccggcatc ctggtcgaca tctactccat gaagcccgaa   540
tcgtaccagc ctcccgggcc gcccgtctgg cgcggctaa                          579

<210> SEQ ID NO 35
<211> LENGTH: 852
<212> TYPE: DNA
<213> ORGANISM: Myceliophthora thermophila

<400> SEQUENCE: 35
atgaagccct ttagcctcgt cgccctggcg actgccgtga cggccatgc catcttccag    60 cgggtgtcgg tcaacgggca ggaccagggc cagctcaagg gggtgcgggc ccgtcgagc   120 aactccccga tccagaacgt caacgatgcc aacatggcct gcaacgccaa cattgtgtac   180
cacgacaaca ccatcatcaa ggtgcccgcg ggagcccgcg tcggcgcgtg gtggcagcac   240
gtcatcggcg ggccgcaggg cgccaacgac ccggacaacc cgatcgccgc ctcccacaag   300

```
ggccccatcc aggtctacct ggccaaggtg gacaacgcgg cgacggcgtc gccgtcgggc    360
ctcaagtggt tcaaggtggc cgagcgcggc ctgaacaacg gcgtgtgggc ctacctgatg    420
cgcgtcgagc tgctcgccct gcacagcgcc tcgagccccg cggcgcccca gttctacatg    480
ggctgtgcac agatcgaagt cactggctcc ggcaccaact cgggctccga ctttgtctcg    540
ttccccggcg cctactcggc caacgacccg ggcatcttgc tgagcatcta cgacagctcg    600
ggcaagccca caatggcgg cgctcgtac ccgatccccg cccgcgccc catctcctgc     660 tccggcagcg gcggcggcgg caacaacggc ggcgacggcg gcgacgacaa caacggtggt    720
ggcaacaaca acgcggcgg cagcgtcccc ctgtacgggc agtgcggcgg catcggctac    780
acgggcccga ccacctgtgc ccagggaact tgcaaggtgt cgaacgaata ctacagccag    840
tgcctcccct ag                                                        852

<210> SEQ ID NO 36
<211> LENGTH: 639
<212> TYPE: DNA
<213> ORGANISM: Myceliophthora thermophila

<400> SEQUENCE: 36
atgaagctca cctcgtccct cgctgtcctg ccgctgccg cgcccaggc tcactatacc      60 ttccctaggg ccggcactgg tggttcgctc tctggcgagt gggaggtggt ccgcatgacc    120
gagaaccatt actcgcacgg cccggtcacc gatgtcacca gccccgagat gacctgctat    180
cagtccggcg tgcagggtgc gccccagacc gtccaggtca aggcgggctc ccaattcacc    240
ttcagcgtgg atccctccat cggccacccc ggccctctcc agttctacat ggctaaggtg    300
ccgtcgggcc agacgccgc caccttttgac ggcacgggag ccgtgtggtt caagatctac    360
caagacggcc cgaacggcct cggcaccgac agcattacct ggcccagcgc cggcaaaacc    420
gaggtctcgg tcaccatccc cagctgcatc gaggatggcg agtacctgct ccgggtcgag    480 cacaccccc tccctacagc gccagcagcg caaaaccgag ctcgctcgtc accatcccca    540
gctgcataca aggccaccga cccgggcatc ctcttccagc tctactggcc catcccgacc    600
gagtacatca ccccggcccc ggcccccgtc tcttgctaa                           639

<210> SEQ ID NO 37
<211> LENGTH: 447
<212> TYPE: DNA
<213> ORGANISM: Myceliophthora thermophila

<400> SEQUENCE: 37
atgccgccac cacgactgag caccctcctt ccctcctag ccttaatagc ccccaccgcc      60
ctggggcact cccacctcgg gtacatcatc atcaacggcg aggtatacca aggattcgac    120
ccgcggccgg agcaggcgaa ctcgccgttg cgcgtgggct ggtcgacggg ggcaatcgac    180
gacgggttcg tggcgccggc caactactcg tcgcccgaca tcatctgcca catcgagggg    240
gccagcccgc cggcgcacgc gcccgtccgg gcgggcgacc gggtgcacgt gcaatggaac    300
ggctggccgc tcggacacgt ggggccggtg ctgtcgtacc tggcgccctg cggcgggctg    360 gagggtccg agagcgggtg cgccggggtg gacaagcggc agctgcggtg gaccaaggtg    420
gacgactcgc tgccggcgat ggagctg                                        447

<210> SEQ ID NO 38
<211> LENGTH: 453
<212> TYPE: DNA
```

<213> ORGANISM: Myceliophthora thermophila

<400> SEQUENCE: 38

| | | | | | |
|---|---|---|---|---|---|
| atgaggtcga | cattggccgg | tgccctggca | gccatcgctg | ctcagaaagt | agccggccac | 60 |
| gccacgtttc | agcagctctg | gcacggctcc | tcctgtgtcc | gccttccggc | tagcaactca | 120 |
| cccgtcacca | atgtgggaag | cagagacttc | gtctgcaacg | ctggcacccg | ccccgtcagt | 180 |
| ggcaagtgcc | ccgtgaaggc | tggcggcacc | gtcaccatcg | agatgcacca | gcaacccggc | 240 |
| gaccgcagct | gcaacaacga | agccatcgga | ggggcgcatt | ggggccccgt | ccaggtgtac | 300 |
| ctgaccaagg | ttcaggacgc | cgcgacggcc | gacggctcga | cgggctggtt | caagatcttc | 360 |
| tccgactcgt | ggtccaagaa | gcccgggggc | aacttgggcg | acgacgacaa | ctggggcacg | 420 |
| cgcgacctga | acgcctgctg | cgggaagatg | gac | | | 453 |

<210> SEQ ID NO 39
<211> LENGTH: 738
<212> TYPE: DNA
<213> ORGANISM: Myceliophthora thermophila

<400> SEQUENCE: 39

| | | | | | |
|---|---|---|---|---|---|
| atgctcctcc | tcaccctagc | cacactcgtc | accctcctgg | cgcgccacgt | ctcggctcac | 60 |
| gcccggctgt | tccgcgtctc | tgtcgacggg | aaagaccagg | gcgacgggct | gaacaagtac | 120 |
| atccgctcgc | cggcgaccaa | cgaccccgtg | cgcgacctct | cgagccgcgc | catcgtgtgc | 180 |
| aacacccagg | ggtccaaggc | cgccccggac | ttcgtcaggg | ccgcggccgg | cgacaagctg | 240 |
| accttcctct | gggcgcacga | caacccggac | gacccggtcg | actacgtcct | cgacccgtcc | 300 |
| cacaagggcg | ccatcctgac | ctacgtcgcc | gcctacccct | ccggggaccc | gaccggcccc | 360 |
| atctggagca | agcttgccga | ggaaggattc | accggcgggc | agtgggcgac | catcaagatg | 420 |
| atcgacaacg | gcggcaaggt | cgacgtgacg | ctgcccgagg | cccttgcgcc | gggaaagtac | 480 |
| ctgatccgcc | aggagctgct | ggccctgcac | cgggccgact | tgcctgcga | cgacccggcc | 540 |
| caccccaacc | gcggcgccga | gtcgtacccc | aactgcgtcc | aggtggaggt | gtcgggcagc | 600 |
| ggcgacaaga | agccggacca | gaactttgac | ttcaacaagg | gctatacctg | cgataacaaa | 660 |
| ggactccact | ttaagatcta | catcggtcag | gacagccagt | atgtggcccc | ggggccgcgg | 720 |
| ccttggaatg | ggagctga | | | | | 738 |

<210> SEQ ID NO 40
<211> LENGTH: 600
<212> TYPE: DNA
<213> ORGANISM: Myceliophthora thermophila

<400> SEQUENCE: 40

| | | | | | |
|---|---|---|---|---|---|
| atgttcactt | cgctttgcat | cacagatcat | tggaggactc | ttagcagcca | ctctgggcca | 60 |
| gtcatgaact | atctcgccca | ttgcaccaat | gacgactgca | agtctttcaa | gggcgacagc | 120 |
| ggcaacgtct | gggtcaagat | cgagcagctc | gcgtacaacc | cgtcagccaa | ccccccctgg | 180 |
| gcgtctgacc | tcctccgtga | gcacggtgcc | aagtggaagg | tgacgatccc | gccagtctt | 240 |
| gtccccggcg | aatatctgct | gcggcacgag | atcctggggt | tgcacgtcgc | aggaaccgtg | 300 |
| atgggcgccc | agttctaccc | cggctgcacc | cagatcaggg | tcaccgaagg | cgggagcacg | 360 |
| cagctgccct | cgggtattgc | gctcccaggc | gcttacggcc | acaagacga | gggtatcttg | 420 |
| gtcgacttgt | ggagggttaa | ccagggccag | gtcaactaca | cggcgcctgg | aggacccgtt | 480 |
| tggagcgaag | cgtgggacac | cgagtttggc | gggtccaaca | cgaccgagtg | cgccaccatg | 540 |

```
ctcgacgacc tgctcgacta catggcggcc aacgacgagt ggatcggctg acggcctag    600
```

<210> SEQ ID NO 41
<211> LENGTH: 684
<212> TYPE: DNA
<213> ORGANISM: Myceliophthora thermophila

<400> SEQUENCE: 41

```
atgaagctga gcgctgccat cgccgtgctc gcggccgccc ttgccgaggg gcactatacc     60
ttccccagca tcgccaacac ggccgactgg caatatgtgc gcatcacgac caacttccag    120
agcaacggcc ccgtgacgga cgtcaactcg accagatccg gtgctacga gcgcaacccg     180
ggcaccggcg cccccggcat ctacaacgtc acggccggca aaccatcaa ctacaacgcc    240
aagtcgtcca tctcccaccc gggacccatg gccttctaca ttgccaaggt tcccgccggc    300
cagtcggccg ccacctggga cggtaagggc gccgtctggt ccaagatcca ccaggagatg    360
ccgcactttg gcaccagcct cacctgggac tccaacggcc gcacctccat gcccgtcacc    420
atccccgct gtctgcagga cggcgagtat ctgctgcgtg cagagcacat tgccctccac    480
agcgccggca gccccggcgg cgcccagttc tacatttctt gtgcccagct ctcagtcacc    540
ggcggcagcg ggacctggaa ccccaggaac aaggtgtcgt tccccggcgc ctacaaggcc    600
actgacccgg gcatcctgat caacatctac taccccgtcc cgactagcta cactcccgct    660
ggtcccccg tcgacacctg ctaa                                            684
```

<210> SEQ ID NO 42
<211> LENGTH: 768
<212> TYPE: DNA
<213> ORGANISM: Myceliophthora thermophila

<400> SEQUENCE: 42

```
atgtaccgca cgctcggttc cattgccctg ctcgcggggg gcgctgccgc ccacggcgcc     60
gtgaccagct acaacattgc gggcaaggac taccctggat actcgggctt cgcccctacc    120
ggccaggatg tcatccagtg gcaatggccc gactataacc ccgtgctgtc cgccagcgac    180
cccaagctcc gctgcaacgg cggcaccggg gcggcgctgt atgccgaggc ggcccccggc    240
gacaccatca cggccacctg ggcccagtgg acgcactccc agggcccgat cctggtgtgg    300
atgtacaagt gccccggcga cttcagctcc tgcgacggcc ccggcgcggg ttggttcaag    360
atcgacgagg ccggcttcca cggcgacggc acgaccgtct tcctcgacac cgagaccccc    420
tcgggctggg acattgccaa gctggtcggc ggcaacaagt cgtggagcag caagatccct    480
gacggcctcg ccccgggcaa ttacctggtc cgccacgagc tcatcgccct gcaccaggcc    540
aacaacccgc aattctaccc cgagtgcgcc cagatcaagg tcaccggctc tggcaccgcc    600
gagcccgccg cctcctacaa ggccgccatc cccggctact gccagcagag cgaccccaac    660
atttcgttca acatcaacga ccactcccctc ccgcaggagt acaagatccc cggtcccccg    720
gtcttcaagg gcaccgcctc cgccaaggct cgcgcttttcc aggcctaa                768
```

<210> SEQ ID NO 43
<211> LENGTH: 678
<212> TYPE: DNA
<213> ORGANISM: Myceliophthora thermophila

<400> SEQUENCE: 43

```
atgctgacaa caaccttcgc cctcctgacg gccgctctcg gcgtcagcgc ccattatacc     60
```

-continued

```
ctccccaggg tcgggaccgg ttccgactgg cagcacgtgc ggcgggctga caactggcaa    120
aacaacggct tcgtcggcga cgtcaactcg gagcagatca ggtgcttcca ggcgacccct    180
gccggcgccc aagacgtcta cactgttcag gcgggatcga ccgtgaccta ccacgccaac    240
cccagtatct accaccccgg ccccatgcag ttctacctgg cccgcgttcc ggacggacag    300
gacgtcaagt cgtggaccgg cgagggtgcc gtgtggttca aggtgtacga ggagcagcct    360
caatttggcg cccagctgac ctggcctagc aacggcaaga gctcgttcga ggttcctatc    420
cccagctgca ttcgggcggg caactacctc ctccgcgctg agcacatcgc cctgcacgtt    480
gcccaaagcc agggcggcgc ccagttctac atctcgtgcg cccagctcca ggtcactggt    540
ggcggcagca ccgagccttc tcagaaggtt tccttcccgg gtgcctacaa gtccaccgac    600
cccggcattc ttatcaacat caactacccc gtccctacct cgtaccagaa tccgggtccg    660
gctgtcttcc gttgctaa                                                  678
```

<210> SEQ ID NO 44
<211> LENGTH: 714
<212> TYPE: DNA
<213> ORGANISM: Myceliophthora thermophila

<400> SEQUENCE: 44

```
atgaaggttc tcgcgcccct gattctggcc ggtgccgcca cgcccacac catcttctca     60 tccctcgagg tgggcggcgt caaccagggc atcgggcagg tgtccgcgt gccgtcgtac    120 aacggtccga tcgaggacgt gacgtccaac tcgatcgcct gcaacgggcc ccccaacccg    180
acgacgccga ccaacaaggt catcacggtc cgggccggcg agacggtgac ggccgtctgg    240
cggtacatgc tgagcaccac cggctcggcc ccaacgaca tcatggacag cagccacaag    300
ggcccgacca tggcctacct caagaaggtc gacaacgcca ccaccgactc gggcgtcggc    360
ggcggctggt tcaagatcca ggaggacggc cttaccaacg gcgtctgggg caccgagcgc    420
gtcatcaacg gccagggccg ccacaacatc aagatccccg agtgcatcgc ccccggccag    480 taccctcctcc gcgccgagat gcttgccctg cacggagctt ccaactaccc cggcgctcag    540
ttctacatgg agtgcgccca gctcaatatc gtcggcggca ccggcagcaa gacgccgtcc    600
accgtcagct cccgggcgc ttacaagggt accgaccccg gagtcaagat caacatctac    660
tggccccccg tcaccagcta ccagattccc ggccccggcg tgttcacctg ctaa          714
```

<210> SEQ ID NO 45
<211> LENGTH: 741
<212> TYPE: DNA
<213> ORGANISM: Myceliophthora thermophila

<400> SEQUENCE: 45

```
atgaagctct ccctcttttc cgtcctggcc actgccctca ccgtcgaggg gcatgccatc     60
ttccagaagg tctccgtcaa cggagcggac cagggctccc tcaccggcct ccgcgctccc    120
aacaacaaca ccccgtgca gaatgtcaac agccaggaca tgatctgcgg ccagtcggga    180
tcgacgtcga acactatcat cgaggtcaag gccggcgata ggatcggtgc ctggtatcag    240
catgtcatcg gcggtgccca gttccccaac gacccagaca cccgattgc caagtcgcac    300 aagggccccg tcatggccta cctcgccaag gttgacaatg ccgcaaccgc cagcaagacg    360
ggcctgaagt ggttcaagat ttgggaggat acctttaatc ccagcaccaa gacctggggt    420
gtcgacaacc tcatcaacaa caacggctgg gtgtacttca acctcccgca gtgcatcgcc    480
gacggcaact acctcctccg cgtcgaggtc ctcgctctgc actcggccta ctcccagggc    540
```

```
caggctcagt tctaccagtc ctgcgcccag atcaacgtat ccggcggcgg ctccttcacg      600
ccggcgtcga ctgtcagctt cccgggtgcc tacagcgcca gcgaccccgg tatcctgatc      660
aacatctacg gcgccaccgg ccagcccgac aacaacggcc agccgtacac tgcccctggg      720
cccgcgccca tctcctgctg a                                                741

<210> SEQ ID NO 46
<211> LENGTH: 765
<212> TYPE: DNA
<213> ORGANISM: Myceliophthora thermophila

<400> SEQUENCE: 46
atggccctcc agctcttggc gagcttggcc ctcctctcag tgccggccct tgcccacggt       60
ggcttggcca actacaccgt cggtgatact tggtacagag gctacgaccc aaacctgccg      120
ccggagacgc agctcaacca gacctggatg atccagcggc aatgggccac catcgacccc      180
gtcttcaccg tgtcggagcc gtacctggcc tgcaacaacc cgggcgcgcc gccgccctcg      240
tacatcccca tccgcgccgg tgacaagatc acggccgtgt actggtactg gctgcacgcc      300
atcgggccca tgagcgtctg gctcgcgcgg tgcggcgaca cgcccgcggc cgactgccgc      360
gacgtcgacg tcaaccgggt cggctggttc aagatctggg agggcggcct gctggagggt      420
cccaacctgg ccgaggggct ctggtaccaa aaggacttcc agcgctggga cggctccccg      480
tccctctggc ccgtcacgat ccccaagggg ctcaagagcg gacctacat catccggcac       540 gagatcctgt cgcttcacgt cgccctcaag ccccagttt accgagtg tgcgcatctg        600 aatattactg ggggcggaga cttgctgcca cccgaagaga ctctggtgcg gtttccgggg      660 gttcaacaaag aggacgatcc ctctatcttc atcgatgtct actcggagga gaacgcgaac      720
cggacagatt atacggttcc gggagggcca atctgggaag ggtga                      765

<210> SEQ ID NO 47
<211> LENGTH: 708
<212> TYPE: DNA
<213> ORGANISM: Myceliophthora thermophila

<400> SEQUENCE: 47
atgaaggccc tctctctcct tgcggctgcc ggggcagtct ctgcgcatac catcttcgtc       60
cagctcgaag cagacggcac gaggtacccg gtttcgtacg ggatccggga cccaacctac      120
gacggcccca tcaccgacgt cacatccaac gacgttgctt gcaacggcgg tccgaacccg      180 acgacccct ccagcgacgt catcaccgtc accgcgggca ccaccgtcaa ggccatctgg      240
aggcacaccc tccaatccgg cccggacgat gtcatggacg ccagccacaa gggcccgacc      300
ctggcctaca tcaagaaggt cggcgatgcc accaaggact cgggcgtcgg cggtggctgg      360
ttcaagatcc aggaggacgg ttacaacaac ggccagtggg gcaccagcac cgttatctcc      420
aacggcggcg agcactacat tgacatcccg gcctgcatcc ccgagggtca gtacctcctc      480
cgcgccgaga tgatcgccct ccacgcggcc gggtcccccg gcggcgctca gctctacatg      540
gaatgtgccc agatcaacat cgtcggcggc tccggctcgg tgcccagctc gacggtcagc      600
ttccccggcg cgtatagccc caacgacccg ggtctcctca tcaacatcta ttccatgtcg      660
ccctcgagct cgtacaccat cccgggcccg ccgttttca agtgctag                    708

<210> SEQ ID NO 48
<211> LENGTH: 915
<212> TYPE: DNA
```

<213> ORGANISM: Myceliophthora thermophila

<400> SEQUENCE: 48

```
atgaagtcgt ctaccccggc cttgttcgcc gctgggctcc ttgctcagca tgctgcggcc      60
cactccatct tccagcaggc gagcagcggc tcgaccgact tgatacgct gtgcacccgg      120
atgccgccca acaatagccc cgtcactagt gtgaccagcg gcgacatgac ctgcaaagtc     180
ggcggcacca agggggtgtc cggcttctgc gaggtgaacg ccggcgacga gttcacggtt     240
gagatgcacg cgcagcccgg cgaccgctcg tgcgccaacg aggccatcgg cgggaaccac     300
ttcggcccgg tcctcatcta catgagcaag gtcgacgacg cctccaccgc cgacgggtcc     360
ggcgactggt tcaaggtgga cgagttcggc tacgacgcaa gcaccaagac ctggggcacc     420
gacaagctca cgagaactg cggcaagcgc accttcaaca tccccagcca catccccgcg      480
ggcgactatc tcgtccgggc cgaggctatc gcgctacaca ctgccaacca gccaggcggc     540
gcgcagttct acatgagctg ctatcaagtc aggatttccg gcggcgaagg gggccagctg     600
cctgccggag tcaagatccc gggcgcgtac agtgccaaca ccccggcat ccttgtcgac      660
atctggggta acgatttcaa cgaccctcca ggacactcgg cccgtcacgc catcatcatc     720
atcagcagca gcagcaacaa cagcggcgcc aagatgacca gaagatcca ggagcccacc     780
atcacatcgg tcacggacct cccaccgac gaggccaagt ggatcgcgct ccaaaagatc      840
tcgtacgtgg accagacggg cacggcgcgg acatacgagc cggcgtcgcg caagacgcgg    900
tcgccaagag tctag                                                      915
```

<210> SEQ ID NO 49
<211> LENGTH: 972
<212> TYPE: DNA
<213> ORGANISM: Myceliophthora thermophila

<400> SEQUENCE: 49

```
atgaagtcct tcaccctcac cactctggcc gccctggctg caacgccgc cgctcacgcg       60
accttccagg ccctctgggt cgacggcgtc gactacggcg cgcagtgtgc ccgtctgccc     120
gcgtccaact cgccggtcac cgacgtgacc tccaacgcga tccgctgcaa cgccaacccc     180
tcgcccgctc ggggcaagtg cccggtcaag gccggctcga ccgttacggt cgagatgcat    240
cagcaacccg tgaccgctc gtgcagcagc gaggcgatcg gcggggcgca ctacggcccc     300
gtgatggtgt acatgtccaa ggtgtcggac gcggcgtcgg cggacgggtc gtcgggctgg    360
ttcaaggtgt cgaggacgg ctgggccaag aacccgtccg gcgggtcggg cgacgacgac      420
tactggggca ccaaggacct gaactcgtgc tgcgggaaga tgaacgtcaa gatccccgcc    480
gacctgccct cggcgactc ctgctccggg gccgaggccc tcgcgctgca cacggccggc     540
agcgcgggcg gcgcccagtt ctacatgacc tgctaccagc tcaccgtgac cggctccggc    600
agcgccagcc cgcccaccgt ctccttcccg ggcgcctaca aggccaccga cccgggcatc    660
ctcgtcaaca tccacgcccc gctgtccggc tacaccgtgc ccggcccggc cgtctactcg    720
ggcggctcca ccaagaaggc cggcagcgcc tgcaccggct gcgagtccac ttgcgccgtc    780
ggctccggcc ccaccgccac cgtctcccag tcgcccggtt ccaccgccac ctcggccccc    840
ggcggcggcg gcggctgcac cgtccagaag taccagcagt gcggcggcca gggctacacc    900
ggctgcacca actgcgcgtc cggctccacc tgcagcgcgg tctcgccgcc ctactactcg    960
cagtgcgtct aa                                                          972
```

<210> SEQ ID NO 50
<211> LENGTH: 870
<212> TYPE: DNA
<213> ORGANISM: Myceliophthora thermophila

<400> SEQUENCE: 50

| | | | | | |
|---|---|---|---|---|---|
| atgaagggac | tcctcggcgc | cgccgccctc | tcgctggccg | tcagcgatgt | ctcggcccac | 60 |
| tacatctttc | agcagctgac | gacgggcggc | gtcaagcacg | ctgtgtacca | gtacatccgc | 120 |
| aagaacacca | actataactc | gcccgtgacc | gatctgacgt | ccaacgacct | ccgctgcaat | 180 |
| gtgggtgcta | ccggtgcggg | caccgatacc | gtcacggtgc | gcgccggcga | ttcgttcacc | 240 |
| ttcacgaccg | atacgcccgt | ttaccaccag | ggcccgacct | cgatctacat | gtccaaggcc | 300 |
| cccggcagcg | cgtccgacta | cgacggcagc | ggcggctggt | tcaagatcaa | ggactgggct | 360 |
| gactacaccg | ccacgattcc | ggaatgtatt | ccccccggcg | actacctgct | cgcatccag | 420 |
| caactcggca | tccacaaccc | ttggcccgcg | ggcatccccc | agttctacat | ctcttgtgcc | 480 |
| cagatcaccg | tgactggtgg | cggcagtgcc | aaccccggcc | cgaccgtctc | catcccaggc | 540 |
| gccttcaagg | agaccgaccc | gggctacact | gtcaacatct | acaacaactt | ccacaactac | 600 |
| accgtccctg | gccagccgt | cttcacctgc | aacggtagcg | cggcaacaa | cggcggcggc | 660 |
| tccaacccag | tcaccaccac | caccaccacc | accaccaggc | cgtccaccag | caccgcccag | 720 |
| tcccagccgt | cgtcgagccc | gaccagcccc | tccagctgca | ccgtcgcgaa | gtggggccag | 780 |
| tgcggaggac | agggttacag | cggctgcacc | gtgtgcgcgg | ccgggtcgac | ctgccagaag | 840 |
| accaacgact | actacagcca | gtgcttgtag | | | | 870 |

<210> SEQ ID NO 51
<211> LENGTH: 1041
<212> TYPE: DNA
<213> ORGANISM: Myceliophthora thermophila

<400> SEQUENCE: 51

| | | | | | |
|---|---|---|---|---|---|
| atgtcttcct | tcacctccaa | gggtctcctt | tccgccctca | tgggcgcggc | aacggttgcc | 60 |
| gcccacggtc | acgtcaccaa | catcgtcatc | aacggcgtct | cataccagaa | cttcgaccca | 120 |
| ttcacgcacc | cttatatgca | gaaccctccg | acggttgtcg | gctggaccgc | gagcaacacg | 180 |
| gacaacggct | tcgtcggccc | cgagtccttc | tctagcccgg | acatcatctg | ccacaagtcc | 240 |
| gccaccaacg | ctggcggcca | tgccgtcgtc | gcggccggcg | ataaggtctt | catccagtgg | 300 |
| gacacctggc | ccgagtcgca | ccacggtccg | gtcatcgact | atctcgccga | ctgcggcgac | 360 |
| gcgggctgcg | agaaggtcga | caagaccacg | ctcaagttct | tcaagatcag | cgagtccggc | 420 |
| ctgctcgacg | gcactaacgc | ccccggcaag | tgggcgtccg | acacgctgat | cgccaacaac | 480 |
| aactcgtggc | tggtccagat | cccgcccaac | atcgcccgg | caactacgt | cctgcgccac | 540 |
| gagatcatcg | ccctgcacag | cgccggccag | cagaacggcg | cccagaacta | ccctcagtgc | 600 |
| ttcaacctgc | aggtcaccgg | ctccggcact | cagaagcccc | cggcgtcct | cggcaccgag | 660 |
| ctctacaagg | ccaccgacgc | cggcatcctg | ccaacatct | acacctcgcc | cgtcacctac | 720 |
| cagatccccg | gccggccat | catctcgggc | gcctccgccg | tccagcagac | cacctcggcc | 780 |
| atcaccgcct | ctgctagcgc | catcaccggc | tccgctaccg | ccgcgcccac | ggctgccacc | 840 |
| accaccgccg | ccgccgccgc | caccactacc | accaccgctg | gctccggtgc | taccgccacg | 900 |
| ccctcgaccg | gcggctctcc | ttcttccgcc | cagcctgctc | ctaccaccgc | tgccgctacc | 960 |
| tccagccctg | ctcgcccgac | ccgctgcgct | ggtctgaaga | agcgccgtcg | ccacgcccgt | 1020 |

```
gacgtcaagg ttgccctcta a                                          1041
```

<210> SEQ ID NO 52
<211> LENGTH: 714
<212> TYPE: DNA
<213> ORGANISM: Myceliophthora thermophila

<400> SEQUENCE: 52

```
atgaagacgc tcgccgccct cgtggtctcg gccgccctcg tggccgcgca cggctatgtt    60
gaccacgcca cgatcggtgg caaggattat cagttctacc agccgtacca ggacccttac   120
atgggcgaca caagcccga tagggtttcc cgctccatcc cgggcaacgg ccccgtggag   180
gacgtcaact ccatcgacct ccagtgccac gccggtgccg aaccggccaa gctccacgcc   240
cccgccgccg ccggctcgac cgtgacgctc tactggaccc ctggcccga ctcccacgtc   300
ggccccgtca tcacctacat ggctcgctgc cccgacaccg gctgccagga ctggtccccg   360
ggaactaagc ccgtttggtt caagatcaag aaggcggcc gtgagggcac ctccaatacc   420
ccgctcatga cggccccctc cgcctacacc tacacgatcc cgtcctgcct caagagcggc   480
tactacctcg tccgccacga gatcatcgcc ctgcactcgg cctggcagta ccccggcgcc   540
cagttctacc cgggctgcca ccagctccag gtcaccggcg cggctccac cgtgccctct   600
accaacctgg tctccttccc cggcgcctac aaggggagcg accccggcat cacctacgac   660
gcttacaagg cgcaaccta caccatccct ggcccggccg tgtttacctg ctga          714
```

<210> SEQ ID NO 53
<211> LENGTH: 678
<212> TYPE: DNA
<213> ORGANISM: Myceliophthora thermophila

<400> SEQUENCE: 53

```
atgagatact cctccagct cgctgcggcc gcggcctttg ccgtgaacag cgcggcgggt    60
cactacatct ccagcagtt cgcgacgggc gggtccaagt acccgccctg gaagtacatc   120
cggcgcaaca ccaacccgga ctggctgcag aacgggccgg tgacggacct gtcgtcgacc   180
gacctgcgct gcaacgtggg cggcaggtc agcaacggga ccgagaccat cacccttgaac   240
gccggcgacg agttcagctt catcctcgac acgccgtct accatgccgg ccccacctcg   300
ctctacatgt ccaaggcgcc cggagctgtg ccgactacg acggcggcgg ggcctggttc   360
aagatctacg actggggtcc gtcggggacg agctggacgt tgagtggcac gtacactcag   420
agaattccca gtgcatccc tgacggcgag tacctcctcc gcatccagca gatcgggctc   480
cacaaccccg gcgccgcgcc acagttctac atcagctgcg ctcaagtcaa ggtcgtcgat   540
ggcggcagca ccaatccgac cccgaccgcc cagattccgg gagccttcca cagcaacgac   600
cctggcttga ctgtcaatat ctacaacgac cctctcacca actacgtcgt cccgggacct   660
agagtttcgc actggtag                                                678
```

<210> SEQ ID NO 54
<211> LENGTH: 1335
<212> TYPE: DNA
<213> ORGANISM: Myceliophthora thermophila

<400> SEQUENCE: 54

```
atgcacccct cccttctttt cacgcttggg ctggcgagcg tgcttgtccc cctctcgtct    60
gcacacacta ccttcacgac cctcttcgtc aacgatgtca accaaggtga tggtacctgc   120
attcgcatgg cgaagaaggg caatgtcgcc acccatcctc tcgcaggcgg tctcgactcc   180
```

```
gaagacatgg cctgtggtcg ggatggtcaa gaacccgtgg catttacgtg tccggcccca    240
gctggtgcca agttgactct cgagtttcgc atgtgggccg atgcttcgca gtccggatcg    300
atcgatccat cccaccttgg cgtcatggcc atctacctca agaaggtttc gacatgaaa    360 tctgacgcgg ccgctggccc gggctggttc aagatttggg accaaggcta cgacttggcg    420
gccaagaagt gggccaccga gaagctcatc gacaacaacg gcctcctgag cgtcaacctt    480
ccaaccggct taccaaccgg ctactacctc gcccgccagg agatcatcac gctccaaaac    540
gttaccaatg acaggccaga gccccagttc tacgtcggct gcgcacagct ctacgtcgag    600
ggcacctcgg actcacccat ccctcggac aagacggtct ccattccgg ccacatcagc    660 gacccggccg acccgggcct gaccttcaac gtctacacgg gcgacgcatc cacctacaag    720
ccgcccggcc ccgaggttta cttccccacc accaccacca ccacctcctc ctcctcctcc    780
ggaagcagcg acaacaaggg agccaggcgc cagcaaaccc ccgacgacaa gcaggccgac    840
ggcctcgttc cagccgactg cctcgtcaag aacgcgaact ggtgcgccgc tgccctgccg    900
ccgtacaccg acgaggccgg ctgctgggcc gccgccgagg actgcaacaa gcagctggac    960
gcgtgctaca ccagcgcacc cccctcgggc agcaaggggt gcaaggtctg ggaggagcag   1020
gtgtgcaccg tcgtctcgca gaagtgcgag gccggggatt tcaaggggcc ccgcagctc   1080 gggaaggagc tcggcgaggg gatcgatgag cctattccgg ggggaaagct gccccggcg   1140 gtcaacgcgg gagagaacgg gaatcatggc ggaggtggtg gtgatgatgg tgatgatgat   1200
aatgatgagg ccggggctgg ggcagcgtcg actccgactt ttgctgctcc tggtgcggcc   1260
aagactcccc aaccaaactc cgagagggcc cggcgccgtg aggcgcattg gcggcgactg   1320
gaatctgctg agtag                                                    1335

<210> SEQ ID NO 55
<211> LENGTH: 696
<212> TYPE: DNA
<213> ORGANISM: Myceliophthora thermophila

<400> SEQUENCE: 55
atgaagctca cctcgtccct cgctgtcctg gccgctgccg gcgcccaggc tcactatacc     60
ttccctaggg ccggcactgg tggttcgctc tctggcgagt gggaggtggt ccgcatgacc    120
gagaaccatt actcgcacgg cccggtcacc gatgtcacca gccccgagat gacctgctat    180
cagtccggcg tgcagggtgc gccccagacc gtccaggtca aggcgggctc ccaattcacc    240
ttcagcgtgg atccctccat cggccacccc ggccctctcc agttctacat ggctaaggtg    300
ccgtcgggcc agacggccgc cacctttgac ggcacgggag ccgtgtggtt caagatctac    360
caagacggcc cgaacggcct cggcaccgac agcattacct ggcccagcgc cggcaaaacc    420
gaggtctcgg tcaccatccc cagctgcatc gaggatggcg agtacctgct ccgggtcgag    480
cacatcgcgc tccacagcgc cagcagcgtg gcggcgccc agttctacat cgcctgcgcc    540
cagctctccg tcaccggcgg ctccggcacc ctcaacacgg gctcgctcgt ctccctgccc    600
ggcgcctaca aggccaccga cccgggcatc ctcttccagc tctactggcc catcccgacc    660
gagtacatca cccccggccc ggcccccgtc tcttgc                              696

<210> SEQ ID NO 56
<211> LENGTH: 1176
<212> TYPE: DNA
<213> ORGANISM: Myceliophthora thermophila
```

<400> SEQUENCE: 56

```
atgccgccac cacgactgag caccctcctt ccctcctag ccttaatagc ccccaccgcc      60
ctggggcact cccacctcgg gtacatcatc atcaacggcg aggtatacca aggattcgac    120
ccgcggccgg agcaggcgaa ctcgccgttg cgcgtgggct ggtcgacggg ggcaatcgac    180
gacgggttcg tggcgccggc caactactcg tcgcccgaca tcatctgcca catcgagggg    240
gccagcccgc cggcgcacgc gcccgtccgg gcgggcgacc gggtgcacgt gcaatggaaa    300
cggctggccg ctcggacacg tggggccggt gctgtcgtac ctggcgccct gcggcgggct    360
ggaggggtcc gagagcgggt ggacgactcg ctgccggcga tggagctggt cggggccgcg    420
gggggcgcgg ggggcgagga cgacggcagc ggcagcgacg gcagcggcag cggcggcagc    480
ggacgcgtcg gcgtgcccgg gcagcgctgg gccaccgacg tgttgatcgc ggccaacaac    540
agctggcagg tcgagatccc gcgcgggctg cgggacgggc cgtacgtgct cgccacgag    600
atcgtcgcgc tgcactacgc ggccgagccc ggcggcgcgc agaactaccc gctctgcgtc    660
aacctgtggg tcgagggcgg cgacggcagc atggagctgg accacttcga cgccacccag    720
ttctaccggc ccgacgaccc gggcatcctg ctcaacgtga cggccggcct gcgctcatac    780
gccgtgccgg gccgacgct ggccgcgggg gcgacgccgg tgccgtacgc gcagcagaac    840
atcagctcgg cgagggcgga tggaaccccc gtgattgtca ccaggagcac ggagacggtg    900
cccttcaccg cggcacccac gccagccgag acggcagaag ccaaaggggg gaggtatgat    960
gaccaaaccc gaactaaaga cctaaatgaa cgcttctttt atagtagccg gccagaacag   1020
aagaggctga cagcgacctc aagaagggaa ctagttgatc atcgtacccg gtacctctcc   1080
gtagctgtct gcgcagattt cggcgctcat aaggcagcag aaaccaacca cgaagctttg   1140
agaggcggca ataagcacca tggcggtgtt tcagag                             1176
```

<210> SEQ ID NO 57
<211> LENGTH: 837
<212> TYPE: DNA
<213> ORGANISM: Myceliophthora thermophila

<400> SEQUENCE: 57

```
atgaggtcga cattggccgg tgccctggca gccatcgctg ctcagaaagt agccggccac      60
gccacgtttc agcagctctg gcacggctcc tcctgtgtcc gccttccggc tagcaactca    120
cccgtcacca atgtgggaag cagagacttc gtctgcaacg ctggcacccg ccccgtcagt    180
ggcaagtgcc ccgtgaaggc tggcggcacc gtcaccatcg agatgcacca gcaacccggc    240
gaccgcagct gcaacaacga agccatcgga ggggcgcatt ggggccccgt ccaggtgtac    300
ctgaccaagg ttcaggacgc cgcgacggcc gacggctcga cgggctggtt caagatcttc    360
tccgactcgt ggtccaagaa gcccggggc aactcgggcg acgacgacaa ctggggcacg    420
cgcgacctga cgcctgctg cgggaagatg gacgtggcca tcccggccga catcgcgtcg    480
ggcgactacc tgctgcgggc cgaggcgctg gccctgcaca cggccggaca ggccggcggc    540
gcccagttct acatgagctg ctaccagatg acggtcgagg gcggctccgg gaccgccaac    600
ccgcccaccg tcaagttccc gggcgcctac agcgccaacg acccgggcat cctcgtcaac    660
atccacgccc ccctttccag ctacaccgcg cccggcccgg ccgtctacgc gggcggcacc    720
atccgcgagg ccggctccgc ctgcaccggc tgcgcgcaga cctgcaaggt cgggtcgtcc    780
ccgagcgccg ttgcccccgg cagcggcgcg ggcaacggcg gcgggttcca accccga       837
```

<210> SEQ ID NO 58
<211> LENGTH: 693
<212> TYPE: DNA
<213> ORGANISM: Myceliophthora thermophila

<400> SEQUENCE: 58

```
atgaactatc tcgcccattg caccaatgac gactgcaagt ctttcaaggg cgacagcggc      60
aacgtctggg tcaagatcga gcagctcgcg tacaacccgt cagccaaccc ccctgggcg     120
tctgacctcc tccgtgagca cggtgccaag tggaaggtga cgatcccgcc cagtcttgtc    180
cccggcgaat atctgctgcg gcacgagatc ctggggttgc acgtcgcagg aaccgtgatg    240
ggcgcccagt tctaccccgg ctgcacccag atcagggtca ccgaaggcgg gagcacgcag    300
ctgccctcgg gtattgcgct cccaggcgct tacgcccac aagacgaggg tatcttggtc     360
gacttgtgga gggttaacca gggccaggtc aactacacgg cgcctggagg acccgtttgg    420
agcgaagcgt gggacaccga gtttggcggg tccaacacga ccgagtgcgc caccatgctc    480
gacgacctgc tcgactacat ggcggccaac gacgacccat gctgcaccga ccagaaccag    540
ttcgggagtc tcgagccggg gagcaaggcg gccggcggct cgccgagcct gtacgatacc    600
gtcttggtcc ccgttctcca gaagaaagtg ccgacaaagc tgcagtggag cggaccggcg    660
agcgtcaacg gggatgagtt gacagagagg ccc                                 693
```

<210> SEQ ID NO 59
<211> LENGTH: 726
<212> TYPE: DNA
<213> ORGANISM: Myceliophthora thermophila

<400> SEQUENCE: 59

```
atgaagtcgt ctaccccggc cttgttcgcc gctgggctcc ttgctcagca tgctgcggcc      60
cactccatct tccagcaggc gagcagcggc tcgaccgact tgatacgct gtgcacccgg     120
atgccgccca acaatagccc cgtcactagt gtgaccagcg gcgacatgac ctgcaacgtc    180
ggcggcacca agggggtgtc gggcttctgc gaggtgaacg ccggcgacga gttcacggtt    240
gagatgcacg cgcagcccgg cgaccgctcg tgcgccaacg aggccatcgg cgggaaccac    300
ttcggcccgg tcctcatcta catgagcaag gtcgacacg cctccactgc cgacgggtcc     360
ggcgactggt tcaaggtgga cgagttcggc tacgacgcaa gcaccaagac ctggggcacc    420
gacaagctca cgagaactg cggcaagcgc accttcaaca tccccagcca catccccgcg    480
ggcgactatc tcgtccgggc cgaggctatc gcgctacaca ctgccaacca gccaggcggc    540
gcgcagttct acatgagctg ctatcaagtc aggatttccg gcggcgaagg gggccagctg    600
cctgccggag tcaagatccc gggcgcgtac agtgccaacg accccggcat ccttgtcgac    660
atctggggta cgatttcaa cgagtacgtt attccgggcc cccggtcat cgacagcagc      720
tacttc                                                                726
```

<210> SEQ ID NO 60
<211> LENGTH: 870
<212> TYPE: PRT
<213> ORGANISM: Myceliophthora thermophila

<400> SEQUENCE: 60

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

-continued

```
Ser Glu Pro Phe Tyr Pro Ser Pro Trp Met Asn Pro Asn Ala Asp Gly
         35                  40                  45

Trp Ala Glu Ala Tyr Ala Gln Ala Lys Ser Phe Val Ser Gln Met Thr
 50                  55                  60

Leu Leu Glu Lys Val Asn Leu Thr Thr Gly Val Gly Trp Gly Ala Glu
 65                  70                  75                  80

Gln Cys Val Gly Gln Val Gly Ala Ile Pro Arg Leu Gly Leu Arg Ser
                 85                  90                  95

Leu Cys Met His Asp Ser Pro Leu Gly Ile Arg Gly Ala Asp Tyr Asn
                100                 105                 110

Ser Ala Phe Pro Ser Gly Gln Thr Val Ala Thr Trp Asp Arg Gly
                115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
                180                 185                 190

Val Ile Ala Cys Ala Lys His Phe Ile Gly Asn Glu Gln Glu His Phe
                195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Gln Gln Val Asn Asn Ser Tyr Ala Cys Gln Asn Ser Lys Leu Leu
                260                 265                 270

Asn Asp Leu Leu Lys Asn Glu Leu Gly Phe Gln Gly Phe Val Met Ser
                275                 280                 285

Asp Trp Gln Ala Gln His Thr Gly Ala Ala Ser Ala Val Ala Gly Leu
290                 295                 300

Asp Met Ser Met Pro Gly Asp Thr Gln Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
                340                 345                 350

Val Thr Lys Thr Thr Asp Leu Glu Pro Ile Asn Phe Ser Phe Trp Thr
                355                 360                 365

Asp Asp Thr Tyr Gly Pro Ile His Trp Ala Ala Lys Gln Gly Tyr Gln
370                 375                 380

Glu Ile Asn Ser His Val Asp Val Arg Ala Asp His Gly Asn Leu Ile
385                 390                 395                 400

Arg Glu Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
                420                 425                 430

Gly Ser Ser Pro Asn Gly Pro Asn Gly Cys Ser Asp Arg Gly Cys Asn
                435                 440                 445

Glu Gly Thr Leu Ala Met Gly Trp Gly Ser Gly Thr Ala Asn Tyr Pro
```

```
              450                 455                 460
Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Lys Thr
                    485                 490                 495

Lys Ala Leu Val Ser Gln Ala Asn Ala Thr Ala Ile Val Phe Val Asn
                500                 505                 510

Ala Asp Ser Gly Glu Gly Tyr Ile Asn Val Asp Gly Asn Glu Gly Asp
                515                 520                 525

Arg Lys Asn Leu Thr Leu Trp Asn Asn Gly Asp Thr Leu Val Lys Asn
                530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
                580                 585                 590

Val Leu Tyr Gly Lys Val Asn Pro Ala Ala Arg Ser Pro Phe Thr Trp
                595                 600                 605

Gly Lys Thr Arg Glu Ser Tyr Gly Ala Asp Val Leu Tyr Lys Pro Asn
                610                 615                 620

Asn Gly Asn Gly Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
                660                 665                 670

Val Val Lys Ser Asn Val Ser Glu Tyr Arg Pro Thr Thr Gly Thr Thr
                675                 680                 685

Ala Gln Ala Pro Thr Phe Gly Asn Phe Ser Thr Asp Leu Glu Asp Tyr
                690                 695                 700

Leu Phe Pro Lys Asp Glu Phe Pro Tyr Ile Tyr Gln Tyr Ile Tyr Pro
705                 710                 715                 720

Tyr Leu Asn Thr Thr Asp Pro Arg Arg Ala Ser Ala Asp Pro His Tyr
                725                 730                 735

Gly Gln Thr Ala Glu Glu Phe Leu Pro Pro His Ala Thr Asp Asp Asp
                740                 745                 750

Pro Gln Pro Leu Leu Arg Ser Ser Gly Gly Asn Ser Pro Gly Gly Asn
                755                 760                 765

Arg Gln Leu Tyr Asp Ile Val Tyr Thr Ile Thr Ala Asp Ile Thr Asn
                770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
                820                 825                 830

Arg Asp Leu Ser Asn Trp Asp Val Thr Val Gln Asp Trp Val Ile Ser
                835                 840                 845

Arg Tyr Pro Lys Thr Ala Tyr Val Gly Arg Ser Ser Arg Lys Leu Asp
                850                 855                 860

Leu Lys Ile Glu Leu Pro
865                 870
```

<210> SEQ ID NO 61
<211> LENGTH: 861
<212> TYPE: PRT
<213> ORGANISM: Thermoascus aurantiacus

<400> SEQUENCE: 61

```
Met Arg Leu Gly Trp Leu Glu Leu Ala Val Ala Ala Ala Thr Val
1               5                   10                  15

Ala Ser Ala Lys Asp Asp Leu Ala Tyr Ser Pro Pro Phe Tyr Pro Ser
            20                  25                  30

Pro Trp Met Asp Gly Asn Gly Glu Trp Ala Glu Ala Tyr Arg Arg Ala
        35                  40                  45

Val Asp Phe Val Ser Gln Leu Thr Leu Ala Glu Lys Val Asn Leu Thr
    50                  55                  60

Thr Gly Val Gly Trp Met Gln Glu Lys Cys Val Gly Glu Thr Gly Ser
65                  70                  75                  80

Ile Pro Arg Leu Gly Phe Arg Gly Leu Cys Leu Gln Asp Ser Pro Leu
                85                  90                  95

Gly Val Arg Phe Ala Asp Tyr Val Ser Ala Phe Pro Ala Gly Val Asn
            100                 105                 110

Val Ala Ala Thr Trp Asp Lys Asn Leu Ala Tyr Leu Arg Gly Lys Ala
        115                 120                 125

Met Gly Glu Glu His Arg Gly Lys Gly Val Asp Val Gln Leu Gly Pro
    130                 135                 140

Val Ala Gly Pro Leu Gly Arg His Pro Asp Gly Gly Arg Asn Trp Glu
145                 150                 155                 160

Gly Phe Ser Pro Asp Pro Val Leu Thr Gly Val Leu Met Ala Glu Thr
                165                 170                 175

Ile Lys Gly Ile Gln Asp Ala Gly Val Ile Ala Cys Ala Lys His Phe
                180                 185                 190

Ile Gly Asn Glu Met Glu His Phe Arg Gln Ala Ser Glu Ala Val Gly
            195                 200                 205

Tyr Gly Phe Asp Ile Thr Glu Ser Val Ser Ser Asn Ile Asp Asp Lys
        210                 215                 220

Thr Leu His Glu Leu Tyr Leu Trp Pro Phe Ala Asp Ala Val Arg Ala
225                 230                 235                 240

Gly Val Gly Ser Phe Met Cys Ser Tyr Asn Gln Val Asn Asn Ser Tyr
                245                 250                 255

Ser Cys Ser Asn Ser Tyr Leu Leu Asn Lys Leu Leu Lys Ser Glu Leu
            260                 265                 270

Asp Phe Gln Gly Phe Val Met Ser Asp Trp Gly Ala His His Ser Gly
        275                 280                 285

Val Gly Ala Ala Leu Ala Gly Leu Asp Met Ser Met Pro Gly Asp Thr
    290                 295                 300

Ala Phe Gly Thr Gly Lys Ser Phe Trp Gly Thr Asn Leu Thr Ile Ala
305                 310                 315                 320

Val Leu Asn Gly Thr Val Pro Glu Trp Arg Val Asp Asp Met Ala Val
                325                 330                 335

Arg Ile Met Ala Ala Phe Tyr Lys Val Gly Arg Asp Arg Tyr Gln Val
            340                 345                 350

Pro Val Asn Phe Asp Ser Trp Thr Lys Asp Glu Tyr Gly Tyr Glu His
        355                 360                 365

Ala Leu Val Gly Gln Asn Tyr Val Lys Val Asn Asp Lys Val Asp Val
```

```
                370                 375                 380
Arg Ala Asp His Ala Asp Ile Ile Arg Gln Ile Gly Ser Ala Ser Val
385                 390                 395                 400

Val Leu Leu Lys Asn Asp Gly Gly Leu Pro Leu Thr Gly Tyr Glu Lys
                405                 410                 415

Phe Thr Gly Val Phe Gly Glu Asp Ala Gly Ser Asn Arg Trp Gly Ala
                420                 425                 430

Asp Gly Cys Ser Asp Arg Gly Cys Asp Asn Gly Thr Leu Ala Met Gly
                435                 440                 445

Trp Gly Ser Gly Thr Ala Asp Phe Pro Tyr Leu Val Thr Pro Glu Gln
                450                 455                 460

Ala Ile Gln Asn Glu Ile Leu Ser Lys Gly Lys Gly Leu Val Ser Ala
465                 470                 475                 480

Val Thr Asp Asn Gly Ala Leu Asp Gln Met Glu Gln Val Ala Ser Gln
                485                 490                 495

Ala Ser Val Ser Ile Val Phe Val Asn Ala Asp Ser Gly Glu Gly Tyr
                500                 505                 510

Ile Asn Val Asp Gly Asn Glu Gly Asp Arg Lys Asn Leu Thr Leu Trp
                515                 520                 525

Lys Gly Gly Glu Glu Val Ile Lys Thr Val Ala Ala Asn Cys Asn Asn
530                 535                 540

Thr Ile Val Val Met His Thr Val Gly Pro Val Leu Ile Asp Glu Trp
545                 550                 555                 560

Tyr Asp Asn Pro Asn Val Thr Ala Ile Val Trp Ala Gly Leu Pro Gly
                565                 570                 575

Gln Glu Ser Gly Asn Ser Leu Val Asp Val Leu Tyr Gly Arg Val Ser
                580                 585                 590

Pro Gly Gly Lys Thr Pro Phe Thr Trp Gly Lys Thr Arg Glu Ser Tyr
                595                 600                 605

Gly Ala Pro Leu Leu Thr Lys Pro Asn Asn Gly Lys Gly Ala Pro Gln
                610                 615                 620

Asp Asp Phe Thr Glu Gly Val Phe Ile Asp Tyr Arg Arg Phe Asp Lys
625                 630                 635                 640

Tyr Asn Glu Thr Pro Ile Tyr Glu Phe Gly Phe Gly Leu Ser Tyr Thr
                645                 650                 655

Thr Phe Glu Tyr Ser Asp Ile Tyr Val Gln Pro Leu Asn Ala Arg Pro
                660                 665                 670

Tyr Thr Pro Ala Ser Gly Ser Thr Lys Ala Ala Pro Thr Phe Gly Asn
                675                 680                 685

Ile Ser Thr Asp Tyr Ala Asp Tyr Leu Tyr Pro Glu Asp Ile His Lys
690                 695                 700

Val Pro Leu Tyr Ile Tyr Pro Trp Leu Asn Thr Thr Asp Pro Lys Lys
705                 710                 715                 720

Ser Ser Gly Asp Pro Asp Tyr Gly Met Lys Ala Glu Asp Tyr Ile Pro
                725                 730                 735

Ser Gly Ala Thr Asp Gly Ser Pro Gln Pro Ile Leu Pro Ala Gly Gly
                740                 745                 750

Ala Pro Gly Gly Asn Pro Gly Leu Tyr Asp Glu Met Tyr Arg Val Ser
                755                 760                 765

Ala Ile Ile Thr Asn Thr Gly Asn Val Val Gly Asp Glu Val Pro Gln
                770                 775                 780

Leu Tyr Val Ser Leu Gly Gly Pro Asp Asp Pro Lys Val Val Leu Arg
785                 790                 795                 800
```

```
Asn Phe Asp Arg Ile Thr Leu His Pro Gly Gln Gln Thr Met Trp Thr
                805                 810                 815

Thr Thr Leu Thr Arg Arg Asp Ile Ser Asn Trp Asp Pro Ala Ser Gln
            820                 825                 830

Asn Trp Val Val Thr Lys Tyr Pro Lys Thr Val Tyr Ile Gly Ser Ser
        835                 840                 845

Ser Arg Lys Leu His Leu Gln Ala Pro Leu Pro Pro Tyr
    850                 855                 860

<210> SEQ ID NO 62
<211> LENGTH: 685
<212> TYPE: PRT
<213> ORGANISM: Azospirillum irakense

<400> SEQUENCE: 62

Met Gly Ala Leu Arg Leu Leu Gly Ser Ile Ser Ile Val Ala Leu Thr
1               5                   10                  15

Cys Gly Gly Ile His Ala Ser Thr Ala Ile Ala Gln Glu Gly Ala Ala
            20                  25                  30

Pro Ala Ala Ile Leu His Pro Glu Lys Trp Pro Arg Pro Ala Thr Gln
        35                  40                  45

Arg Leu Ile Asp Pro Ala Val Glu Lys Arg Val Asp Ala Leu Leu Lys
    50                  55                  60

Gln Leu Ser Val Glu Glu Lys Val Gly Gln Val Ile Gln Gly Asp Ile
65                  70                  75                  80

Gly Thr Ile Thr Pro Glu Asp Leu Arg Lys Tyr Pro Leu Gly Ser Ile
                85                  90                  95

Leu Ala Gly Gly Asn Ser Gly Pro Asn Gly Asp Asp Arg Ala Pro Pro
            100                 105                 110

Lys Glu Trp Leu Asp Leu Ala Asp Ala Phe Tyr Arg Val Ser Leu Glu
        115                 120                 125

Lys Arg Pro Gly His Thr Pro Ile Pro Val Leu Phe Gly Ile Asp Ala
    130                 135                 140

Val His Gly His Gly Asn Ile Gly Ser Ala Thr Ile Phe Pro His Asn
145                 150                 155                 160

Ile Ala Leu Gly Ala Thr His Asp Pro Glu Leu Leu Arg Arg Ile Gly
                165                 170                 175

Glu Val Thr Ala Val Glu Met Ala Ala Thr Gly Ile Asp Trp Thr Phe
            180                 185                 190

Ala Pro Ala Leu Ser Val Val Arg Asp Asp Arg Trp Gly Arg Thr Tyr
        195                 200                 205

Glu Gly Phe Ser Glu Asp Pro Glu Ile Val Ala Ala Tyr Ser Ala Ala
    210                 215                 220

Ile Val Glu Gly Val Gln Gly Lys Phe Gly Ser Lys Asp Phe Met Ala
225                 230                 235                 240

Pro Gly Arg Ile Val Ala Ser Ala Lys His Phe Leu Ala Asp Gly Gly
                245                 250                 255

Thr Asp Gln Gly Arg Asp Gln Gly Asp Ala Arg Ile Ser Glu Asp Glu
            260                 265                 270

Leu Ile Arg Ile His Asn Ala Gly Tyr Pro Pro Ala Ile Asp Ala Gly
        275                 280                 285

Val Leu Thr Val Met Ala Ser Phe Ser Ser Trp Gln Gly Ile Lys His
    290                 295                 300

His Gly His Lys Gln Leu Leu Thr Asp Val Leu Lys Gly Gln Met Gly
```

```
            305                 310                 315                 320
        Phe Asn Gly Phe Ile Val Gly Asp Trp Asn Ala His Asp Gln Val Pro
                        325                 330                 335
        Gly Cys Thr Lys Phe Asn Cys Pro Thr Ser Leu Ile Ala Gly Leu Asp
                        340                 345                 350
        Met Tyr Met Ala Ala Asp Ser Trp Lys Gln Leu Tyr Glu Asn Thr Leu
                        355                 360                 365
        Ala Gln Val Lys Asp Gly Thr Ile Pro Met Ala Arg Leu Asp Asp Ala
                        370                 375                 380
        Val Arg Arg Ile Leu Arg Val Lys Val Leu Ala Gly Leu Phe Glu Lys
        385                 390                 395                 400
        Pro Ala Pro Lys Asp Arg Pro Gly Leu Pro Gly Leu Glu Thr Leu Gly
                        405                 410                 415
        Ser Pro Glu His Arg Ala Val Gly Arg Glu Ala Val Arg Lys Ser Leu
                        420                 425                 430
        Val Leu Leu Lys Asn Asp Lys Gly Thr Leu Pro Leu Ser Pro Lys Ala
                        435                 440                 445
        Arg Val Leu Val Ala Gly Asp Gly Ala Asp Asn Ile Gly Lys Gln Ser
        450                 455                 460
        Gly Gly Trp Thr Ile Ser Trp Gln Gly Thr Gly Asn Arg Asn Asp Glu
        465                 470                 475                 480
        Phe Pro Gly Ala Thr Ser Ile Leu Gly Gly Ile Arg Asp Ala Val Ala
                        485                 490                 495
        Asp Ala Gly Gly Ser Val Glu Phe Asp Val Ala Gly Gln Tyr Lys Thr
                        500                 505                 510
        Lys Pro Asp Val Ala Ile Val Val Phe Gly Glu Pro Tyr Ala Glu
                        515                 520                 525
        Phe Gln Gly Asp Val Glu Thr Leu Glu Tyr Gln Pro Asp Gln Lys Gln
                        530                 535                 540
        Asp Leu Ala Leu Leu Lys Lys Leu Lys Asp Gln Gly Ile Pro Val Val
        545                 550                 555                 560
        Ala Val Phe Leu Ser Gly Arg Pro Met Trp Val Asn Pro Glu Leu Asn
                        565                 570                 575
        Ala Ser Asp Ala Phe Val Ala Ala Trp Leu Pro Gly Thr Glu Gly Gly
                        580                 585                 590
        Gly Val Ala Asp Val Leu Phe Thr Asp Lys Ala Gly Lys Val Gln His
                        595                 600                 605
        Asp Phe Ala Gly Lys Leu Ser Tyr Ser Trp Pro Arg Thr Ala Ala Gln
                        610                 615                 620
        Thr Thr Val Asn Arg Gly Asp Ala Asp Tyr Asn Pro Leu Phe Ala Tyr
        625                 630                 635                 640
        Gly Tyr Gly Leu Thr Tyr Lys Asp Lys Ser Lys Val Gly Thr Leu Pro
                        645                 650                 655
        Glu Glu Ser Gly Val Pro Ala Glu Ala Arg Gln Asn Ala Gly Ile Tyr
                        660                 665                 670
        Phe Arg Ala Gly Ala Leu Arg Leu Pro Gly Arg Phe Leu
                        675                 680                 685

<210> SEQ ID NO 63
<211> LENGTH: 509
<212> TYPE: PRT
<213> ORGANISM: Myceliophthora thermophila

<400> SEQUENCE: 63
```

```
Gln Asn Ala Cys Thr Leu Thr Ala Glu Asn His Pro Ser Leu Thr Trp
  1               5                  10                  15

Ser Lys Cys Thr Ser Gly Gly Ser Cys Thr Ser Val Gln Gly Ser Ile
             20                  25                  30

Thr Ile Asp Ala Asn Trp Arg Trp Thr His Arg Thr Asp Ser Ala Thr
         35                  40                  45

Asn Cys Tyr Glu Gly Asn Lys Trp Asp Thr Ser Tyr Cys Ser Asp Gly
 50                  55                  60

Pro Ser Cys Ala Ser Lys Cys Cys Ile Asp Gly Ala Asp Tyr Ser Ser
 65                  70                  75                  80

Thr Tyr Gly Ile Thr Thr Ser Gly Asn Ser Leu Asn Leu Lys Phe Val
                     85                  90                  95

Thr Lys Gly Gln Tyr Ser Thr Asn Ile Gly Ser Arg Thr Tyr Leu Met
             100                 105                 110

Glu Ser Asp Thr Lys Tyr Gln Met Phe Gln Leu Leu Gly Asn Glu Phe
             115                 120                 125

Thr Phe Asp Val Asp Val Ser Asn Leu Gly Cys Gly Leu Asn Gly Ala
         130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                 165                 170                 175

Cys Pro Arg Asp Leu Lys Phe Ile Asn Gly Glu Ala Asn Val Glu Asn
             180                 185                 190

Trp Gln Ser Ser Thr Asn Asp Ala Asn Ala Gly Thr Gly Lys Tyr Gly
         195                 200                 205

Ser Cys Cys Ser Glu Met Asp Val Trp Glu Ala Asn Asn Met Ala Ala
210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
                 245                 250                 255

Cys Asp Pro Asp Gly Cys Asp Phe Asn Ser Tyr Arg Gln Gly Asn Lys
             260                 265                 270

Thr Phe Tyr Gly Lys Gly Met Thr Val Asp Thr Thr Lys Lys Ile Thr
         275                 280                 285

Val Val Thr Gln Phe Leu Lys Asn Ser Ala Gly Glu Leu Ser Glu Ile
290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Asp Trp Cys Asp
                 325                 330                 335

Arg Gln Lys Ala Ala Phe Gly Asp Val Thr Asp Phe Gln Asp Lys Gly
             340                 345                 350

Gly Met Val Gln Met Gly Lys Ala Leu Ala Gly Pro Met Val Leu Val
         355                 360                 365

Met Ser Ile Trp Asp Asp His Ala Val Asn Met Leu Trp Leu Asp Ser
370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                 405                 410                 415

Asn Ser Asn Val Ile Phe Ser Asn Ile Arg Phe Gly Pro Ile Gly Ser
```

```
                    420                 425                 430
Thr Val Ser Gly Leu Pro Asp Gly Gly Ser Gly Asn Pro Asn Pro Pro
            435                 440                 445

Val Ser Ser Ser Thr Pro Val Pro Ser Ser Thr Thr Ser Ser Gly
450                 455                 460

Ser Ser Gly Pro Thr Gly Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
                485                 490                 495

Thr Cys Thr Lys Leu Asn Asp Trp Tyr Ser Gln Cys Leu
            500                 505

<210> SEQ ID NO 64
<211> LENGTH: 395
<212> TYPE: PRT
<213> ORGANISM: Myceliophthora thermophila

<400> SEQUENCE: 64

Met Lys Phe Val Gln Ser Ala Thr Leu Ala Phe Ala Ala Thr Ala Leu
1               5                   10                  15

Ala Ala Pro Ser Arg Thr Thr Pro Gln Lys Pro Arg Gln Ala Ser Ala
            20                  25                  30

Gly Cys Ala Ser Ala Val Thr Leu Asp Ala Ser Thr Asn Val Phe Gln
        35                  40                  45

Gln Tyr Thr Leu His Pro Asn Asn Phe Tyr Arg Ala Glu Val Glu Ala
    50                  55                  60

Ala Ala Glu Ala Ile Ser Asp Ser Ala Leu Ala Glu Lys Ala Arg Lys
65                  70                  75                  80

Val Ala Asp Val Gly Thr Phe Leu Trp Leu Asp Thr Ile Glu Asn Ile
                85                  90                  95

Gly Arg Leu Glu Pro Ala Leu Glu Asp Val Pro Cys Glu Asn Ile Val
            100                 105                 110

Gly Leu Val Ile Tyr Asp Leu Pro Gly Arg Asp Cys Ala Ala Lys Ala
        115                 120                 125

Ser Asn Gly Glu Leu Lys Val Gly Glu Leu Asp Arg Tyr Lys Thr Glu
    130                 135                 140

Tyr Ile Asp Lys Ile Ala Glu Ile Leu Lys Ala His Ser Asn Thr Ala
145                 150                 155                 160

Phe Ala Leu Val Ile Glu Pro Asp Ser Leu Pro Asn Leu Val Thr Asn
                165                 170                 175

Ser Asp Leu Gln Thr Cys Gln Gln Ser Ala Ser Gly Tyr Arg Glu Gly
            180                 185                 190

Val Ala Tyr Ala Leu Lys Gln Leu Asn Leu Pro Asn Val Val Met Tyr
        195                 200                 205

Ile Asp Ala Gly His Gly Gly Trp Leu Gly Trp Asp Ala Asn Leu Lys
    210                 215                 220

Pro Gly Ala Gln Glu Leu Ala Ser Val Tyr Lys Ser Ala Gly Ser Pro
225                 230                 235                 240

Ser Gln Val Arg Gly Ile Ser Thr Asn Val Ala Gly Trp Asn Ala Trp
                245                 250                 255

Asp Gln Glu Pro Gly Glu Phe Ser Asp Ala Ser Asp Ala Gln Tyr Asn
            260                 265                 270

Lys Cys Gln Asn Glu Lys Ile Tyr Ile Asn Thr Phe Gly Ala Glu Leu
        275                 280                 285
```

```
Lys Ser Ala Gly Met Pro Asn His Ala Ile Ile Asp Thr Gly Arg Asn
290                 295                 300

Gly Val Thr Gly Leu Arg Asp Glu Trp Gly Asp Trp Cys Asn Val Asn
305                 310                 315                 320

Gly Ala Gly Phe Gly Val Arg Pro Thr Ala Asn Thr Gly Asp Glu Leu
                325                 330                 335

Ala Asp Ala Phe Val Trp Val Lys Pro Gly Gly Glu Ser Asp Gly Thr
            340                 345                 350

Ser Asp Ser Ser Ala Ala Arg Tyr Asp Ser Phe Cys Gly Lys Pro Asp
        355                 360                 365

Ala Phe Lys Pro Ser Pro Glu Ala Gly Thr Trp Asn Gln Ala Tyr Phe
370                 375                 380

Glu Met Leu Leu Lys Asn Ala Asn Pro Ser Phe
385                 390                 395

<210> SEQ ID NO 65
<211> LENGTH: 373
<212> TYPE: PRT
<213> ORGANISM: Myceliophthora thermophila

<400> SEQUENCE: 65

Gln Ser Gly Pro Trp Gln Gln Cys Gly Gly Ile Gly Trp Gln Gly Ser
1               5                   10                  15

Thr Asp Cys Val Ser Gly Tyr His Cys Val Tyr Gln Asn Asp Trp Tyr
            20                  25                  30

Ser Gln Cys Val Pro Gly Ala Ala Ser Thr Thr Leu Gln Thr Ser Thr
        35                  40                  45

Thr Ser Arg Pro Thr Ala Thr Ser Thr Ala Pro Pro Ser Ser Thr Thr
50                  55                  60

Ser Pro Ser Lys Gly Lys Leu Lys Trp Leu Gly Ser Asn Glu Ser Gly
65                  70                  75                  80

Ala Glu Phe Gly Glu Gly Asn Tyr Pro Gly Leu Trp Gly Lys His Phe
                85                  90                  95

Ile Phe Pro Ser Thr Ser Ala Ile Gln Thr Leu Ile Asn Asp Gly Tyr
            100                 105                 110

Asn Ile Phe Arg Ile Asp Phe Ser Met Glu Arg Leu Val Pro Asn Gln
        115                 120                 125

Leu Thr Ser Ser Phe Asp Glu Gly Tyr Leu Arg Asn Leu Thr Glu Val
130                 135                 140

Val Asn Phe Val Thr Asn Ala Gly Lys Tyr Ala Val Leu Asp Pro His
145                 150                 155                 160

Asn Tyr Gly Arg Tyr Tyr Gly Asn Val Ile Thr Asp Thr Asn Ala Phe
                165                 170                 175

Arg Thr Phe Trp Thr Asn Leu Ala Lys Gln Phe Ala Ser Asn Ser Leu
            180                 185                 190

Val Ile Phe Asp Thr Asn Asn Glu Tyr Asn Thr Met Asp Gln Thr Leu
        195                 200                 205

Val Leu Asn Leu Asn Gln Ala Ala Ile Asp Gly Ile Arg Ala Ala Gly
210                 215                 220

Ala Thr Ser Gln Tyr Ile Phe Val Glu Gly Asn Ala Trp Ser Gly Ala
225                 230                 235                 240

Trp Ser Trp Asn Thr Thr Asn Thr Asn Met Ala Ala Leu Thr Asp Pro
                245                 250                 255

Gln Asn Lys Ile Val Tyr Glu Met His Gln Tyr Leu Asp Ser Asp Ser
            260                 265                 270
```

```
Ser Gly Thr His Ala Glu Cys Val Ser Ser Asn Ile Gly Ala Gln Arg
        275                 280                 285

Val Val Gly Ala Thr Gln Trp Leu Arg Ala Asn Gly Lys Leu Gly Val
        290                 295                 300

Leu Gly Glu Phe Ala Gly Gly Ala Asn Ala Val Cys Gln Gln Ala Val
305                 310                 315                 320

Thr Gly Leu Leu Asp His Leu Gln Asp Asn Ser Asp Val Trp Leu Gly
                325                 330                 335

Ala Leu Trp Trp Ala Ala Gly Pro Trp Gly Asp Tyr Met Tyr Ser
                340                 345                 350

Phe Glu Pro Pro Ser Gly Thr Gly Tyr Val Asn Tyr Asn Ser Ile Leu
                355                 360                 365

Lys Lys Tyr Leu Pro
        370

<210> SEQ ID NO 66
<211> LENGTH: 851
<212> TYPE: PRT
<213> ORGANISM: Myceliophthora thermophila

<400> SEQUENCE: 66

Ile Glu Ser Arg Lys Val His Gln Lys Pro Leu Ala Arg Ser Glu Pro
1               5                   10                  15

Phe Tyr Pro Ser Pro Trp Met Asn Pro Asn Ala Asp Gly Trp Ala Glu
                20                  25                  30

Ala Tyr Ala Gln Ala Lys Ser Phe Val Ser Gln Met Thr Leu Leu Glu
            35                  40                  45

Lys Val Asn Leu Thr Thr Gly Val Gly Trp Gly Ala Glu Gln Cys Val
        50                  55                  60

Gly Gln Val Gly Ala Ile Pro Arg Leu Gly Leu Arg Ser Leu Cys Met
65                  70                  75                  80

His Asp Ser Pro Leu Gly Ile Arg Gly Ala Asp Tyr Asn Ser Ala Phe
                85                  90                  95

Pro Ser Gly Gln Thr Val Ala Ala Thr Trp Asp Arg Gly Leu Met Tyr
                100                 105                 110

Arg Arg Gly Tyr Ala Met Gly Gln Glu Ala Lys Gly Lys Gly Ile Asn
            115                 120                 125

Val Leu Leu Gly Pro Val Ala Gly Pro Leu Gly Arg Met Pro Glu Gly
        130                 135                 140

Gly Arg Asn Trp Glu Gly Phe Ala Pro Asp Pro Val Leu Thr Gly Ile
145                 150                 155                 160

Gly Met Ser Glu Thr Ile Lys Gly Ile Gln Asp Ala Gly Val Ile Ala
                165                 170                 175

Cys Ala Lys His Phe Ile Gly Asn Glu Gln Glu His Phe Arg Gln Val
                180                 185                 190

Pro Glu Ala Gln Gly Tyr Gly Tyr Asn Ile Ser Glu Thr Leu Ser Ser
            195                 200                 205

Asn Ile Asp Asp Lys Thr Met His Glu Leu Tyr Leu Trp Pro Phe Ala
        210                 215                 220

Asp Ala Val Arg Ala Gly Val Gly Ser Val Met Cys Ser Tyr Gln Gln
225                 230                 235                 240

Val Asn Asn Ser Tyr Ala Cys Gln Asn Ser Lys Leu Leu Asn Asp Leu
                245                 250                 255

Leu Lys Asn Glu Leu Gly Phe Gln Gly Phe Val Met Ser Asp Trp Gln
```

```
            260                 265                 270
Ala Gln His Thr Gly Ala Ala Ser Ala Val Ala Gly Leu Asp Met Ser
            275                 280                 285

Met Pro Gly Asp Thr Gln Phe Asn Thr Gly Val Ser Phe Trp Gly Ala
            290                 295                 300

Asn Leu Thr Leu Ala Val Leu Asn Gly Thr Val Pro Ala Tyr Arg Leu
305                 310                 315                 320

Asp Asp Met Ala Met Arg Ile Met Ala Ala Leu Phe Lys Val Thr Lys
                325                 330                 335

Thr Thr Asp Leu Glu Pro Ile Asn Phe Ser Phe Trp Thr Asp Asp Thr
            340                 345                 350

Tyr Gly Pro Ile His Trp Ala Ala Lys Gln Gly Tyr Gln Glu Ile Asn
            355                 360                 365

Ser His Val Asp Val Arg Ala Asp His Gly Asn Leu Ile Arg Glu Ile
            370                 375                 380

Ala Ala Lys Gly Thr Val Leu Leu Lys Asn Thr Gly Ser Leu Pro Leu
385                 390                 395                 400

Asn Lys Pro Lys Phe Val Ala Val Ile Gly Glu Asp Ala Gly Ser Ser
                405                 410                 415

Pro Asn Gly Pro Asn Gly Cys Ser Asp Arg Gly Cys Asn Glu Gly Thr
            420                 425                 430

Leu Ala Met Gly Trp Gly Ser Gly Thr Ala Asn Tyr Pro Tyr Leu Val
            435                 440                 445

Ser Pro Asp Ala Ala Leu Gln Ala Arg Ala Ile Gln Asp Gly Thr Arg
            450                 455                 460

Tyr Glu Ser Val Leu Ser Asn Tyr Ala Glu Glu Lys Thr Lys Ala Leu
465                 470                 475                 480

Val Ser Gln Ala Asn Ala Thr Ala Ile Val Phe Val Asn Ala Asp Ser
                485                 490                 495

Gly Glu Gly Tyr Ile Asn Val Asp Gly Asn Glu Gly Asp Arg Lys Asn
            500                 505                 510

Leu Thr Leu Trp Asn Asn Gly Asp Thr Leu Val Lys Asn Val Ser Ser
            515                 520                 525

Trp Cys Ser Asn Thr Ile Val Val Ile His Ser Val Gly Pro Val Leu
            530                 535                 540

Leu Thr Asp Trp Tyr Asp Asn Pro Asn Ile Thr Ala Ile Leu Trp Ala
545                 550                 555                 560

Gly Leu Pro Gly Gln Glu Ser Gly Asn Ser Ile Thr Asp Val Leu Tyr
            565                 570                 575

Gly Lys Val Asn Pro Ala Ala Arg Ser Pro Phe Thr Trp Gly Lys Thr
            580                 585                 590

Arg Glu Ser Tyr Gly Ala Asp Val Leu Tyr Lys Pro Asn Asn Gly Asn
            595                 600                 605

Gly Ala Pro Gln Gln Asp Phe Thr Glu Gly Val Phe Ile Asp Tyr Arg
            610                 615                 620

Tyr Phe Asp Lys Val Asp Asp Ser Val Ile Tyr Glu Phe Gly His
625                 630                 635                 640

Gly Leu Ser Tyr Thr Thr Phe Glu Tyr Ser Asn Ile Arg Val Val Lys
            645                 650                 655

Ser Asn Val Ser Glu Tyr Arg Pro Thr Thr Gly Thr Thr Ala Gln Ala
            660                 665                 670

Pro Thr Phe Gly Asn Phe Ser Thr Asp Leu Glu Asp Tyr Leu Phe Pro
            675                 680                 685
```

-continued

```
Lys Asp Glu Phe Pro Tyr Ile Tyr Gln Tyr Ile Tyr Pro Tyr Leu Asn
    690                 695                 700

Thr Thr Asp Pro Arg Arg Ala Ser Ala Asp Pro His Tyr Gly Gln Thr
705                 710                 715                 720

Ala Glu Glu Phe Leu Pro Pro His Ala Thr Asp Asp Pro Gln Pro
                725                 730                 735

Leu Leu Arg Ser Ser Gly Gly Asn Ser Pro Gly Gly Asn Arg Gln Leu
                740                 745                 750

Tyr Asp Ile Val Tyr Thr Ile Thr Ala Asp Ile Thr Asn Thr Gly Ser
            755                 760                 765

Val Val Gly Glu Glu Val Pro Gln Leu Tyr Val Ser Leu Gly Gly Pro
    770                 775                 780

Glu Asp Pro Lys Val Gln Leu Arg Asp Phe Asp Arg Met Arg Ile Glu
785                 790                 795                 800

Pro Gly Glu Thr Arg Gln Phe Thr Gly Arg Leu Thr Arg Arg Asp Leu
                805                 810                 815

Ser Asn Trp Asp Val Thr Val Gln Asp Trp Val Ile Ser Arg Tyr Pro
                820                 825                 830

Lys Thr Ala Tyr Val Gly Arg Ser Ser Arg Lys Leu Asp Leu Lys Ile
            835                 840                 845

Glu Leu Pro
    850

<210> SEQ ID NO 67
<211> LENGTH: 509
<212> TYPE: PRT
<213> ORGANISM: Myceliophthora thermophila

<400> SEQUENCE: 67

Gln Asn Ala Cys Thr Leu Thr Ala Glu Asn His Pro Ser Leu Thr Trp
1               5                   10                  15

Ser Lys Cys Thr Ser Gly Gly Ser Cys Thr Ser Val Gln Gly Ser Ile
            20                  25                  30

Thr Ile Asp Ala Asn Trp Arg Trp Thr His Arg Thr Asp Ser Ala Thr
        35                  40                  45

Asn Cys Tyr Glu Gly Asn Lys Trp Asp Thr Ser Tyr Cys Ser Asp Gly
    50                  55                  60

Pro Ser Cys Ala Ser Lys Cys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
                85                  90                  95

Thr Lys Gly Gln Tyr Ser Thr Asn Ile Gly Ser Arg Thr Tyr Leu Met
            100                 105                 110

Glu Ser Asp Thr Lys Tyr Gln Met Phe Gln Leu Leu Gly Asn Glu Phe
        115                 120                 125

Thr Phe Asp Val Asp Val Ser Asn Leu Gly Cys Gly Leu Asn Gly Ala
    130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Glu Ala Asn Val Glu Asn
            180                 185                 190

Trp Gln Ser Ser Thr Asn Asp Ala Asn Ala Gly Thr Gly Lys Tyr Gly
```

```
        195                 200                 205
Ser Cys Cys Ser Glu Met Asp Val Trp Glu Ala Asn Asn Met Ala Ala
210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
                245                 250                 255

Cys Asp Pro Asp Gly Cys Asp Phe Asn Ser Tyr Arg Gln Gly Asn Lys
            260                 265                 270

Thr Phe Tyr Gly Lys Gly Met Thr Val Asp Thr Thr Lys Lys Ile Thr
        275                 280                 285

Val Val Thr Gln Phe Leu Lys Asn Ser Ala Gly Glu Leu Ser Glu Ile
    290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Ala Ala Phe Gly Asp Val Thr Asp Phe Gln Asp Lys Gly
            340                 345                 350

Gly Met Val Gln Met Gly Lys Ala Leu Ala Gly Pro Met Val Leu Val
        355                 360                 365

Met Ser Ile Trp Asp Asp His Ala Val Asn Met Leu Trp Leu Asp Ser
    370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Ile Phe Ser Asn Ile Arg Phe Gly Pro Ile Gly Ser
            420                 425                 430

Thr Val Ser Gly Leu Pro Asp Gly Gly Ser Gly Asn Pro Asn Pro Pro
        435                 440                 445

Val Ser Ser Ser Thr Pro Val Pro Ser Ser Ser Thr Thr Ser Ser Gly
    450                 455                 460

Ser Ser Gly Pro Thr Gly Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
                485                 490                 495

Thr Cys Thr Lys Leu Asn Asp Trp Tyr Ser Gln Cys Leu
            500                 505

<210> SEQ ID NO 68
<211> LENGTH: 465
<212> TYPE: PRT
<213> ORGANISM: Myceliophthora thermophila

<400> SEQUENCE: 68

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
            20                  25                  30

Thr Cys Val Ala Gln Asn Glu Trp Tyr Ser Gln Cys Leu Pro Asn Ser
        35                  40                  45

Gln Val Thr Ser Ser Thr Thr Pro Ser Ser Thr Ser Thr Ser Gln Arg
    50                  55                  60
```

-continued

```
Ser Thr Ser Thr Ser Ser Ser Thr Arg Ser Gly Ser Ser Ser Ser
 65                  70                  75                  80

Ser Ser Thr Thr Pro Pro Pro Val Ser Ser Pro Val Thr Ser Ile Pro
                 85                  90                  95

Gly Gly Ala Thr Ser Thr Ala Ser Tyr Ser Gly Asn Pro Phe Ser Gly
            100                 105                 110

Val Arg Leu Phe Ala Asn Asp Tyr Tyr Arg Ser Glu Val His Asn Leu
        115                 120                 125

Ala Ile Pro Ser Met Thr Gly Thr Leu Ala Ala Lys Ala Ser Ala Val
    130                 135                 140

Ala Glu Val Pro Ser Phe Gln Trp Leu Asp Arg Asn Val Thr Ile Asp
145                 150                 155                 160

Thr Leu Met Val Gln Thr Leu Ser Gln Val Arg Ala Leu Asn Lys Ala
                165                 170                 175

Gly Ala Asn Pro Pro Tyr Ala Ala Gln Leu Val Val Tyr Asp Leu Pro
            180                 185                 190

Asp Arg Asp Cys Ala Ala Ala Ser Asn Gly Glu Phe Ser Ile Ala
        195                 200                 205

Asn Gly Gly Ala Ala Asn Tyr Arg Ser Tyr Ile Asp Ala Ile Arg Lys
    210                 215                 220

His Ile Ile Glu Tyr Ser Asp Ile Arg Ile Ile Leu Val Ile Glu Pro
225                 230                 235                 240

Asp Ser Met Ala Asn Met Val Thr Asn Met Asn Val Ala Lys Cys Ser
                245                 250                 255

Asn Ala Ala Ser Thr Tyr His Glu Leu Thr Val Tyr Ala Leu Lys Gln
            260                 265                 270

Leu Asn Leu Pro Asn Val Ala Met Tyr Leu Asp Ala Gly His Ala Gly
        275                 280                 285

Trp Leu Gly Trp Pro Ala Asn Ile Gln Pro Ala Ala Glu Leu Phe Ala
    290                 295                 300

Gly Ile Tyr Asn Asp Ala Gly Lys Pro Ala Ala Val Arg Gly Leu Ala
305                 310                 315                 320

Thr Asn Val Ala Asn Tyr Asn Ala Trp Ser Ile Ala Ser Ala Pro Ser
                325                 330                 335

Tyr Thr Ser Pro Asn Pro Asn Tyr Asp Glu Lys His Tyr Ile Glu Ala
            340                 345                 350

Phe Ser Pro Leu Leu Asn Ser Ala Gly Phe Pro Ala Arg Phe Ile Val
        355                 360                 365

Asp Thr Gly Arg Asn Gly Lys Gln Pro Thr Gly Gln Gln Gln Trp Gly
    370                 375                 380

Asp Trp Cys Asn Val Lys Gly Thr Gly Phe Gly Val Arg Pro Thr Ala
385                 390                 395                 400

Asn Thr Gly His Glu Leu Val Asp Ala Phe Val Trp Val Lys Pro Gly
                405                 410                 415

Gly Glu Ser Asp Gly Thr Ser Thr Ser Ala Ala Arg Tyr Asp Tyr
            420                 425                 430

His Cys Gly Leu Ser Asp Ala Leu Gln Pro Ala Pro Glu Ala Gly Gln
        435                 440                 445

Trp Phe Gln Ala Tyr Phe Glu Gln Leu Leu Thr Asn Ala Asn Pro Pro
    450                 455                 460

Phe
465
```

```
<210> SEQ ID NO 69
<211> LENGTH: 35
<212> TYPE: DNA
<213> ORGANISM: Artificial sequence
<220> FEATURE:
<223> OTHER INFORMATION: Synthetic DNA forward primer

<400> SEQUENCE: 69
tacttcttct ccaccatgtc caaggcctct gctct                              35

<210> SEQ ID NO 70
<211> LENGTH: 36
<212> TYPE: DNA
<213> ORGANISM: Artificial sequence
<220> FEATURE:
<223> OTHER INFORMATION: Synthetic DNA reverse primer

<400> SEQUENCE: 70
ggatccgaat tcttattaca aacactggga gtacca                             36
```